US008563001B2

(12) United States Patent
Dodge et al.

(10) Patent No.: US 8,563,001 B2
(45) Date of Patent: Oct. 22, 2013

(54) MULTICOMPONENT IMMUNOGENIC COMPOSITION FOR THE PREVENTION OF BETA-HEMOLYTIC STREPTOCOCCAL (BHS) DISEASE

(75) Inventors: Ingrid Lea Dodge, Cornwall, NY (US); Annaliesa Sybil Anderson, Upper Saddle River, NJ (US); Michael Hagen, Pittsford, NY (US); Stephen Bruce Olmsted, West Nyack, NY (US)

(73) Assignee: Regents of the University of Minnesota, St. Paul, MN (US)

( * ) Notice: Subject to any disclaimer, the term of this patent is extended or adjusted under 35 U.S.C. 154(b) by 103 days.

(21) Appl. No.: 12/612,399

(22) Filed: Nov. 4, 2009

(65) Prior Publication Data

US 2010/0119534 A1 May 13, 2010

Related U.S. Application Data

(60) Provisional application No. 61/111,485, filed on Nov. 5, 2008.

(51) Int. Cl.
*A61K 39/09* (2006.01)
*A61K 39/02* (2006.01)

(52) U.S. Cl.
USPC .................. 424/185.1; 424/184.1; 424/244.1

(58) Field of Classification Search
None
See application file for complete search history.

(56) References Cited

U.S. PATENT DOCUMENTS

| | | | |
|---|---|---|---|
| 4,152,411 | A | 5/1979 | Schall, Jr. |
| 4,346,074 | A | 8/1982 | Gilmour et al. |
| 4,376,110 | A | 3/1983 | David et al. |
| 4,454,121 | A | 6/1984 | Beachey |
| 4,554,101 | A | 11/1985 | Hopp |
| 4,650,764 | A | 3/1987 | Temin et al. |
| 4,666,829 | A | 5/1987 | Glenner et al. |
| 4,673,574 | A | 6/1987 | Anderson |
| 4,695,562 | A | 9/1987 | Beachey et al. |
| 4,772,584 | A | 9/1988 | Cleary et al. |
| 4,784,948 | A | 11/1988 | Scott et al. |
| 4,797,368 | A | 1/1989 | Carter et al. |
| 4,837,151 | A | 6/1989 | Stocker |
| 4,902,506 | A | 2/1990 | Anderson et al. |
| 4,912,094 | A | 3/1990 | Myers et al. |
| 4,989,289 | A | 2/1991 | Bargellini |
| 5,057,540 | A | 10/1991 | Kensil et al. |
| 5,078,996 | A | 1/1992 | Conlon, III et al. |
| 5,097,020 | A | 3/1992 | Anderson et al. |
| 5,124,153 | A | 6/1992 | Beachey et al. |
| 5,139,941 | A | 8/1992 | Muzyczka et al. |
| 5,162,226 | A | 11/1992 | Beachey et al. |
| 5,168,062 | A | 12/1992 | Stinski |
| 5,360,897 | A | 11/1994 | Anderson et al. |
| 5,399,346 | A | 3/1995 | Anderson et al. |
| 5,459,127 | A | 10/1995 | Felgner et al. |
| 5,580,859 | A | 12/1996 | Felgner et al. |
| 5,589,466 | A | 12/1996 | Felgner et al. |
| 5,593,972 | A | 1/1997 | Weiner et al. |
| 5,643,576 | A | 7/1997 | Johnston et al. |
| 5,679,654 | A | 10/1997 | Tzianabos et al. |
| 5,723,127 | A | 3/1998 | Scott et al. |
| 5,848,547 | A | 12/1998 | Hite |
| 6,100,380 | A | 8/2000 | Green et al. |
| 6,113,918 | A | 9/2000 | Johnson et al. |
| 6,127,170 | A | 10/2000 | Boutin |
| 6,168,911 | B1 | 1/2001 | Lelental et al. |
| 6,168,943 | B1 | 1/2001 | Rose |
| 6,207,646 | B1 | 3/2001 | Krieg et al. |
| 6,270,775 | B1 | 8/2001 | Cleary |
| 6,355,255 | B1 | 3/2002 | Cleary et al. |
| 6,951,653 | B2 | 10/2005 | Cleary et al. |
| 7,256,265 | B2 | 8/2007 | Cleary et al. |
| 7,635,483 | B2 | 12/2009 | Cleary et al. |
| 7,638,136 | B2 * | 12/2009 | Meinke et al. ............. 424/244.1 |
| 7,838,010 | B2 * | 11/2010 | Bensi et al. ................ 424/237.1 |
| 2004/0052801 | A1 | 3/2004 | Cleary et al. |
| 2005/0136068 | A1 | 6/2005 | Cleary et al. |
| 2006/0153879 | A1 | 7/2006 | Cleary et al. |

FOREIGN PATENT DOCUMENTS

| | | | |
|---|---|---|---|
| CA | 2012311 | C | 6/2003 |
| EP | 0125023 | A1 | 11/1984 |
| EP | 0171496 | A2 | 2/1986 |
| EP | 0173494 | A2 | 3/1986 |
| EP | 0178220 | A2 | 4/1986 |
| EP | 0184187 | A2 | 6/1986 |
| EP | 0185573 | A1 | 6/1986 |
| EP | 0272929 | A2 | 6/1988 |
| EP | 0371199 | A1 | 6/1990 |
| EP | 0453242 | A1 | 10/1991 |
| EP | 0488528 | A1 | 6/1992 |
| EP | 1075841 | A1 | 2/2001 |

(Continued)

OTHER PUBLICATIONS

Houghten et al. (Vaccines, 1986, Edited by Fred Brown: Cold Spring Harbor Laboratory).*

Madore, D. V. 1998. Characterization of immune response as an indicator of *Haemophilus influenzae* type b vaccine efficacy. Pediatr Infect Dis J. 17:S207-10.

(Continued)

*Primary Examiner* — Padma V Baskar

(74) *Attorney, Agent, or Firm* — Viksnins Harris & Padys PLLP

(57) ABSTRACT

A number of β-hemolytic streptococci polynucleotides and polypeptides, particularly *Streptococcus pyogenes* polypeptides and polynucleotides, are described. Two or more of the polypeptides of the invention can be formulated for use as immunogenic compositions. Also disclosed are methods for immunizing against and reducing infection caused by β-hemolytic streptococci.

49 Claims, 16 Drawing Sheets

(56) References Cited

FOREIGN PATENT DOCUMENTS

| | | | | |
|---|---|---|---|---|
| WO | WO 86/01533 | A1 | | 3/1986 |
| WO | WO 86/02269 | A1 | | 4/1986 |
| WO | WO 89/07150 | A1 | | 8/1989 |
| WO | WO 89/09063 | A1 | | 10/1989 |
| WO | WO 89/09064 | A1 | | 10/1989 |
| WO | WO 90/02806 | A1 | | 3/1990 |
| WO | WO 91/18088 | A1 | | 11/1991 |
| WO | WO 91/19740 | A1 | | 12/1991 |
| WO | WO 92/02612 | A2 | | 2/1992 |
| WO | WO 92/05263 | A1 | | 4/1992 |
| WO | WO 92/19265 | A1 | | 11/1992 |
| WO | WO 93/09239 | A1 | | 5/1993 |
| WO | WO 93/14198 | A1 | | 7/1993 |
| WO | WO 93/18157 | A1 | | 9/1993 |
| WO | WO 93/21220 | A1 | | 10/1993 |
| WO | WO 94/06421 | A1 | | 3/1994 |
| WO | WO 94/06465 | A1 | | 3/1994 |
| WO | WO 94/12649 | A2 | | 6/1994 |
| WO | WO 94/21807 | A2 | | 9/1994 |
| WO | WO 94/26914 | A1 | | 11/1994 |
| WO | WO 94/28152 | A1 | | 12/1994 |
| WO | WO 94/28938 | A1 | | 12/1994 |
| WO | WO 95/02697 | A1 | | 1/1995 |
| WO | WO 95/07358 | A1 | | 3/1995 |
| WO | WO 95/18863 | A1 | | 7/1995 |
| WO | WO 95/21931 | A1 | | 8/1995 |
| WO | WO 95/22617 | A1 | | 8/1995 |
| WO | WO 95/26411 | A2 | | 10/1995 |
| WO | WO 95/28494 | A1 | | 10/1995 |
| WO | WO 95/28960 | A1 | | 11/1995 |
| WO | WO 96/17823 | A1 | | 6/1996 |
| WO | WO 96/22378 | A1 | | 6/1996 |
| WO | WO 96/25508 | A1 | | 8/1996 |
| WO | WO 96/39036 | A1 | | 12/1996 |
| WO | WO 97/19182 | A1 | | 5/1997 |
| WO | WO 97/26008 | A1 | | 7/1997 |
| WO | WO 98/02697 | A1 | | 1/1998 |
| WO | WO 98/13501 | A2 | | 4/1998 |
| WO | WO 99/01157 | A1 | | 1/1999 |
| WO | WO 99/01158 | A1 | | 1/1999 |
| WO | WO 99/01175 | A1 | | 1/1999 |
| WO | WO 99/27944 | A1 | | 6/1999 |
| WO | WO 00/18434 | A1 | | 4/2000 |
| WO | WO 00/37648 | A1 | | 6/2000 |
| WO | WO0234771 | A2 | * | 5/2002 |
| WO | WO 02/077183 | A2 | | 10/2002 |
| WO | WO 02/083859 | A2 | | 10/2002 |
| WO | WO 2004/078907 | A2 | | 9/2004 |
| WO | WO2004/078907 | A3 | | 9/2004 |
| WO | WO2004078907 | A2 | * | 9/2004 |
| WO | WO 2005/076010 | A2 | | 8/2005 |
| WO | WO 2006/042027 | A2 | | 4/2006 |
| WO | WO2006/042027 | A3 | | 4/2006 |
| WO | WO2006042027 | A2 | * | 4/2006 |
| WO | WO2009/155476 | A2 | | 12/2009 |
| WO | WO2009/155484 | A2 | | 12/2009 |

OTHER PUBLICATIONS

Molinari, G., S. R. Talay, P. Valentin-Weigand, M. Rohde, and G. S. Chhatwal. 1997. The fibronectin-binding protein of *Streptococcus pyogenes*, Sfbl, is involved in the internalization of group A streptococci by epithelial cells. Infect Immun. 65:1357-63.

Jones, K. F., and V. A. Fischetti. 1988. The importance of the location of antibody binding on the M6 protein for opsonization and phagocytosis of group A M6 streptococci. J Exp Med. 167:1114-23.

Cheng Qi et al., Immunization with $C5_a$ peptidase or peptidase-type III polysaccharide conjugate vaccines enhances clearance of group B streptococci from lungs of infected mice. *Infection and Immunity*, vol. 70, No. 11, Nov. 2002.

Maione Domenico et al., Identification of a universal Group B Streptococcus vaccine by multiple genome screen. *Science, American Association for the Advancement of Science*, vol. 309, No. 5731, Jul. 2005.

Dale J. B. et al., Group A and Group B streptoccal vaccine development a round table presentation. *Advance in Experimental Medicine and Biology*, vol. 418, Jan. 1997.

McMillan D. J. et al., Identification and assessment of new vaccine candidates for group A streptococcal infections, *Vaccine, Butterworth Scientific*, vol. 22, No. 21-22, Jul. 2004.

International Search Report dated Feb. 25, 2010.

Bessen, D., et al., "Influence of Intranasal Immunization with Synthetic Peptides Corresponding to Conserved Epitopes of M Protein on Mucosal Colonization by Group A Streptococci", Infection and Immunity, 56(10):2666-2672 (1988).

Bessen, D., et al., "Synthetic Peptide Vaccine Against Mucosal Colonization by Group A Streptococci", The Journal of Immunology, 145(4):1251-1256 (1990).

Boyle, M.D.P., et al., "Measurement of Leukocyte Chemataxis in Vivo", Methods in Enzymology, 162:101-114 (1988).

Bronze, M.S., et al., "Protective Immunity Evoked by Locally Admisistered Group A Streptococcal Vaccines in Mice[1]", The Journal of Immunology, 141(8):2767-2770 (1988).

Brummer, E., et al., "Immunological Activation of Polymorphonuclear Neutrophils for Fungal Killing: Studies With Murine Cells and Blastomyces dermatitidis In Vitro", Journal of Leukocyte Biology, 36:505-520 (1984).

Carter, P., et al., "Dissecting the catalytic triad of a serine protease", Nature, 332:564-568 (1988).

Chen, C.C., et al., "Complete Nucleotide Sequence of the Streptococcal C5a Peptidase Gene of *Streptococcus pyogenes*", The Journal of Biological Chemistry, 265(6):3161-3167 (1990).

Cleary, P.P., et al., "Similarity between the group B and A Streptococcal C5a peptidase genes", Infection and Immunity, 60(10):4239-4244 (1992).

Cleary, P.P., et al., "Streptococcal C5a peptidase is a highly specific endopeptidase", Infection and Immunity, 60(12):5219-5223 (1992).

Cleary, P.P., et al., "Virulent human strains of group G streptococci express a C5a peptidase enzyme similar to that produced by group A streptococci", Infection and Immunity, 59(7):2305-2310 (1991).

Coid, C.R., "*Escherichia coli* and group B streptococcal infections in experimental animals", Ciba Found Symp., 77:103-118 (1979) (Abstract only).

Courtney, H.S., et al., "Analysis of the Role of M24 Protein in Group A Streptococcal Adhesion and Colonization by Use of Ω-Interposon Mutagenesis", Infection and Immunity, 62(11):4868-4873 (1994).

Fenderson, P.G., et al., "Tropomyosin Shares Immunologic Epitopes with Group A Streptococcal M Proteins[1]", The Journal of Immunology, 142(7):2475-2481 (1989).

Fischetti, V.A., "Streptococcal M protein: molecular design and biological behavior", Clinical Microbiology Reviews, 2(3):285-314 (1989).

Fischetti, V.A., et al., "Protection Against Streptococcal Pharyngeal Colonization with a Vaccinia: M Protein Recombinant", Science, 244:1487-1490 (1989).

Fischetti, V.A., et al., "Protection against streptococcal pharynogeal colonization with vaccines composed of M protein conserved regions", Immunobiology of Proteins and Peptides VI, M.Z. Atassi, ed. (Plenum Press, New York, NY) pp. 159-167 (1991).

Friedman, H., et al., "Immunoadjuvanticity of Endotoxins and Nontoxic Derivatives for Normal and Leukemic Immunocytes", Advances in Experimental Medicine and Biology, 256:525-535 (1990).

Hill, H.R., et al., "Group B Streptococci Inhibit the Chemotactic Activity of the Fifth Component of Complement[1]", The Journal of Immunology, 141(10):3551-3556 (1988).

Ji, Y., et al., "C5a peptidase alters clearance and trafficking of a group A streptococci by infected mice", Infection and Immunity, 64(2):503-510 (1996).

Ji, Y., et al, "Intranasal immunization with C5a peptidase prevents nasopharyngeal colonization of mice by the group A *Streptococcus*", Infection and Immunity, 65(6):2080-2087 (1997).

Kapur, V., et al., "Vaccination with streptococcal extracellular cysteine protease (interleukin-1β convertase) protects mice against challenge with heterologous group A streptococci", Microbial Pathogenesis, 16(6):443-450 (1994).

(56) References Cited

OTHER PUBLICATIONS

Laemmli, U.K., "Cleavage of Structural Proteins during the Assembly of the Head of Bacteriophage T4", Nature, 227:680-685 (1970).
Lee, P.K., et al., "Quantification and Toxicity of Group A Streptococcal Pyrogenic Exotoxins in an Animal Model of Toxic Shock Syndrome-Like Illness", Journal of Clinical Microbiology, 27(8):1890-1892 (1989).
Martin, T., et al., "The Effect of Type-Specific Polysaccharide Capsule on the Clearance of Group B Streptococci from the Lungs of Infant and Adult Rats", The Journal of Infectious Diseases, 165(2):306-314 (1992).
Massell, B.F., et al., "Rheumatic Fever Following Streptococcal Vaccination: Report of Three Cases", JAMA, 207(6):1115-1119 (1989).
Medaglini, D., et al., Mucosal and systemic immune responses to a recombinant protein expressed on the surface of the oral commensal bacterium *Streptococcus gordonii* after oral colonization, Proc. Natl. Acad. Sci. USA, 92(15):6868-6872 (1995).
O'Connor, S., et al., "In Vivo *Streptococcus pyogenes* C5a Peptidase Activity: Analysis Using Transposon-and Nitrosoguanidine-Induced Mutants", The Journal of Infectious Diseases, 156(3):495-504 (1987).
O'Connor, S., et al., "The Human Antibody Response to Streptococcal C5a Peptidase", The Journal of Infectious Diseases, 163:109-116 (1991).
Podbielski, A., et al., "The Group A streptococcal *virR49* Gene Controls Expression of Four Structural *vir* Regulon Genes", Infection and Immunity, 63(1):9-20 (1995).
Raeder, R., et al., "Properties of IgG-Binding Proteins Expressed by *Streptococcus pyogenes* Isolates Are Predictive of Invasive Potential", The Journal of Infectious Diseases, 173(4):888-895 (1996).
Robles, G., et al., "Antibodies against extracellular products of group A *Streptococcus*: Diagnostic importance in the acute rheumatic fever", Arch. Inst. Cardiol. Mex., 65(2):115-119 (1995) (Abstract only).
Rossi, F., et al., "Engineered Idiotypes: Immunochemical Analysis of Antigenized Antibodies expressing A Conformationally Constrained ARG-GLY-ASP Motif", Molecular Immunology, 32(5):341-346 (1995).
Sriskandan, S., et al., "Streptococcal Pyrogenic Exotoxin A Release, Distribution, and Role in Murine Model of Fasciitis and Multiorgan Failure Due to *Streptococcus pyogenes*", Journal of Infectious Diseases, 173(6):1399-1407 (1996).
Sriskandan, S., et al., "The Role of Nitric Oxide in Experimental Murine Sepsis Due to Pyrogenic Exotoxin A-Producing *Streptococcus pyogenes*", Infection and Immunity, 65(5):1767-1772 (1997).
Stevens, D.L., "Invasive Group A *Streptococcus* Infections", Clinical Infectious Diseases, 14(1):2-11 (1992).
Wexler, D.E., et al., "Purification and Characteristics of the Streptococcal Chemotactic Factor Inactivator", Infection and Immunity, 50(3):757-764 (1985).
Accession No. A35066 (1987).
Alexander, et al., "Amino acid changes affecting the activity of pneumolysin alter the behaviour of pneumococci in pneumonia", Microbial Pathogenesis, 24(3):167-174 (1998).
Alm, R.A., et al., "Genomic-sequence comparison of two unrelated isolates of the human gastric pathogen Helicobacter pylori", Nature 379:176-180 (1999) [published erratum appears in Nature 379(6721):719 (1999)].
Altschul, S.F., et al., "Protein database searches for multiple alignments", Proc. Natl. Acad. Sci. USA, 87:5509-5513 (1990).
Altschul, S.F., et al., "Gapped BLAST and PSI-BLAST: a new generation of protein database search programs", Nucleic Acids Research, 25(17):3389-3402 (1997).
Anderson, T.F., et al., "Techniques for the Preservation of Three-Diminsional Structure in Preparing Specimens for the Electron Microscope", Transactions of The New York Academy of Sciences, 13(4):130-134 (1951).
Anderson, E.T., et al., "Processing, stability, and kinetic parameters of C5a peptidase from *Streptococcus* pyogenes", Eur. J. Biochem., 269:4839-4851 (2002).
Ausubel, F.M., et al., "Current Protocols in Molecular Biology", John Wiley & Sons, Inc., vol. 1, Sections 2.10 and 6.3-6.4 (1995).
Banks, D.J., et al., "Progress toward Characterization of the Group A *Streptococcus* Metagenome: Complete Genome Sequence of a Macrolide-Resistant Serotype M6 Strain", Journal of Infectious Diseases, 190(4):727-738 (2004).
Bateman, A., et al., "The Pfam Protein Families Database", Nucleic Acids Research, 28(1):263-266 (2000).
Beard, C.W., et al., Transcription Mapping of Mouse Adenovirus Type 1 Early Region 3, Virology, 175:81-90 (1990).
Bender, M.A., et al., "Evidence that the Packaging Signal of Moloney Murine Leukemia Virus Extends into the gag Region", Journal of Virology, 61(5):1639-1646 (1987).
Benson, G., "Tandem repeats finder: a program to analyze DNA sequences", Nucleic Acids Research, 27(2):573-580 (1999).
Beres, S.B., et al., "Molecular genetic anatomy of inter- and intraserotype variation in the human bacterial pathogen group A *Streptococcus*", PNAS, 103(18):7059-7064 (2006).
Berg, A., et al., "Streptococcal Cysteine Proteinase Releases Biologically Active Fragments of Streptococcal Surface Proteins", The Journal of Biological Chemistry, 270(17):9862-9867 (1995).
Better, M., et al., "*Escherichia coli* Secretion of an Active Chimeric Antibody Fragment", Science, 240:1041-1043 (1988).
Booth, S.A., et al., "Dapsone Suppresses Integrin-Mediated Neutrophil Adherence Function", The Journal of Investigative Dermatology, 98(2):135-140 (1992).
Bronze, M.S., et al., "Epitopes of Group A Streptococcal M Protein that Envoke Cross-Protective Local Immune Responses", The Journal of Immunology, 148(3):888-893 (1992).
Brown, C.K., et al., "Structure of the streptococcal cell wall C5a peptidase", PNAS, 102(51):18391- 18396 (2005).
Cabilly, S., et al., "Generation of antibody activity from immunoglobulin polypeptide chains produced in *Escherichia coli*", Proc. Natl. Acad. Sci. USA, 81:273-3277 (1984).
Carrillo, H., et al., "The Multiple Sequence Alignment Problem in Biology", SIAM J. Appl. Math., 48(5):1073-1082 (1988).
Chen, C.C., et al., "Cloning and Expression of the Streptococcal C5a Peptidase Gene in *Escherichia coli*: Linkage to the Type 12 M Protein Gene", Infection and Immunity, 57(6):1740-1745 (1989).
Cheng, Q., et al., "Antibody Against Surface-Bound C5a Peptidase is Opsonic and Initiates Macrophage Killing of Group B Streptococci", Infection and Immunity, 69(4):2302-2308 (2001).
Cheng, Q., et al., "The Group B Streptococcal C5a peptidase is Both a Specific Protease and an Invasin", Infection and Immunity, 70(5):2408-2413 (2002).
Chmouryguina, I., et al., "Conservation of the C5a peptidase genes in group A and B streptococci", Infection and Immunity, 64(7):2387-2390 (1996).
Clark, J.M., et al., "A New Method for Quantitation of Cell-Mediated Immunity in the Mouse", Journal of the Reticuloendothelial Society, 25(3):255-267 (1979).
Cleary, P., et al., "A Streptococcal Inactivator of Chemotaxis: A new Virulence Factor Specific to Group A Streptococci", Recent Advances in Streptococci and Streptococcal Diseases, Y. Kimura, S. Kotami and Y. Shiokawa, eds., Reedbooks Ltd, Berkshire, England, pp. 179-180 (1984).
Cleary, P.P., et al., "Immunization with C5a peptidase from either group A or B streptococci enhances clearance of group A streptococci from intranasally infected mice", Vaccine, 22(31-32):4332-4341 (2004).
Cockerill, F.R., et al., "Molecular, Serological, and Clinical Features of 16 Consecutive Cases of Invasive Streptococcal Disease", Clin. Infect. Dis., 26(6):1448-1458 (1998).
Courtney, H.S., et al., "Cloning, sequencing, and expression of a fibronectin/fibrinogen-binding protein from group A streptococci", Infection and Immunity, 62(9):3937-3946 (1994).
Cserzo, M., et al., "Prediction of transmembrane α-helices in prokaryotic membrane proteins: the dense alignment surface method", Protein Engineering, 10(6):673-676 (1997).
Cunningham, M.W., et al., "Immunological Crossreactivity Between the Class I Epitope of Streptococcal M Protein and Myosin", Advances in Experimental Medicine and Biology, 418:887-892 (1997).

(56) References Cited

OTHER PUBLICATIONS

Curiel, D.T., et al., "High-Efficiency Gene Transfer Mediated by Adenovirus Coupled to DNA Polylysine Complexes", Human Gene Therapy, 3:147-154 (1992).
Dale, J.B., et al., "Passive Protection of Mice against Group A Streptococcal Pharyngeal Infection by Lipoteichoic Acid", Journal of Infectious Diseases, 169(2):319-323 (1994).
Dale, J.B., et al., "Recombinant, octavalent group A streptococcal M protein vaccine", Vaccine, 14(10):944-948 (1996).
Dale, J.B., et al., "Hyaluronate capsule and surface M protein in resistance to opsonization of group A streptococci", Infection and Immunity, 64(5):1495-1501 (1996).
Database EMBL "Online", "*Streptococcus* pyogenes M1 GAS", Section 136 of 167 of the complete genome, XP02344849 (Apr. 16, 2001).
Database EMBL "Online", "*Streptococcus* pyogenes M1 GAS", Section 63 of 167 of the complete genome, XP002363053 (Apr. 16, 2001).
Database EMBL EBI: "S. pyogenes protein export PrtM precursor (prtM) gene" database accession No. AF387738 (Jul. 4, 2001).
Davis, L.G., et al., Basic Methods in Molecular Biology, Elsevier Science Publishing Co., Inc. (1986).
Devereux, J., et al., "A comprehensive set of sequence analysis programs for the VAX", Nucleic Acids Research, 12(1):387-395 (1984).
Eddy, S.R., "Hidden Markov models", Cur. Opin. Struct. Bio., 6:361-365 (1996).
Efstratiou, A., et al., "Outbreaks of human infection caused by pyogenic streptococci of Lancefield groups C and G", J. Med. Microbiol., 29(3):207-219 (1989).
Ellen, R.P., et al., "M Protein-Associated Adherence of *Streptococcus* pyogenes to Epithelial Surfaces: Prerequisite for Virulence", Infection and Immunity, 5(5):826-830 (1972).
Eng, J.K., et al., "An Approach to Correlate Tandem Mass Spectral Data of peptides with Amino Acid Sequences in a Protein Database", American Society for Mass Spectrometry, 5:976-989 (1994).
Feldman, C., et al., "Pneumolysin Induces the Salient Histologic Features of Pneumococcal Infection in the Rat Lung In Vivo", Am. J. Respir. Cell. Mol. Biol., 5(5):416-423 (1991).
Feldman, R.G., et al., "Solid-phase antigen density and avidity of antibodies detected in anti-group B streptococcal type III IgG enzyme immunoassays", J. Immunol. Methods, 170:37-45 (1994).
Felgner, P.L., et al., "Lipofection: A highly efficient, lipid-mediated DNA-transfection procedure", Proc. Natl. Acad. Sci. USA, 84:7413-7417 (1987).
Felgner, P.L., et al., "Cationic liposome-mediated transfection", Nature, 337:387-388 (1989).
Ferretti, J.J., et al., "Complete genome sequence of an M1 strain of *Streptococcus* pyogenes", PNAS, 98(8):4658-4663 (2001).
Fischetti, V.A., et al., "Conservation of a hexapeptide sequence in the anchor region of surface proteins from Gram-positive cocci", Molecular Microbiology, 4(9):1603-1605 (1990).
Fogg, G.C., et al., "Constitutive Expression of Fibronectin Binding in *Streptococcus* pyogenes as a Result of Anaerobic Activation of rofA", Journal of Bacteriology, 179(19):6172-6180 (1997).
Foster, T.J., et al., "Surface protein adhesins of Staphylococcus aureus", Trends in Microbiology, 6(12):484-488 (1998).
Fraser, C.M., et al., "Genomic sequence of a Lyme disease spirochaete, Borrelia burgdorferi", Nature, 390:580-586 (1997).
Graham, F.L., et al., "Characteristics of a Human Cell Line Transformed by DNA from Human Adenovirus Type 5", J. Gen. Virol., 36:59-72 (1977).
Graham, F.L., "Covalently closed circles of human adenovirus DNA are infectious", The EMBO Journal, 3(12):2917-2922 (1984).
Gribskov, M., et al., eds., "Sequence Analysis Primer", Stockton Press, New York (1991).
Griffin, H.G., et al., "Chapter 1: Computer Analysis of Sequence Data", Methods in Molecular Biology, Humana Press, New Jersey, pp. 1-8 (1994).
Hacker, J., et al., "Pathogenicity islands of virulent bacteria: structure, function and impact on microbial evolution", Molecular Microbiology, 23(6):1089-1097 (1997).
Hanski, E., et al., "Protein F, a fibronectin-binding protein, is an adhesin of the group A *streptococcus Streptococcus* pyogenes", Proc. Natl. Acad. Sci. USA, 89:6172-6176 (1992).
Hanski, E., et al., "Expression of Protein F, the Fibronectin-Binding protein of *Streptococcus* pyogenes JRS4, in Heterologous Streptococcal and Enterococcal Strains Promotes Their Adherence to Respiratory Epithelial Cells", Infection and Immunity, 60(12):5119-5125 (1992).
Hernandez-Sanchez, J., et al., "A bar minigene-mediated inhibition of protein synthesis involves accumulation of peptidyl-tRNA and starvation for tRNA", The EMBO Journal, 17(13):3758-3765 (1998).
Holmgren, J., et al., "Bacterial Enteric Infections and Vaccine Development", Mucosal Immunology II: Clinical Applications, 21(2):283-302 (1992).
Hope-Simpson, R., "*Streptococcus* Pyogenes in the Throat: A study in a small population, 1962-1975", J. Hyg. Camb., 87(1):109-129 (1981).
Huang, T.-T., "The streptokinase gene of group A streptococci: cloning, expression in *Escherichia coli*, and sequence analysis", Molecular Microbiology, 3(2):197-205 (1989).
Hynes, W.L., et al., "The extracellular hyaluronidase gene (hylA) of *Streptococcus* pyogenes", FEMS Microbiology Letters, 184:109-112 (2000).
Hynes, W.L., et al., "Analysis of a Second Bacteriophage Hyaluronidase Gene from *Streptococcus* pyogenes: Evidence for a Third Hyaluronidase Involved in Extracellular Enzymatic Activity", Infection and Immunity, 63(8):3015-3020 (1995).
International Search Report mailed Jan. 21, 2010 for Int'l Appl. No. PCT/US2009/047886.
International Search Report mailed Jan. 21, 2010 for Int'l Appl. No. PCT/US2009/047902.
Isberg, R.R., et al., "Binding and internalization of microorganisms by integrin receptors", Trends in Microbiology, 2(1):10-14 (1994).
Kafri, T., et al., "A Packaging Cell Line for Lentivirus Vectors", Journal of Virology, 73(1):576-584 (1999).
Kaplitt, M.G., et al., "Expression of a Functional Foreign Gene in Adult Mammalian Brain following in Vivo Transfer via a Herpes Simplex Virus Type 1 Defective Viral Vector", Molecular and Cellular Neurosciences, 2:320-330 (1991).
Kihlberg, B.M., et al., "Protein H, an Antiphagocytic Surface Protein in *Streptococcus* pyogenes", Infection and Immunity, 67(4):1708-1714 (1999).
Koebnik, R., "Proposal for a peptidoglycan-associating alpha-helical motif in the C-terminal regions of some bacterial cell-surface proteins", Molecular Microbiology, 16(6):1269-1270 (1995).
Kohler, G., et al., "Continuous cultures of fused cells secreting antibody of predefined specificity", Nature, 256:495-497 (1975).
Kuo, M.-L., et al., "Efficient Gene Transfer Into Primary Murine Lymphocytes Obviating the Need for Drug Selection", Blood, 82(3):845-852 (1993).
Lazar, E., et al., "Transforming growth factor $\alpha$: Mutation of aspartic acid 47 and leucine 48 results in different biological activities", Mol. Cell. Biol., 8(3):1247-1252 (1988).
Lebkowski, J.S., et al., "Adeno-Associated Virus: a Vector System for Efficient Introduction and Integration of DNA into a Variety of Mammalian Cell Types", Molecular and Cellular Biology, 8(10):3988-3996, (1988).
Lederman, S., et al., "A Single Amino Acid Substitution in a Common African Allele of the CD4 Molecule Ablates Binding of the Monoclonal Antibody, OKT4", Molecular Immunology, 28(11):1171-1181 (1991).
Lesk, A.M., ed., "Computational Molecular Biology: Sources and Methods for Sequence Analysis", Oxford Univ. Press, New York (1988).
Levrero, M., et al., "Defective and nondefective adenovirus vectors for expressing foreign genes in vitro and in vivo", Gene, 101:195-202 (1991).
Li, C.H., et al., "β-Endorphin omission analogs: Dissociation of immunoreactivity from other biological activities", Proc. Natl. Acad. Sci. USA, 77(6):3211-3214 (1980).

(56) References Cited

OTHER PUBLICATIONS

Liu, A.Y., "Chimeric mouse-human IgG1 antibody that can mediate lysis of cancer cells", Proc. Natl. Acad. Sci. USA, 84:3439-3443 (1987).
Loessner, M.J., et al., "Evidence for a Holin-Like protein Gene Fully Embedded Out of Frame in the Endolysin Gene of *Staphylococcus aureus* Bacteriophage 187", 181(15):4452-4460 (1999).
Lukashin, A.V., et al., "GeneMark.hmm: new solutions for gene finding", Nucleic Acids Research, 26(4):1107-1115 (1998).
Lukomski, S., et al., "Extracellular Cysteine Protease Produced by *Streptococcus* pyogenes Participates in the Pathogenesis of Invasive Skin Infection and Dissemination in Mice", Infection and Immunity, 67(4):1779-1788 (1999).
Machy, P., et al., "Gene transfer from targeted liposomes to specific lymphoid cells by electroporation", Proc. Natl. Acad. Sci. USA, 85:8027-8031 (1988).
Mann, R., et al., "Construction of a Retrovirus Packaging Mutant and Its Use to Produce Helper-Free Defective Retrovirus", Cell, 33:153-159 (1983).
Markowitz, D., et al., "A safe packaging line for gene transfer: separating viral genes on two different plasmids", Journal of Virology, 62(4):1120-1124 (1988).
Matsuka, Y.V., et al., "Fibrinogen Cleavage by the *Streptococcus* pyogenes Extracellular Cysteine Protease and Generation of Antibodies That Inhibit Enzyme Proteolytic Activity", Infection and Immunity, 67(9):4326-4333 (1999).
Mazmanian, S.K., et al., "*Staphylococcus aureus* Sortase, an Enzyme that Anchors Surface Proteins to the Cell Wall", 285:760-763 (1999).
McAtee, C.P., et al., "Identification of Potential Diagnostic and Vaccine Candidates of Helicobacter pylori by Two-Dimensional Gel Electrophoresis, Sequence Analysis, and Serum Profiling", Clinical and Diagnostic Laboratory Immunology, 5(4):537-542 (1998).
McAtee, C.P., et al., "Identification of Potential Diagnostic and Vaccine Candidates of Helicobacter pylori by "Proteome" Technologies", Helicobacter, 3(3):163-169 (1998).
McAtee, C.P., et al., "Characterization of a Helicobacter pylori vaccine candidate by proteome techniques", Journal of Chromatography B, 714:325-333 (1998).
McCormick, D., et al., "Human Gene Therapy: The First Round", Nature Biotechnology, 3(8):689-693 (1985).
McGhee, J., et al., "New Perspective in Mucosal Immunity with Emphasis on Vaccine Development", Seminars in Hematology, 30(14):3-15 (1993).
McGhee, J.R., et al., "Mucosal Immunity to Vaccines: Current Concepts for Vaccine Development and Immune Response Analysis", Genetically Engineered Vaccines, J.E. Ciardi et al., eds., Plenum Press, New York, pp. 3-12 (1992).
Mejlhede, N., et al., "Ribosomal—1 Frameshifting during Decoding of *Bacillus subtilis* cdd Occurs at the Sequence CGA AAG", Journal of Bacteriology, 181(9):2930-2937 (1999).
Miller, A.D., et al., "Improved Retroviral Vectors for Gene Transfer and Expression", BioTechniques, 7(9):980-990 (1989).
Mir, L.M., et al., "Long-term, high level in vivo gene expression after electric pulse-mediated gene transfer into skeletal muscle", C.R. Acad. Sci. Paris, Life Sciences, 321:893-899 (1998).
Mitchell, T.J., et al., "Complement activation and antibody binding by pneumolysin via a region of the toxin homologous to a human acute-phase protein", Mol. Microbiol., 5(8):1883-1888 (1991).
MMWR (Morbidity and Mortality Weekly Report), Case Definitions for Infectious Conditions Under Public Health Surveillance, vol. 46, No. RR-10 (May 2, 1997).
Morrison, S.L., et al., "Chimeric human antibody molecules: Mouse antigen-binding domains with human constant region domains", Proc. Natl. Acad. Sci. USA, 81:6851-6855 (1984).
Mountzouros, K.T., et al., "Detection of Complement-Mediated Antibody-Dependent Bactericidal Activity in a Fluorescence-Based Serum Bactericidal Activity in a Fluorescence-Based Serum Bactericidal Assay for Group B *Neisseria meningitidis*", Journal of Clinical Microbiology, 38(8):2878-2884 (2000).
Nakai, K., et al., "Expert system for Predicting Protein Localization Sites in Gram-Negative Bacteria", Proteins: Structure, Function, and Genetics, 11:95-110 (1991).
Naldini, L., "Lentiviruses as gene transfer agents for delivery to non-dividing cells", Current Opinion in Biotechnology, 9:457-463 (1998).
Navarre, W.W., et al., "Surface proteins of Gram-Positive Bacteria and Mechanisms of Their Targeting to the Cell Wall Envelope", Microbiology and Molecular Biology Reviews, 63(1):174-229 (1999).
NCBI Genbank, "zinc ABC transporter, zinc-binding adhesion liprotein [*Streptococcus* agalactiae 2603V/R]", Accession No. NP_687564, accessed Aug. 19, 2010.
NCBI Genbank, "High-affinity zinc uptake system protein znuA precursor [*Streptococcus* pyogenes MGAS10394]", Accession No. AAT86698, accessed Aug. 19, 2010.
NCBI Genbank, "putative protease maturation protein [*Streptococcus* pyogenes]", Accession No. NP_269488, accessed Jun. 27, 2008.
Nielsen, H., et al., "Identification of prokaryotic and eukaryotic signal peptides and prediction of their cleavage sites", Protein Engineering, 10(1):1-6 (1997).
Nizet, V., et al., "Genetic Locus for Streptolysin S Production by Group a *Streptococcus*", Infection and Immunity, 68(7):4245-4254 (2000).
Nordstrand, A., et al., "Allele Substitution of the Streptokinase Gene Reduces the Nephritogenic Capacity of Group A Streptococcal Strain NZ131", Infection and Immunity, 68(3):1019-1025 (2000).
Olmsted, S.B., et al., "High-Resolution Visualization by Field Emission Scanning Electron Microscopy of *Enterococcus faecalis* Surface Proteins Encoded by the Pheromone-Inducible Conjugative Plasmid pCF10", Journal of Bacteriology, 175(19):6229-6237 (1993).
Park, J., et al., "DIVCLUS: an automatic method in the GEANFAMMER package that finds homologous domains in single-and multi-domain proteins", Bioinformatics, 14(2):144-150 (1998).
Parkhill, J., et al., "Complete DNA sequence of a serogroup a strain of *Neisseria meningitidis* Z2491", Nature, 404:502-506 (2000).
Pierschbacher, M.D., et al., "Influence of Sterochemistry of the Sequence Arg-Gly-Asp-Xaa on Binding Specificity in Cell Adhesion", The Journal of Biological Chemistry, 262(36):17294-17298 (1987).
Pizza, M., et al., "Identification of Vaccine Candidates Against Serogroup B Meningococcus by Whole-Genome Sequencing", Science, 287(5459):1816-1820 (2000).
Proft, T., et al., "Identification and Characterization of Novel Superantigens from *Streptococcus* pyogenes", J. Exp. Med., 189(1):89-101 (1999).
Pugsley, A.P., "The Complete General Secretory Pathway in Gram-Negative Bacteria", Microbiological Reviews, 57(1):50-108 (1993).
Quinn, A., et al., "Immunological Relationship between the Class I Epitope of Streptococcal M Protein and Myosin", Infection and Immunity, 66(9):4418-4424 (1998).
Reda, K.B., et al., "Phylogenetic Distribution of Streptococcal Superantigen SSA Allelic Variants Provides Evidence for Horizontal Transfer of SSA within *Streptococcus* pyogenes", Infection and Immunity, 64(4):1161-1165 (1996).
Rudinger, J., "Chapter 1: Characteristics of the amino acids as components of a peptide hormone sequence", Peptide Hormones, J.A. Parsons, ed., University Park Press, 6 pages (1976).
Ruoff, K.L., et al., "Chapter 17: *Streptococcus*", Manual of Clinical Microbiology, P.R. Murray, et al., eds., ASM Press, Washington, DC (7th Ed.), pp. 283-296 (1999).
Sahagan, B.G., et al., "A Genetically Engineered Murine/Human Chimeric Antibody Retains Specificity for Human Tumor-Associated Antigen", The Journal of Immunology, 137(3):1066-1074 (1986).
Salzberg, S.L., et al., "Microbial gene identification using interpolated Markov models", Nucleic Acids Research, 26(2):544-548 (1998).
Sambrook, J., et al., Molecular Cloning: A Laboratory Manual, Cold Spring Harbor Laboratory Press, New York (2nd Ed.), Chapters 9 and 11 (1989).

(56) References Cited

OTHER PUBLICATIONS

Samulski, R.J., et al., "A Recombinant Plasmid from Which an Infectious Adeno-Associated Virus Genome Can Be Excised In Vitro and Its Use to Study Viral Replication", Journal of Virology, 61(10):3096-3101 (1987).
Samulski, R.J., et al., "Helper-Free Stocks of Recombinant Adeno-Associated Viruses: Normal Integration Does Not Require Viral Gene Expression", Journal of Virology, 63(9):3822-3828 (1989).
Scott, T.A., et al., eds., The Concise Encyclopedia: Biochemistry and Molecular Biology (3rd Ed.), Walter de Gruyter Inc., New York, p. 489 (1996).
Seki, Keisuke (Examiner), Japanese Office Action and translation thereof, JP App. No. 2000-586920, 6 pages, mailing date Jun. 28, 2011.
Siezen, R.J., et al., "Homology modeling and protein engineering strategy of subilases, the family of subtilisin-like serine proteinases", Protein Engineering, 4(7):719-737 (1991).
Siezen, R.J., et al., "Subtilases: The superfamily of subtilisin-like serine proteases", Protein Science, 6(3):501-523 (1997).
Smith, D.W., ed., Biocomputing: Informatics and Genome Projects, Academic Press, Inc., New York (1994).
Smoot, J.C., et al., "Genome sequence and comparative microarray analysis of serotype M18 group A *Streptococcus* strains associated with acute rheumatic fever outbreaks", PNAS, 99(7):4668-4673 (2002).
Sonnenberg, M.G., et al., "Definition of Mycobacterium tuberculosis Culture Filtrate Proteins by Two-Dimensional Polyacrylamide Gel Electrophoresis, N-Terminal Amino Acid Sequencing, and Electrospray Mass Spectrometry", Infection and Immunity, 65(11):4515-4524 (1997).
Sonnhammer, E.L.L., et al., "Pfam: A Comprehensive Database of Protein Domain Families Based on Seed Alignments", Proteins: Structure, Function, and Genetics, 28:405-420 (1997).
Springer, T., et al., "Mac-1: a macrophage differentiation antigen Identified by monoclonal antibody", European Journal of Immunology, 9(4):301-306 (1979).
Stafslien, D.K., et al., "Site Directed Mutagenesis of the Streptococcal C5a Peptidase", Abstracts of the 98th General Meeting of the American Society for Microbiology (Atlanta, GA), Abstract B-21, p. 59 (May 17-21, 1998).
Stafslien, D.K., et al., "Characterization of the Streptococcal C5a Peptidase using a C5a-Green Fluorescent Protein Fusion Protein Substrate", Journal of Bacteriology, 182(11):3254-3258 (2000).
Stevens, D.L., "Streptococcal Toxic-Shock Syndrome: Spectrum of Disease, Pathogenesis, and New Concepts in Treatment", Emerg. Infect. Dis., 1(3):69-78 (1995).
Stockbauer, K.E., et al., "A natural variant of the cysteine protease virulence factor of group a *Streptococcus* with an arginine-glycine-aspartic acid (RGD) motif preferentially binds human integrins $\alpha v\beta 3$ and $\alpha IIb\beta 3$", Proc. Natl. Acad. Sci. USA, 96:242-247 (1999).
Stratford-Perricaudet, L.D., et al., "Widespread Long-term Gene Transfer to Mouse Skeletal Muscles and Heart", J. Clin. Invest., 90:626-630 (1992).
Sumby, P., et al., "Evolutionary Origin and Emergence of a Highly Successful Clone of Serotype M1 Group A *Streptococcus* Involved Multiple Horizontal Gene Transfer Events", J. Infect. Dis., 192:771-782 (2005).
Sun, L.K., et al., Chimeric antibody with human constant regions and mouse variable regions directed against carcinoma-associated antigen 17-1A, Proc. Natl. Acad. Sci. USA, 84:214-218 (1987).
Suvorov, A.N., et al., "C5a Peptidase Gene from Group B Streptococci", Genetics and Molecular Biology of Streptococci, Lactococci, and Enterococci, G.M. Dunny, L.L. McKay & P.P. Cleary, eds., American Society for Microbiology, Washington, D.C., pp. 230-232 (1991).
Third Party Observations under Article 115 EPC, European Patent Application No. 02762074.9, published as EP1421098 (WO02/083859), Wyeth, 2 pages (submitted on Jul. 4, 2008).
Ton-That, H., et al., "Purification and characterization of sortase, the transpeptidase that cleaves surface proteins of *Staphylococcus aureus* at the LPXTG motif", PNAS, 96(22):12424-12429 (1999).
Ulmer, J.B., et al., "Heterologous Protection Against Influenza by Injection of DNA Encoding a Viral Protein", Science, 259:1745-1749 (1993).
Von Heijne, G., Sequence Analysis in Molecular Biology: Treasure Trove or Trivial Pursuit, Academic Press, Inc., New York (1987).
Vugia, D.J., et al., "Invasive group a streptococcal infections in children with varicella in Southern California", Pediatr. Infect. Dis. J., 15(2):146-150 (1996).
Wahl, R.L., et al., "Improved Radioimaging and Tumor Localization with Monoclonal F(ab')2", J. Nucl. Med. 24:316-325 (1983).
Weldingh, K., et al., "Two-Dimensional Electrophoresis for Analysis of *Mycobacterium tuberculosis* Culture Filtrate and Purification and Characterization of Six Novel Proteins", Infection and Immunity, 66(8):3492-3500 (1998).
Wessels, M.R., et al., "Critical role of the group a streptococcal capsule in pharyngeal colonization and infection in mice", Proc. Natl. Acad. Sci. USA, 91(25):12238-12242 (1994).
Wexler, D.E., et al., "Mechanism of action of the group a streptococcal C5a inactivator", Proc. Natl. Acad. Sci. USA, 82(23):8144-8148 (1985).
Williams, R.S., et al., "Introduction of foreign genes into tissues of living mice by DNA-coated microprojectiles", Proc. Natl. Acad. Sci. USA, 88:2726-2730 (1991).
Wilson, J.M., et al., "Hepatocyte-directed Gene Transfer in Vivo Leads to Transient Improvement of Hypercholesterolemia in Low Density Lipoprotein Receptor-deficient Rabbits", The Journal of Biological Chemistry, 267(2):963-967 (1992).
Wu, G.Y., et al., "Receptor-mediated in Vitro Gene Transformation by a Soluble DNA Carrier System", The Journal of Biological Chemistry, 262(10):4429-4432 (1987).
Wu, G.Y., et al., "Receptor-mediated Gene Delivery and Expression in Vivo", The Journal of Biological Chemistry, 263(29):14621-14624 (1988).
Yutsudo, T., et al., "The Gene Encoding a New Mitogenic Factor in a *Streptococcus* pyogenes Strain is Distributed Only in Group A Streptococci", Infection and Immunity, 62(9):4000-4004 (1994).
Zufferey, R., et al., "Self-Inactivating Lentivirus Vector for Safe and Efficient In Vivo Gene Delivery", Journal of Virology, 72(12):9873-9880 (1998).

* cited by examiner

Fig. 1

>SPy_2010 |C5A peptidase precursor

TTGCGTAAAAAACAAAAATTACCATTTGATAAACTTGCCATTGCGCTCATGTCTACGAGC
ATCTTGCTCAATGCACAATCAGACATTAAAGCAAATACTGTGACAGAAGACACTCCTGCT
ACCGAACAAGCTGTAGAAACCCCACAACCAACAGCGGTTTCTGAGGAAGCACCATCATCA
AAGGAAACCAAAACCCCACAAACTCCTGATGACGCAGAAGAAACAATAGCAGATGACGCT
AATGATCTAGCCCCTCAAGCTCCTGCTAAAACTGCTGATACACCAGCAACCTCAAAAGCG
ACTATTAGGGATTTGAACGACCCTTCTCAGGTCAAAACCCTGCAGGAAAAAGCAGGCAAA
GGAGCTGGGACTGTTGTTGCAGTGATTGATGCTGGTTTTGATAAAAATCATGAAGCGTGG
CGCTTAACAGACAAAACCAAAGCACGTTACCAATCAAAAGAAGATCTTGAAAAAGCTAAA
AAAGAGCACGGTATTACCTATGGCGAGTGGGTCAATGATAAGGTTGCTTATTACCACGAC
TATAGTAAAGATGGTAAAACCGCTGTCGATCAAGAGCACGGCACACACGTGTCAGGGATC
TTGTCAGGAAATGCTCCATCTGAAACGAAAGAACCTTACCGCCTAGAAGGTGCGATGCCT
GAGGCTCAATTGCTTTTGATGCGTGTCGAAATTGTAAATGGACTAGCAGACTATGCTCGT
AACTACGCTCAAGCTATCATAGATGCTGTCAACTTGGGAGCTAAGGTGATTAATATGAGC
TTTGGTAATGCTGCACTAGCCTATGCCAACCTTCCAGACGAAACCAAAAAAGCCTTTGAC
TATGCCAAATCAAAAGGTGTTAGCATTGTGACCTCAGCTGGTAATGATAGTAGCTTTGGG
GGCAAGACCCGTCTACCTCTAGCAGATCATCCTGATTATGGGGTGGTTGGGACACCTGCA
GCGGCAGACTCAACATTGACAGTTGCTTCTTACAGCCCAGATAAACAGCTCACTGAAACT
GCTACGGTCAAAACAGCCGATCAGCAAGATAAAGAAATGCCTGTTCTTTCAACAAACCGT
TTTGAGCCAAACAAGGCTTACGACTATGCTTATGCTAATCGTGGGATGAAAGAGGATGAT
TTTAAGGATGTCAAAGGTAAGATTGCCCTTATTGAACGTGGCGATATTGATTTCAAAGAT
AAGATTGCAAACGCTAAAAAAGCTGGTGCTGTAGGAGTCTTGATCTATGACAATCAGGAC
AAGGGCTTCCCGATTGAATTGCCAAATGTTGATCAGATGCCTGCGGCCTTTATCAGTCGA
AAAGATGGTCTCTTATTAAAAGAGAATCCCCAAAAAACCATCACCTTCAATGCGACACCT
AAGGTATTGCCAACAGCAAGTGGCACCAAACTAAGCCGCTTCTCAAGCTGGGGTCTGACA
GCTGACGGCAATATTAAGCCAGATATTGCAGCACCCGGCCAAGATATTTTGTCATCAGTG
GCTAACAACAAGTATGCCAAACTTTCTGGAACTAGTATGTCTGCGCCATTAGTAGCGGGT
ATCATGGGACTGTTGCAAAAGCAATATGAGACACAGTATCCTGATATGACACCATCAGAG
CGTCTTGATTTAGCTAAAAAAGTATTGATGAGCTCAGCAACTGCCTTATATGATGAAGAT
GAAAAAGCTTATTTTTCTCCTCGCCAACAAGGAGCAGGAGCAGTCGATGCTAAAAAAGCT
TCAGCAGCAACGATGTATGTGACAGATAAGGATAATACCTCAAGCAAGGTTCACCTGAAC
AATGTTTCTGATAAATTTGAAGTAACAGTAACAGTTCACAACAAATCTGATAAACCTCAA
GAGTTGTATTACCAAGCAACTGTTCAAACAGATAAAGTAGATGGAAAACTCTTTGCCTTG
GCTCCTAAAGCATTGTATGAGACATCATGGCAAAAAATCACAATTCCAGCCAATAGCAGC
AAACAAGTCACCATTCCAATCGATGTTAGTCAATTTAGCAAGGACTTGCTTGCCCCAATG
AAAAATGGCTATTTCTTAGAAGGTTTTGTTCGTTTCAAACAAGATCCTACAAAAGAAGAG
CTTATGAGTATTCCCTATATTGGTTTCCGAGGTGATTTTGGCAATCTGTCAGCCTTAGAA
AAACCAATCTATGATAGCAAAGACGGTAGCAGCTACTATCATGAAGCAAATAGTGATGCC
AAAGACCAATTAGATGGTGATGGATTACAGTTTTACGCTCTGAAAAATAACTTTACAGCA
CTTACTACAGAGTCTAATCCATGGACGATTATTAAAGCTGTCAAAGAAGGGGTTGAAAAC
ATAGAGGATATCGAATCTTCAGAGATCACAGAAACCATTTTTGCAGGTACTTTTGCAAAA
CAAGACGATGATAGCCACTACTATATCCACCGTCACGCTAATGGCAAGCCATATGCTGCG
ATCTCTCCAAATGGGGACGGTAACAGAGATTATGTCCAATTCCAAGGTACTTTCTTGCGT
AATGCTAAAAACCTTGTGGCTGAAGTCTTGGACAAAGAAGGAAATGTTGTTTGGACAAGT
GAGGTAACCGAGCAAGTTGTTAAAAACTACAACAATGACTTGGCAAGCACACTTGGTTCA
ACCCGTTTTGAAAAAACGCGTTGGGACGGTAAAGATAAAGACGGCAAAGTTGTTGCTAAC
GGAACATACACCTATCGTGTTCGCTACACTCCGATTAGCTCAGGTGCAAAAGAACAACAC
ACTGATTTTGATGTGATTGTAGACAATACGACACCTGAAGTCGCAACATCGGCAACATTC
TCAACAGAAGATCGTCGTTTGACACTTGCATCTAAACCAAAAACCAGCCAACCGGTTTAC
CGTGAGCGTATTGCTTACACTTATATGGATGAGGATCTGCCAACAACAGAGTATATTTCT
CCAAATGAAGATGGTACCTTTACTCTTCCTGAAGAGGCTGAAACAATGGAAGGCGCTACT
GTTCCATTGAAAATGTCAGACTTTACTTATGTTGTTGAAGATATGGCTGGTAACATCACT
TATACACCAGTGACTAAGCTATTGGAAGGCCACTCTAATAAACCAGAACAAGACGGTTCA
GATCAAGCACCAGACAAAAAACCAGAAACTAAACCAGAACAAGACGGTTCAGGTCAAGCA

Fig. 1 (continued)

CCAGATAAAAAACCAGAAACTAAACCAGAACAAGACGGTTCAGGTCAAACACCAGACAAA
AAACCAGAAACTAAACCAGAACAAGACGGTTCAGGTCAAACACCAGATAAAAAACCAGAA
ACTAAACCAGAAAAAGATAGTTCAGGTCAAACACCAGGTAAAACTCCTCAAAAAGGTCAA
CCTTCTCGTACTCTAGAGAAACGATCTTCTAAGCGTGCTTTAGCTACAAAAGCATCAACA
AAAGATCAGTTACCAACGACTAATGACAAGGATACAAATCGTTTACATCTCCTTAAGTTA
GTTATGACCACTTTCTTCTTGGGAT

Fig. 2

```
>SPy_2010 |C5A peptidase precursor
LRKKQKLPFDKLAIALMSTSILLNAQSDIKANTVTEDTPATEQAVETPQPTAVSEEAPSS
KETKTPQTPDDAEETIADDANDLAPQAPAKTADTPATSKATIRDLNDPSQVKTLQEKAGK
GAGTVVAVIDAGFDKNHEAWRLTDKTKARYQSKEDLEKAKKEHGITYGEWVNDKVAYYHD
YSKDGKTAVDQEHGTHVSGILSGNAPSETKEPYRLEGAMPEAQLLLMRVEIVNGLADYAR
NYAQAIIDAVNLGAKVINMSFGNAALAYANLPDETKKAFDYAKSKGVSIVTSAGNDSSFG
GKTRLPLADHPDYGVVGTPAAADSTLTVASYSPDKQLTETATVKTADQQDKEMPVLSTNR
FEPNKAYDYAYANRGMKEDDFKDVKGKIALIERGDIDFKDKIANAKKAGAVGVLIYDNQD
KGFPIELPNVDQMPAAFISRKDGLLLKENPQKTITFNATPKVLPTASGTKLSRFSSWGLT
ADGNIKPDIAAPGQDILSSVANNKYAKLSGTSMSAPLVAGIMGLLQKQYETQYPDMTPSE
RLDLAKKVLMSSATALYDEDEKAYFSPRQQGAGAVDAKKASAATMYVTDKDNTSSKVHLN
NVSDKFEVTVTVHNKSDKPQELYYQATVQTDKVDGKLFALAPKALYETSWQKITIPANSS
KQVTIPIDVSQFSKDLLAPMKNGYFLEGFVRFKQDPTKEELMSIPYIGFRGDFGNLSALE
KPIYDSKDGSSYYHEANSDAKDQLDGDGLQFYALKNNFTALTTESNPWTIIKAVKEGVEN
IEDIESSEITETIFAGTFAKQDDDSHYYIHRHANGKPYAAISPNGDGNRDYVQFQGTFLR
NAKNLVAEVLDKEGNVVWTSEVTEQVVKNYNNDLASTLGSTRFEKTRWDGKDKDGKVVAN
GTYTYKVRYTPISSGAKEQHTDFDVIVDNTTPEVATSATFSTEDRRLTLASKPKTSQPVY
RERIAYTYMDEDLPTTEYISPNEDGTFTLPEEAETMEGATVPLKMSDFTYVVEDMAGNIT
YTPVTKLLEGHSNKPEQDGSDQAPDKKPETKPEQDGSGQAPDKKPETKPEQDGSGQTPDK
KPETKPEQDGSGQTPDKKPETKPEKDSSGQTPGKTPQKGQPSRTLEKRSSKRALATKAST
KDQLPTTNDKDTNRLHLLKLVMTTFFLGLVAHIFKTKRTED
```

Fig. 3

```
>SPy_1390 |peptidylprolyl isomerase
ATGAAAAACTCAAATAAACTCATTGCTAGTGTTGTGACATTGGCCTCAGTGATGGCTTTA
GCAGCTTGTCAATCAACTAATGACAATACTAAGGTTATTTCGATGAAAGGTGATACAATT
AGCGTTAGTGATTTTTACAATGAAACAAAAAACACAGAAGTATCGCAAAAAGCGATGCTA
AATCTGGTAATTAGTCGTGTTTTTGAAGCTCAATATGGTGATAAGGTTTCAAAAAAAGAA
GTTGAAAAGGCGTATCATAAAACAGCTGAACAGTATGGCGCTTCATTCTCTGCTGCTTTG
GCACAATCAAGCTTGACACCTGAGACTTTTAAGCGTCAGATCCGCTCTTCAAAATTAGTA
GAATATGCGGTTAAAGAAGCAGCTAAAAAAGAATTGACAACACAAGAATATAAGAAAGCA
TATGAATCTTATACTCCAACAATGGCAGTCGAAATGATTACTTTAGATAATGAAGAGACA
GCTAAATCAGTCTTAGAGGAACTAAAAGCCGAAGGCGCAGACTTTACAGCTATTGCTAAA
GAAAAAACAACAACACCTGAGAAAAAAGTGACCTATAAATTTGATTCAGGTGCGACAAAT
GTACCGACTGATGTCGTAAAAGCGGCTTCAAGTTTGAATGAGGGTGGCATATCAGACGTT
ATCTCGGTTTTAGATCCAACTTCTTATCAAAAGAAGTTTTACATTGTTAAGGTGACTAAA
AAAGCAGAAAAAAAATCAGATTGGCAAGAATATAAGAAACGTTTGAAAGCTATCATTATA
GCTGAAAAATCAAAAGATATGAATTTCCAAAACAAGGTTATTGCAAATGCATTGGATAAA
GCTAATGTAAAAATTAAAGACAAAGCTTTTGCTAATATTTTGGCGCAATATGCAAATCTT
GGTCAAAAAACTAAAGCTGCAAGTGAAAGTTCAACAACCAGCGAATCATCAAAAGCTGCA
GAAGAGAACCCATCAGAATCAGAGCAAACACAGACATCATCAGCTGAAGAACCAACTGAG
ACTGAGGCTCAGACGCAAGAGCCAGCTGCACAATAA
```

Fig. 4

>554 SPy_1390 |peptidylprolyl isomerase
MKNSNKLIASVVTLASVMALAACQSTNDNTKVISMKGDTISVSDFYNETKNTEVSQKAML
NLVISRVFEAQYGDKVSKKEVEKAYHKTAEQYGASFSAALAQSSLTPETFKRQIRSSKLV
EYAVKEAAKKELTTQEYKKAYESYTPTMAVEMITLDNEETAKSVLEELKAEGADFTAIAK
EKTTTPEKKVTYKFDSGATNVPTDVVKAASSLNEGGISDVISVLDPTSYQKKFYIVKVTK
KAEKKSDWQEYKKRLKAIIIAEKSKDMNFQNKVIANALDKANVKIKDKAFANILAQYANL
GQKTKAASEGSTTSESSKAAEENPSESEQTQTSSAEEPTETEAQTQEPAAQ

Fig. 5

>1218 SPy0843||hypothetical protein
ATGAAGAAACATCTTAAAACAGTTGCCTTGACCCTCACTACAGTATCGGTAGTCACCCAC
AATCAGGAAGTTTTTAGTTTAGTCAAAGAGCCAATTCTTAAACAAACTCAAGCTTCTTCA
TCGATTTCTGGCGCTGACTACGCAGAAAGTAGCGGTAAAAGCAAGTTAAAGATTAATGAA
ACTTCTGGCCCTGTTGATGATACAGTCACTGACTTATTTTCGGATAAACGTACTACTCCT
GAAAAAATAAAAGATAATCTTGCTAAAGGTCCGAGAGAACAAGAGTTAAAGGCAGTAACA
GAGAATACAGAATCAGAAAAGCAGATCACTTCTGGATCTCAACTAGAACAATCAAAAGAG
TCTCTTTCTTTAAATAAAACAGTGCCATCAACGTCTAATTGGGAGATTTGTGATTTTATT
ACTAAGGGGAATACCCTTGTTGGTCTTTCAAAATCAGGTGTTGAAAAGTTATCTCAAACT
GATCATCTCGTATTGCCTAGTCAAGCAGCAGATGGAACTCAATTGATACAAGTAGCTAGT
TTTGCTTTTACTCCAGATAAAAAGACGGCAATTGCAGAATATACCAGTAGGGCTGGAGAA
AATGGGGAAATAAGCCAACTAGATGTGGATGGAAAAGAAATTATTAACGAAGGTGAGGTT
TTTAATTCTTATCTACTAAAGAAGGTAACAATCCCAACTGGTTATAAACATATTGGTCAA
GATGCTTTTGTGGACAATAAGAATATTGCTGAGGTTAATCTTCCTGAAAGCCTCGAGACT
ATTTCTGACTATGCTTTTGCTCACCTAGCTTTGAAACAGATCGATTTGCCAGATAATTTA
AAAGCGATTGGAGAATTAGCTTTTTTTGATAATCAAATTACAGGTAAACTTTCTTTGCCA
CGTCAGTTAATGCGATTAGCAGAACGTGCTTTTAAATCAAACCATATCAAAACAATTGAG
TTTAGAGGAAATAGTCTAAAAGTGATAGGGGAAGCTAGTTTTCAAGATAATGATCTGAGT
CAACTAATGCTACCTGACGGTCTTGAAAAAATAGAATCAGAAGCTTTTACAGGAAATCCA
GGAGATGATCACTACAATAACCGTGTTGTTTTGTGGACAAAATCTGGAAAAAATCCTTCT
GGTCTTGCTACTGAAAATACCTATGTTAATCCTGATAAGTCACTATGGCAGGAAAGTCCT
GAGATTGATTATACTAAATGGTTAGAGGAAGATTTTACCTATCAAAAAAATAGTGTTACA
GGTTTTTCAAATAAAGGCTTACAAAAAGTAAAACGTAATAAAAACTTAGAAATTCCAAAA
CAGCACAATGGTGTTACTATTACTGAAATTGGTGATAATGCTTTTCGCAATGTTGATTTT
CAAAATAAAACTTTACGTAAATATGATTTGGAAGAAGTAAAGCTTCCCTCAACTATTCGG
AAAATAGGTGCTTTTGCTTTTCAATCTAATAACTTGAAATCTTTTGAAGCAAGTGACGAT
TTAGAAGAGATTAAAGAGGGAGCCTTTATGAATAATCGTATTGAAACCTTGGAATTAAAA
GATAAATTAGTTACTATTGGTGATGCGGCTTTCCATATTAATCATATTTATGCCATTGTT
CTTCCAGAATCTGTACAAGAAATAGGGCGTTCAGCATTTCGGCAAAATGGTGCAAATAAT
CTTATTTTTATGGGAAGTAAGGTTAAGACCTTAGGTGAGATGGCATTTTTATCAAATAGA
CTTGAACATCTGGATCTTTCTGAGCAAAAACAGTTAACAGAGATTCCTGTTCAAGCCTTT
TCAGACAATGCCTTGAAAGAAGTATTATTACCAGCATCACTGAAAACGATTCGAGAAGAA
GCCTTCAAAAAGAATCATTTAAAACAACTGGAAGTGGCATCTGCCTTGTCCCATATTGCT
TTTAATGCTTTAGATGATAATGATGGTGATGAACAATTTGATAATAAAGTGGTTGTTAAA
ACGCATCATAATTCCTACGCACTAGCAGATGGTGAGCATTTTATCGTTGATCCAGATAAG
TTATCTTCTACAATAGTAGACCTTGAAAAGATTTTAAAACTAATCGAAGGTTTAGATTAT
TCTACATTACGTCAGACTACTCAAACTCAGTTTAGAGACATGACTACTGCAGGTAAAGCG
TTGTTGTCAAAATCTAACCTCCGACAAGGAGAAAAACAAAAATTCCTTCAAGAAGCACAA
TTTTTCCTTGGCCGCGTTGATTTGGATAAAGCCATAGCTAAAGCTGAGAAGGCTTTAGTG
ACCAAGAAGGCAACAAAGAATGGTCAGTTGCTTGAAAGAAGTATTAACAAAGCGGTATTA
GCTTATAATAATAGCGCTATTAAAAAAGCTAATGTTAAGCGCTTGGAAAAAGAGTTAGAC
TTGCTAACAGGATTAGTTGAGGGAAAAGGACCATTAGCGCAAGCTACAATGGTACAAGGA
GTTTATTTATTAAAGACGCCTTTGCCATTGCCAGAATATTATATCGGATTGAACGTTTAT
TTTGACAAGTCTGGAAAATTGATTTATGCACTTGATATGAGTGATACTATTGGCGAGGGA
CAAAAAGACGCTTATGGTAATCCTATATTAAATGTTGACGAGGATAATGAAGGTTATCAT
GCCTTGGCAGTTGCCACTTTAGCTGATTATGAGGGGCTCGACATCAAAACAATTTTAAAT
AGTAAGCTTAGTCAATTAACATCTATTCGTCAGGTACCGACTGCAGCCTATCATAGAGCC
GGTATTTTCCAAGCTATCCAAAATGCAGCGGCAGAAGCAGAGCAGTTATTGCCTAAACCA
GGTACGCACTCTGAGAAGTCAAGCTCAAGTGAATCTGCTAACTCTAAAGATAGAGGATTG
CAATCAAACCCAAAAACGAATAGAGGACGACACTCTGCAATATTGCCTAGGACAGGGTCA
AAAGGCAGCTTTGTCTATGGAATCTTAGGTTACACTAGCGTTGCTTTACTGTCACTAATA
ACTGCTATAAAAAAGAAAAAATATTAA

Fig. 6

```
>1218    SPy0843||hypothetical protein
MKKHLKTVALTLTTVSVVTHNQEVFSLVKEPILKQTQASSSISGADYAESSGKSKLKINE
TSGPVDDTVTDLFSDKRTTPEKIKDNLAKGPREQELKAVTENTESEKQITSGSQLEQSKE
SLSLNKTVPSTSNWEICDFITKGNTLVGLSKSGVEKLSQTDHLVLPSQAADGTQLIQVAS
FAFTPDKKTAIAEYTSRAGENGEISQLDVDGKEIINEGEVFNSYLLKKVTIPTGYKHIGQ
DAFVDNKNIAEVNLPESLETISDYAFAHLALKQIDLPDNLKAIGELAFFDNQITGKLSLP
RQLMRLAERAFKSNHIKTIEFRGNSLKVIGEASFQDNDLSQLMLPDGLEKIESEAFTGNP
GDDHYNNRVVLWTKSGKNPSGLATENTYVNPDKSLWQESPRIDYTKWLEEDFTYQKNSVT
GFSNKGLQKVKRNKNLEIPKQHNGVTITEIGDNAFRNVDFQNKTLRKYDLEEVKLPSTIR
KIGAFAFQSNNLKSFEASDDLEEIKEGAFMNNRIETLELKDKLVTIGDAAFHINHIYAIV
LPESVQEIGRSAFRQNGANNLIFMGSKVKTLGEMAFLSNRLEHLDLSEQKQLTEIPVQAF
SDNALKEVLLPASLKTIREEAFKKNHLKQLEVASALSHIAFNALDDNDGDEQFDNKVVVK
THHNSYALADGEHFIVDPDKLSSTIVDLEKILKLIEGLDYSTLRQTTQTQFRDMTTAGKA
LLSKSNLRQGEKQKFLQEAQFFLGRVDLDKAIAKAEKALVTKKATKNGQLLERSINKAVL
AYNNSAIKKANVKRLEKELDLLTGLVEGKGPLAQATMVQGVYLLKTPLPLPEYYIGLNVY
FDKSGKLIYALDMSDTIGEGQKDAYGNPILNVDEDNEGYHALAVATLADYEGLDIKTILN
SKLSQLTSIRQVPTAAYHRAGIFQAIQNAAAEAEQLLPKPGTHSEKSSSSESANSKDRGL
QSNPKTNRGRHSAILPRTGSKGSFVYGILGYTSVALLSLITAIKKKKY
```

Fig. 7

>1358 SPy_0714 |putative adhesion protein
ATGAAAAAGAAAATTCTTTTAATGATGAGTTTAATCAGTGTCTTTTTTGCTTGGCAACTT
ACTCAGGCAAAACAAGTCTTAGCAGAGGGTAAAGTGAAGGTGGTGACAACTTTCTATCCT
GTTTATGAATTTACAAAAGGGGTTATTGGTAATGATGGCGATGTTTTCATGCTTATGAAA
GCAGGAACGGAACCTCATGATTTTGAGCCTTCTACAAAAGACATTAAAAAAATCCAAGAT
GCAGATGCATTTGTTTATATGGATGACAATATGGAAACTTGGGTTTCTGATGTGAAAAAA
TCATTGACATCTAAAAAAGTGACCATCGTCAAGGGAACTGGTAACATGCTCTTGGTAGCA
GGAGCTGGACATGACCATCCCCATGAGGATGCTGACAAAAAGCATGAGCATAATAAACAT
AGCGAAGAAGGACACAACCATGCTTTTGACCCACACGTGTGGTTGTCACCATACCGTAGC
ATTACAGTCGTTGAAAATATTCGCGACAGTCTTTCAAAAGCTTACCCAGAAAAAGCAGAG
AACTTCAAAGCCAATGCCGCTACTTATATTGAAAAATTAAAAGAGCTTGACAAAGACTAT
ACGGCAGCACTTTCAGATGCTAAGCAAAAGAGCTTTGTGACACAACACGCAGCTTTTGGT
TATATGGCACTTGACTATGGCTTGAACCAAATTTCTATTAATGGTGTCACACCAGATGCA
GAACCATCAGCAAAACGTATTGCTACTTTGTCAAAATACGTTAAAAAATATGGCATCAAA
TACATTTATTTTGAGGAAAATGCGTCAAGTAAAGTCGCAAAAACCCTAGCTAAAGAAGCA
GGAGTTAAAGCGGCTGTGCTTAGTCCGCTTGAAGGTTTGACTGAAAAAGAGATGAAAGCT
GGCCAAGATTACTTTACGGTCATGCGTAAAAACCTTGAAACCTTACGCTTAACCACTGAT
GTGGCTGGTAAAGAAATTCTTCCAGAAAAAGACACGACTAAGACAGTTTACAATGGTTAT
TTCAAAGACAAAGAAGTCAAAGATCGTCAATTATCTGACTGGTCAGGTAGCTGGCAATCT
GTTTACCCCTATCTACAAGATGGTACTTTAGACCAAGTTTGGGACTACAAGGCTAAAAAA
TCTAAAGGTAAAATGACAGCAGCCGAGTACAAAGATTACTACACTACTGGTTATAAAACT
GACGTGGAACAAATCAAAATCAATGGTAAGAAAAAGACCATGACCTTTGTTCGTAATGGT
GAAAAGAAAACCTTCACTTACACATACGCCGGCAAAGAAATCTTGACCTATCCAAAAGGA
AATCGCGGGGTTCGTTTCATGTTTGAAGCTAAAGAAGCAGATGCTGGCGAATTCAAATAC
GTTCAATTCAGTGACCATGCCATTGCTCCTGAAAAAGCAAAGCATTTCCACCTGTACTGG
GGTGGTGACAGCCAAGAAAAATTACATAAAGAGTTAGAACATTGGCCAACTTACTACGGT
TCAGA

Fig. 8

1358 SPy_0714 |putative adhesion protein, SF370

MKKKILLMMSLISVFFAWQLTQAKQVLAEGKVKVVTTFYPVYEFTKQVIGNDGDVFMLMK
AGTEPHDFEPSTKDIKKIQDADAFVYMDDNMETWVSDVKKSLTSKKVTIVKGTGNMLLVA
GAGHDHPHEDADKKHEHNKHSEEGHNHAFDPHVWLSPYRSITVVENIRDSLSKAYPEKAE
NFKANAATYIEKLKELDKDYTAALSDAKQKSFVTQHAAFGYMALDYGLNQISINGVTPDA
EPSAKRIATLSKYVKKYGIKYIYFEENASSKVAKTLAKEAGVKAAVLSPLEGLTEKEMKA
GQDYFTVMRKNLETLRLTTDVAGKEILPEKDTTKTVYNGYFKDKEVKDRQLSDWSGSWQS
VYPYLQDGTLDQVWDYKAKKSKGKMTAAEYKDYYTTGYKTDVEQIKINGKKKTMTFVRNG
EKKTFTYTYAGKEILTYPKGNRGVRFMFEAKEADAGEFKYVQFSDHAIAPEKAKHFHLYW
GGDSQEKLHKELEHWPTYYGSDLSGREIAQEINAH

Fig. 9

>SPy_2000 |surface lipoprotein

GTGTCAAAATACCTAAAATACTTCTCTATTATCACGTTATTTTTGACTGGGCTTATTTTA
GTTGCATGTCAACAACAAAAGCCTCAAACAAAAGAACGTCAGCGCAAACAACGTCCAAAA
GACGAACTTGTCGTTTCTATGGGGGCAAAGCTCCCTCATGAATTCGATCCAAAGGACCGT
TATGGAGTCCACAATGAAGGGAATATCACTCATAGCACTCTATTGAAACGTTCTCCTGAA
CTAGATATAAAAGGAGAGCTTGCTAAAACATACCATCTCTCTGAAGATGGGCTGACTTGG
TCGTTTGACTTGCATGATGATTTTAAATTCTCAAATGGTGAGCCTGTTACTGCTGATGAT
GTTAAGTTTACTTATGATATGTTGAAAGCAGATGGAAAGGCTTGGGATCTAACCTTCATT
AAGAACGTTGAAGTAGTTGGGAAAAATCAGGTCAATATCCATTTGACTGAGGCGCATTCG
ACATTTACAGCACAGTTGACTGAAATCCCAATCGTCCCTAAAAAACATTACAATGATAAG
TATAAGAGCAATCCTATCGGTTCAGGACCTTACATGGTAAAAGAATATAAGGCTGGAGAA
CAAGCTATTTTTGTTCGTAACCCTTATTGGCATGGGAAAAAACCATACTTTAAAAAATGG
ACTTGGGTCTTACTTGATGAAAACACAGCACTAGCAGCTTTAGAATCTGGTGATGTTGAT
ATGATCTACGCAACGCCAGAACTTGCTGATAAAAAAGTCAAAGGCACCCGCCTCCTTGAT
ATTCCATCAAATGATGTGCGCGGCTTATCATTACCTTATGTGAAAAAGGGCGTCATCACT
GATTCTCCTGATGGTTATCCTGTAGGAAATGATGTCACTAGTGATCCAGCAATCCGAAAA
GCCTTGACTATTGGTTTAAATAGGCAAAAAGTTCTCGATACGGTTTTAAATGGTTATGGT
AAACCAGCTTATTCAATTATTGATAAAACACCATTTTGGAATCCAAAAACAGCCATTAAA
GATAATAAAGTAGCTAAAGCTAAGCAATTATTGACAAAAGCGGGATGGAAAGAACAAGCA
GACGGTAGCCGTAAAAAAGGTGACCTTGATGCAGCGTTTGATCTGTACTACCCTACTAAT
GATCAATTGCGAGCGAACTTAGCCGTTGAAGTAGCAGAGCAAGCCAAGGCCCTAGGGATT
ACTATTAAACTCAAAGCTAGTAACTGGGATGAAATGGCAACGAAGTCACATGACTCAGCC
TTACTTTATGCCGGAGGACGTCATCACGCGCAGCAATTTTATGAATCGCATCATCCAAGC
CTAGCAGGGAAAGGTTGGACCAATATTACGTTTTATAACAATCCTACCGTGACTAAGTAC
CTTGACAAAGCAATGACATCTTCTGACCTTGATAAAGCTAACGAATATTGGAAGTTAGCG
CAGTGGGATGGCAAAACAGGTGCTTCTACTCTTGGAGATTTGCCAAATGTATGGTTGGTG
AGCCTTAACCATACTTATATTGGTGATAAACGTATCAATGTAGGTAAACAAGGCGTCCAC
AGTCATGGTCATGATTGGTCATTATTGACTAACATTGCCGAGTGGACTTGGGATGAATCA
ACTAAGTAA

Fig. 10

```
>2459   SPy_2000 |surface lipoprotein
VSKYLKYFSIITLFLTGLILVACQQQKPQTKERQRKQRPKDELVVSMGAKLPHEFDPKDR
YGVHNEGNITHSTLLKRSPELDIKGELAKTYHLSEDGLTWSFDLHDDFKFSNGEPVTADD
VKFTYDMLKADGKAWDLTFIKNVEVVGKNQVNIHLTEAHSTFTAQLTEIPIVPKKHYNDK
YKSNPIGSGPYMVKEYKAGEQAIFVRNPYWHGKKPYFKKWTWVLLDENTALAALESGDVD
MIYATPELADKKVKGTRLLDIPSNDVRGLSLPYVKKGVITDSPDGYPVGNDVTSDPAIRK
ALTIGLNRQKVLDTVLNGYGKPAYSIIDKTPFWNPKTAIKDNKVAKAKQLLTKAGWKEQA
DGSRKKGDLDAAFDLYYPTNDQLRANLAVEVAEQAKALGITIKLKASNWDEMATKSHDSA
LLYAGGRHHAQQFYESHHPSLAGKGWTNITFYNNPTVTKYLDKAMTSSDLDKANEYWKLA
QWDGKTGASTLGDLPNVWLVSLNHTYIGDKRINVGKQGVHSHGHDWSLLTNIAEWTWDES
TK
```

Fig. 11

**%killing of *S. pyogenes* SF370**

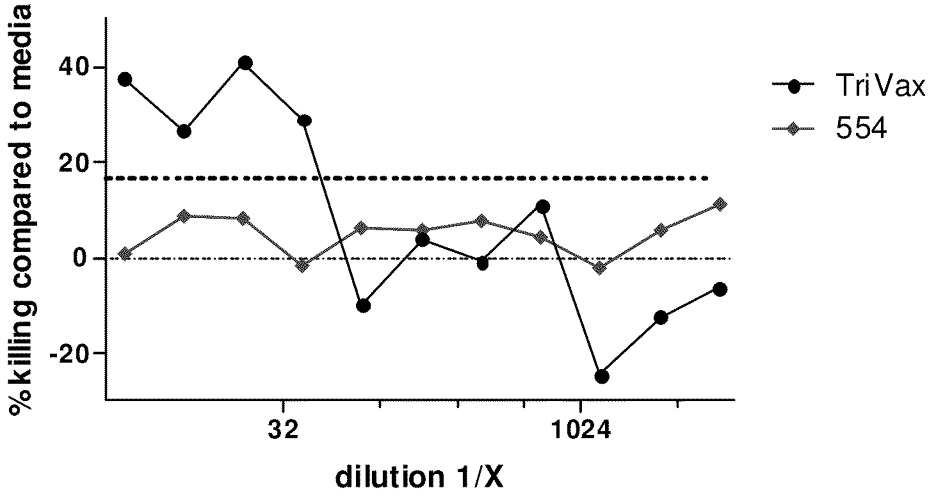

SEQUENCE LISTING

<160> NUMBER OF SEQ ID NOS: 10

<210> SEQ ID NO 1
<211> LENGTH: 3505
<212> TYPE: DNA
<213> ORGANISM: Streptococcus pyogenes

<400> SEQUENCE: 1

```
ttgcgtaaaa aacaaaaatt accatttgat aaacttgcca ttgcgctcat gtctacgagc      60
atcttgctca atgcacaatc agacattaaa gcaaatactg tgacagaaga cactcctgct     120
accgaacaag ctgtagaaac cccacaacca acagcggttt ctgaggaagc accatcatca     180
aaggaaacca aaaccccaca aactcctgat gacgcagaag aaacaatagc agatgacgct     240
aatgatctag cccctcaagc tcctgctaaa actgctgata caccagcaac ctcaaaagcg     300
actattaggg atttgaacga cccttctcag gtcaaaaccc tgcaggaaaa agcaggcaaa     360
ggagctggga ctgttgttgc agtgattgat gctggttttg ataaaaatca tgaagcgtgg     420
cgcttaacag acaaaaccaa agcacgttac caatcaaaag aagatcttga aaaagctaaa     480
aaagagcacg gtattaccta tggcgagtgg gtcaatgata aggttgctta ttaccacgac     540
tatagtaaag atggtaaaac cgctgtcgat caagagcacg gcacacacgt gtcagggatc     600
ttgtcaggaa atgctccatc tgaaacgaaa gaaccttacc gcctagaagg tgcgatgcct     660
gaggctcaat tgcttttgat gcgtgtcgaa attgtaaatg gactagcaga ctatgctcgt     720
aactacgctc aagctatcat agatgctgtc aacttgggag ctaaggtgat taatatgagc     780
tttggtaatg ctgcactagc ctatgccaac cttccagacg aaaccaaaaa agcctttgac     840
tatgccaaat caaaaggtgt tagcattgtg acctcagctg gtaatgatag tagctttggg     900
ggcaagaccc gtctacctct agcagatcat cctgattatg ggtggttggg gacacctgca     960
gcggcagact caacattgac agttgcttct tacagcccag ataaacagct cactgaaact    1020
gctacggtca aaacagccga tcagcaagat aaagaaatgc ctgttcttc aacaaaccgt    1080
tttgagccaa acaaggctta cgactatgct tatgctaatc gtgggatgaa agaggatgat    1140
tttaaggatg tcaaaggtaa gattgccctt attgaacgtg gcgatattga tttcaaagat    1200
aagattgcaa acgctaaaaa agctggtgct gtaggagtct tgatctatga caatcaggac    1260
aagggcttcc cgattgaatt gccaaatgtt gatcagatgc ctgcggcctt tatcagtcga    1320
aaagatggtc tcttattaaa agagaatccc caaaaaacca tcaccttcaa tgcgacacct    1380
aaggtattgc caacagcaag tggcaccaaa ctaagccgct tctcaagctg ggtctgaca     1440
gctgacggca atattaagcc agatattgca gcacccggcc aagatatttt gtcatcagtg    1500
gctaacaaca agtatgccaa actttctgga actagtatgt ctgcgccatt agtagcgggt    1560
atcatgggac tgttgcaaaa gcaatatgag acacagtatc ctgatatgac accatcagag    1620
cgtcttgatt tagctaaaaa agtattgatg agctcagcaa ctgccttata tgatgaagat    1680
gaaaaagctt atttttctcc tcgccaacaa ggagcaggag cagtcgatgc taaaaaagct    1740
tcagcagcaa cgatgtatgt gacagataag gataatacct caagcaaggt tcacctgaac    1800
aatgtttctg ataaatttga agtaacagta acagttcaca acaaatctga taaacctcaa    1860
gagttgtatt accaagcaac tgttcaaaca gataaagtag atggaaaact ctttgccttg    1920
gctcctaaag cattgtatga gacatcatgg caaaaaatca caattccagc caatagcagc    1980
aaacaagtca ccattccaat cgatgttagt caatttagca aggacttgct tgccccaatg    2040
```

-continued

```
aaaaatggct atttcttaga aggttttgtt cgtttcaaac aagatcctac aaaagaagag   2100

cttatgagta ttccctatat tggtttccga ggtgattttg gcaatctgtc agccttagaa   2160

aaaccaatct atgatagcaa agacggtagc agctactatc atgaagcaaa tagtgatgcc   2220

aaagaccaat tagatggtga tggattacag ttttacgctc tgaaaaataa ctttacagca   2280

cttactacag agtctaatcc atggacgatt attaaagctg tcaaagaagg ggttgaaaac   2340

atagaggata tcgaatcttc agagatcaca gaaaccattt ttgcaggtac ttttgcaaaa   2400

caagacgatg atagccacta ctatatccac cgtcacgcta atggcaagcc atatgctgcg   2460

atctctccaa atggggacgg taacagagat tatgtccaat tccaaggtac tttcttgcgt   2520

aatgctaaaa accttgtggc tgaagtcttg gacaaagaag gaaatgttgt ttggacaagt   2580

gaggtaaccg agcaagttgt taaaaactac aacaatgact tggcaagcac acttggttca   2640

acccgttttg aaaaaacgcg ttgggacggt aaagataaag acggcaaagt tgttgctaac   2700

ggaacataca cctatcgtgt tcgctacact ccgattagct caggtgcaaa agaacaacac   2760

actgattttg atgtgattgt agacaatacg acacctgaag tcgcaacatc ggcaacattc   2820

tcaacagaag atcgtcgttt gacacttgca tctaaaccaa aaaccagcca accggtttac   2880

cgtgagcgta ttgcttacac ttatatggat gaggatctgc caacaacaga gtatatttct   2940

ccaaatgaag atggtacctt tactcttcct gaagaggctg aaacaatgga aggcgctact   3000

gttccattga aaatgtcaga ctttacttat gttgttgaag atatggctgg taacatcact   3060

tatacaccag tgactaagct attggaaggc cactctaata aaccagaaca agacggttca   3120

gatcaagcac cagacaaaaa accagaaact aaaccagaac aagacggttc aggtcaagca   3180

ccagataaaa aaccagaaac taaaccagaa caagacggtt caggtcaaac accagacaaa   3240

aaaccagaaa ctaaaccaga acaagacggt tcaggtcaaa caccagataa aaaaccagaa   3300

actaaaccag aaaaagatag ttcaggtcaa acaccaggta aaactcctca aaaaggtcaa   3360

ccttctcgta ctctagagaa acgatcttct aagcgtgctt tagctacaaa agcatcaaca   3420

aaagatcagt taccaacgac taatgacaag gatacaaatc gtttacatct ccttaagtta   3480

gttatgacca ctttcttctt gggat                                          3505
```

<210> SEQ ID NO 2
<211> LENGTH: 1181
<212> TYPE: PRT
<213> ORGANISM: Streptococcus pyogenes

<400> SEQUENCE: 2

```
Leu Arg Lys Lys Gln Lys Leu Pro Phe Asp Lys Leu Ala Ile Ala Leu
1               5                   10                  15

Met Ser Thr Ser Ile Leu Leu Asn Ala Gln Ser Asp Ile Lys Ala Asn
            20                  25                  30

Thr Val Thr Glu Asp Thr Pro Ala Thr Glu Gln Ala Val Glu Thr Pro
        35                  40                  45

Gln Pro Thr Ala Val Ser Glu Glu Ala Pro Ser Ser Lys Glu Thr Lys
    50                  55                  60

Thr Pro Gln Thr Pro Asp Asp Ala Glu Glu Thr Ile Ala Asp Asp Ala
65                  70                  75                  80

Asn Asp Leu Ala Pro Gln Ala Pro Ala Lys Thr Ala Asp Thr Pro Ala
                85                  90                  95

Thr Ser Lys Ala Thr Ile Arg Asp Leu Asn Asp Pro Ser Gln Val Lys
            100                 105                 110

Thr Leu Gln Glu Lys Ala Gly Lys Gly Ala Gly Thr Val Val Ala Val
```

-continued

```
        115                 120                 125

Ile Asp Ala Gly Phe Asp Lys Asn His Glu Ala Trp Arg Leu Thr Asp
    130                 135                 140

Lys Thr Lys Ala Arg Tyr Gln Ser Lys Glu Asp Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Thr Ala Val Asp Gln Glu
            180                 185                 190

His Gly Thr His Val Ser Gly Ile Leu Ser Gly Asn Ala Pro Ser Glu
        195                 200                 205

Thr Lys Glu Pro Tyr Arg Leu Glu Gly Ala Met Pro Glu Ala Gln Leu
    210                 215                 220

Leu Leu Met Arg Val Glu Ile Val Asn Gly Leu Ala Asp Tyr Ala Arg
225                 230                 235                 240

Asn Tyr Ala Gln Ala Ile Ile Asp Ala Val Asn Leu Gly Ala Lys Val
                245                 250                 255

Ile Asn Met Ser Phe Gly Asn Ala Ala Leu Ala Tyr Ala Asn Leu Pro
            260                 265                 270

Asp Glu Thr Lys Lys Ala Phe Asp Tyr Ala Lys Ser Lys Gly Val Ser
        275                 280                 285

Ile Val Thr Ser Ala Gly Asn Asp Ser Ser Phe Gly Gly Lys Thr Arg
    290                 295                 300

Leu Pro Leu Ala Asp His Pro Asp Tyr Gly Val Val Gly Thr Pro Ala
305                 310                 315                 320

Ala Ala Asp Ser Thr Leu Thr Val Ala Ser Tyr Ser Pro Asp Lys Gln
                325                 330                 335

Leu Thr Glu Thr Ala Thr Val Lys Thr Ala Asp Gln Gln Asp Lys Glu
            340                 345                 350

Met Pro Val Leu Ser Thr Asn Arg Phe Glu Pro Asn Lys Ala Tyr Asp
        355                 360                 365

Tyr Ala Tyr Ala Asn Arg Gly Met Lys Glu Asp Asp Phe Lys Asp Val
    370                 375                 380

Lys Gly Lys Ile Ala Leu Ile Glu Arg Gly Asp Ile Asp Phe Lys Asp
385                 390                 395                 400

Lys Ile Ala Asn Ala Lys Lys Ala Gly Ala Val Gly Val Leu Ile Tyr
                405                 410                 415

Asp Asn Gln Asp Lys Gly Phe Pro Ile Glu Leu Pro Asn Val Asp Gln
            420                 425                 430

Met Pro Ala Ala Phe Ile Ser Arg Lys Asp Gly Leu Leu Leu Lys Glu
        435                 440                 445

Asn Pro Gln Lys Thr Ile Thr Phe Asn Ala Thr Pro Lys Val Leu Pro
    450                 455                 460

Thr Ala Ser Gly Thr Lys Leu Ser Arg Phe Ser Ser Trp Gly Leu Thr
465                 470                 475                 480

Ala Asp Gly Asn Ile Lys Pro Asp Ile Ala Ala Pro Gly Gln Asp Ile
                485                 490                 495

Leu Ser Ser Val Ala Asn Asn Lys Tyr Ala Lys Leu Ser Gly Thr Ser
            500                 505                 510

Met Ser Ala Pro Leu Val Ala Gly Ile Met Gly Leu Leu Gln Lys Gln
        515                 520                 525

Tyr Glu Thr Gln Tyr Pro Asp Met Thr Pro Ser Glu Arg Leu Asp Leu
    530                 535                 540
```

-continued

```
Ala Lys Lys Val Leu Met Ser Ser Ala Thr Ala Leu Tyr Asp Glu Asp
545                 550                 555                 560

Glu Lys Ala Tyr Phe Ser Pro Arg Gln Gln Gly Ala Gly Ala Val Asp
                565                 570                 575

Ala Lys Lys Ala Ser Ala Ala Thr Met Tyr Val Thr Asp Lys Asp Asn
            580                 585                 590

Thr Ser Ser Lys Val His Leu Asn Asn Val Ser Asp Lys Phe Glu Val
        595                 600                 605

Thr Val Thr Val His Asn Lys Ser Asp Lys Pro Gln Glu Leu Tyr Tyr
    610                 615                 620

Gln Ala Thr Val Gln Thr Asp Lys Val Asp Gly Lys Leu Phe Ala Leu
625                 630                 635                 640

Ala Pro Lys Ala Leu Tyr Glu Thr Ser Trp Gln Lys Ile Thr Ile Pro
                645                 650                 655

Ala Asn Ser Ser Lys Gln Val Thr Ile Pro Ile Asp Val Ser Gln Phe
            660                 665                 670

Ser Lys Asp Leu Leu Ala Pro Met Lys Asn Gly Tyr Phe Leu Glu Gly
        675                 680                 685

Phe Val Arg Phe Lys Gln Asp Pro Thr Lys Glu Glu Leu Met Ser Ile
    690                 695                 700

Pro Tyr Ile Gly Phe Arg Gly Asp Phe Gly Asn Leu Ser Ala Leu Glu
705                 710                 715                 720

Lys Pro Ile Tyr Asp Ser Lys Asp Gly Ser Ser Tyr Tyr His Glu Ala
                725                 730                 735

Asn Ser Asp Ala Lys Asp Gln Leu Asp Gly Asp Gly Leu Gln Phe Tyr
            740                 745                 750

Ala Leu Lys Asn Asn Phe Thr Ala Leu Thr Thr Glu Ser Asn Pro Trp
        755                 760                 765

Thr Ile Ile Lys Ala Val Lys Glu Gly Val Glu Asn Ile Glu Asp Ile
    770                 775                 780

Glu Ser Ser Glu Ile Thr Glu Thr Ile Phe Ala Gly Thr Phe Ala Lys
785                 790                 795                 800

Gln Asp Asp Asp Ser His Tyr Tyr Ile His Arg His Ala Asn Gly Lys
                805                 810                 815

Pro Tyr Ala Ala Ile Ser Pro Asn Gly Asp Gly Asn Arg Asp Tyr Val
            820                 825                 830

Gln Phe Gln Gly Thr Phe Leu Arg Asn Ala Lys Asn Leu Val Ala Glu
        835                 840                 845

Val Leu Asp Lys Glu Gly Asn Val Val Trp Thr Ser Glu Val Thr Glu
    850                 855                 860

Gln Val Val Lys Asn Tyr Asn Asn Asp Leu Ala Ser Thr Leu Gly Ser
865                 870                 875                 880

Thr Arg Phe Glu Lys Thr Arg Trp Asp Gly Lys Asp Lys Asp Gly Lys
                885                 890                 895

Val Val Ala Asn Gly Thr Tyr Thr Tyr Arg Val Arg Tyr Thr Pro Ile
            900                 905                 910

Ser Ser Gly Ala Lys Glu Gln His Thr Asp Phe Asp Val Ile Val Asp
        915                 920                 925

Asn Thr Thr Pro Glu Val Ala Thr Ser Ala Thr Phe Ser Thr Glu Asp
    930                 935                 940

Arg Arg Leu Thr Leu Ala Ser Lys Pro Lys Thr Ser Gln Pro Val Tyr
945                 950                 955                 960

Arg Glu Arg Ile Ala Tyr Thr Tyr Met Asp Glu Asp Leu Pro Thr Thr
                965                 970                 975
```

-continued

```
Glu Tyr Ile Ser Pro Asn Glu Asp Gly Thr Phe Thr Leu Pro Glu Glu
            980                 985                 990

Ala Glu Thr Met Glu Gly Ala Thr  Val Pro Leu Lys Met  Ser Asp Phe
        995                 1000                1005

Thr Tyr  Val Val Glu Asp Met  Ala Gly Asn Ile Thr  Tyr Thr Pro
    1010                 1015                1020

Val Thr  Lys Leu Leu Glu Gly  His Ser Asn Lys Pro  Glu Gln Asp
    1025                 1030                1035

Gly Ser  Asp Gln Ala Pro Asp  Lys Lys Pro Glu Thr  Lys Pro Glu
    1040                 1045                1050

Gln Asp  Gly Ser Gly Gln Ala  Pro Asp Lys Lys Pro  Glu Thr Lys
    1055                 1060                1065

Pro Glu  Gln Asp Gly Ser Gly  Gln Thr Pro Asp Lys  Lys Pro Glu
    1070                 1075                1080

Thr Lys  Pro Glu Gln Asp Gly  Ser Gly Gln Thr Pro  Asp Lys Lys
    1085                 1090                1095

Pro Glu  Thr Lys Pro Glu Lys  Asp Ser Ser Gly Gln  Thr Pro Gly
    1100                 1105                1110

Lys Thr  Pro Gln Lys Gly Gln  Pro Ser Arg Thr Leu  Glu Lys Arg
    1115                 1120                1125

Ser Ser  Lys Arg Ala Leu Ala  Thr Lys Ala Ser Thr  Lys Asp Gln
    1130                 1135                1140

Leu Pro  Thr Thr Asn Asp Lys  Asp Thr Asn Arg Leu  His Leu Leu
    1145                 1150                1155

Lys Leu  Val Met Thr Thr Phe  Phe Leu Gly Leu Val  Ala His Ile
    1160                 1165                1170

Phe Lys  Thr Lys Arg Thr Glu  Asp
    1175                 1180
```

<210> SEQ ID NO 3
<211> LENGTH: 1056
<212> TYPE: DNA
<213> ORGANISM: Streptococcus pyogenes

<400> SEQUENCE: 3

```
atgaaaaact caaataaact cattgctagt gttgtgacat tggcctcagt gatggcttta     60

gcagcttgtc aatcaactaa tgacaatact aaggttattt cgatgaaagg tgatacaatt    120

agcgttagtg atttttacaa tgaaacaaaa aacacagaag tatcgcaaaa agcgatgcta    180

aatctggtaa ttagtcgtgt ttttgaagct caatatggtg ataaggtttc aaaaaaagaa    240

gttgaaaagg cgtatcataa aacagctgaa cagtatggcg cttcattctc tgctgctttg    300

gcacaatcaa gcttgacacc tgagactttt aagcgtcaga tccgctcttc aaaattagta    360

gaatatgcgg ttaaagaagc agctaaaaaa gaattgacaa cacaagaata taagaaagca    420

tatgaatctt atactccaac aatggcagtc gaaatgatta ctttagataa tgaagagaca    480

gctaaatcag tcttagagga actaaaagcc gaaggcgcag actttacagc tattgctaaa    540

gaaaaaacaa caacacctga gaaaaaagtg acctataaat ttgattcagg tgcgacaaat    600

gtaccgactg atgtcgtaaa agcggcttca agtttgaatg agggtggcat atcagacgtt    660

atctcggttt tagatccaac ttcttatcaa aagaagtttt acattgttaa ggtgactaaa    720

aaagcagaaa aaaaatcaga ttggcaagaa tataagaaac gtttgaaagc tatcattata    780

gctgaaaaat caaaagatat gaatttccaa aacaaggtta ttgcaaatgc attggataaa    840

gctaatgtaa aaattaaaga caaagctttt gctaatattt tggcgcaata tgcaaatctt    900
```

```
ggtcaaaaaa ctaaagctgc aagtgaaagt tcaacaacca gcgaatcatc aaaagctgca    960

gaagagaacc catcagaatc agagcaaaca cagacatcat cagctgaaga accaactgag   1020

actgaggctc agacgcaaga gccagctgca caataa                             1056


<210> SEQ ID NO 4
<211> LENGTH: 351
<212> TYPE: PRT
<213> ORGANISM: Streptococcus pyogenes

<400> SEQUENCE: 4

Met Lys Asn Ser Asn Lys Leu Ile Ala Ser Val Val Thr Leu Ala Ser
1               5                   10                  15

Val Met Ala Leu Ala Ala Cys Gln Ser Thr Asn Asp Asn Thr Lys Val
            20                  25                  30

Ile Ser Met Lys Gly Asp Thr Ile Ser Val Ser Asp Phe Tyr Asn Glu
        35                  40                  45

Thr Lys Asn Thr Glu Val Ser Gln Lys Ala Met Leu Asn Leu Val Ile
    50                  55                  60

Ser Arg Val Phe Glu Ala Gln Tyr Gly Asp Lys Val Ser Lys Lys Glu
65                  70                  75                  80

Val Glu Lys Ala Tyr His Lys Thr Ala Glu Gln Tyr Gly Ala Ser Phe
                85                  90                  95

Ser Ala Ala Leu Ala Gln Ser Ser Leu Thr Pro Glu Thr Phe Lys Arg
            100                 105                 110

Gln Ile Arg Ser Ser Lys Leu Val Glu Tyr Ala Val Lys Glu Ala Ala
        115                 120                 125

Lys Lys Glu Leu Thr Thr Gln Glu Tyr Lys Lys Ala Tyr Glu Ser Tyr
    130                 135                 140

Thr Pro Thr Met Ala Val Glu Met Ile Thr Leu Asp Asn Glu Glu Thr
145                 150                 155                 160

Ala Lys Ser Val Leu Glu Glu Leu Lys Ala Glu Gly Ala Asp Phe Thr
                165                 170                 175

Ala Ile Ala Lys Glu Lys Thr Thr Thr Pro Glu Lys Lys Val Thr Tyr
            180                 185                 190

Lys Phe Asp Ser Gly Ala Thr Asn Val Pro Thr Asp Val Val Lys Ala
        195                 200                 205

Ala Ser Ser Leu Asn Glu Gly Gly Ile Ser Asp Val Ile Ser Val Leu
    210                 215                 220

Asp Pro Thr Ser Tyr Gln Lys Lys Phe Tyr Ile Val Lys Val Thr Lys
225                 230                 235                 240

Lys Ala Glu Lys Lys Ser Asp Trp Gln Glu Tyr Lys Lys Arg Leu Lys
                245                 250                 255

Ala Ile Ile Ile Ala Glu Lys Ser Lys Asp Met Asn Phe Gln Asn Lys
            260                 265                 270

Val Ile Ala Asn Ala Leu Asp Lys Ala Asn Val Lys Ile Lys Asp Lys
        275                 280                 285

Ala Phe Ala Asn Ile Leu Ala Gln Tyr Ala Asn Leu Gly Gln Lys Thr
    290                 295                 300

Lys Ala Ala Ser Glu Ser Ser Thr Thr Ser Glu Ser Ser Lys Ala Ala
305                 310                 315                 320

Glu Glu Asn Pro Ser Glu Ser Glu Gln Thr Gln Thr Ser Ser Ala Glu
                325                 330                 335

Glu Pro Thr Glu Thr Glu Ala Gln Thr Gln Glu Pro Ala Ala Gln
            340                 345                 350
```

<210> SEQ ID NO 5
<211> LENGTH: 3027
<212> TYPE: DNA
<213> ORGANISM: Streptococcus pyogenes

<400> SEQUENCE: 5
atgaagaaac atcttaaaac agttgccttg accctcacta cagtatcggt agtcacccac 60
aatcaggaag tttttagttt agtcaaagag ccaattctta aacaaactca agcttcttca 120
tcgatttctg gcgctgacta cgcagaaagt agcggtaaaa gcaagttaaa gattaatgaa 180
acttctggcc ctgttgatga tacagtcact gacttatttt cggataaacg tactactcct 240
gaaaaaataa aagataatct tgctaaaggt ccgagagaac aagagttaaa ggcagtaaca 300
gagaatacag aatcagaaaa gcagatcact tctggatctc aactagaaca atcaaaagag 360
tctctttctt taaataaaac agtgccatca acgtctaatt gggagatttg tgattttatt 420
actaagggga ataccccttgt tggtctttca aaatcaggtg ttgaaaagtt atctcaaact 480
gatcatctcg tattgcctag tcaagcagca gatggaactc aattgataca agtagctagt 540
tttgctttta ctccagataa aaagacggca attgcagaat ataccagtag ggctggagaa 600
aatggggaaa taagccaact agatgtggat ggaaaagaaa ttattaacga aggtgaggtt 660
tttaattctt atctactaaa gaaggtaaca atcccaactg gttataaaca tattggtcaa 720
gatgcttttg tggacaataa gaatattgct gaggttaatc ttcctgaaag cctcgagact 780
atttctgact atgcttttgc tcacctagct ttgaaacaga tcgatttgcc agataattta 840
aaagcgattg gagaattagc tttttttgat aatcaaatta caggtaaact ttctttgcca 900
cgtcagttaa tgcgattagc agaacgtgct tttaaatcaa accatatcaa aacaattgag 960
tttagaggaa atagtctaaa agtgataggg gaagctagtt ttcaagataa tgatctgagt 1020
caactaatgc tacctgacgg tcttgaaaaa atagaatcag aagcttttac aggaaatcca 1080
ggagatgatc actacaataa ccgtgttgtt ttgtggacaa aatctggaaa aaatccttct 1140
ggtcttgcta ctgaaaatac ctatgttaat cctgataagt cactatggca ggaaagtcct 1200
gagattgatt atactaaatg gttagaggaa gattttacct atcaaaaaaa tagtgttaca 1260 ggttttttcaa ataaaggctt acaaaaagta aaacgtaata aaaacttaga aattccaaaa 1320
cagcacaatg gtgttactat tactgaaatt ggtgataatg cttttcgcaa tgttgatttt 1380
caaaataaaa ctttacgtaa atatgatttg gaagaagtaa agcttccctc aactattcgg 1440
aaaataggtg cttttgcttt tcaatctaat aacttgaaat cttttgaagc aagtgacgat 1500
ttagaagaga ttaaagaggg agcctttatg aataatcgta ttgaaacctt ggaattaaaa 1560
gataaattag ttactattgg tgatgcggct ttccatatta atcatattta tgccattgtt 1620
cttccagaat ctgtacaaga aatagggcgt tcagcatttc ggcaaaatgg tgcaaataat 1680
cttattttta tgggaagtaa ggttaagacc ttaggtgaga tggcattttt atcaaataga 1740
cttgaacatc tggatctttc tgagcaaaaa cagttaacag agattcctgt tcaagccttt 1800
tcagacaatg ccttgaaaga agtattatta ccagcatcac tgaaaacgat tcgagaagaa 1860
gccttcaaaa agaatcattt aaaacaactg gaagtggcat ctgccttgtc ccatattgct 1920
tttaatgctt tagatgataa tgatggtgat gaacaatttg ataataaagt ggttgttaaa 1980
acgcatcata attcctacgc actagcagat ggtgagcatt ttatcgttga tccagataag 2040
ttatcttcta caatagtaga ccttgaaaag attttaaaac taatcgaagg tttagattat 2100
tctacattac gtcagactac tcaaactcag tttagagaca tgactactgc aggtaaagcg 2160

```
ttgttgtcaa aatctaacct ccgacaagga gaaaaacaaa aattccttca agaagcacaa   2220

tttttccttg gccgcgttga tttggataaa gccatagcta aagctgagaa ggctttagtg   2280

accaagaagg caacaaagaa tggtcagttg cttgaaagaa gtattaacaa agcggtatta   2340

gcttataata atagcgctat taaaaaagct aatgttaagc gcttggaaaa agagttagac   2400

ttgctaacag gattagttga gggaaaagga ccattagcgc aagctacaat ggtacaagga   2460

gtttatttat taaagacgcc tttgccattg ccagaatatt atatcggatt gaacgtttat   2520

tttgacaagt ctggaaaatt gatttatgca cttgatatga gtgatactat tggcgaggga   2580

caaaaagacg cttatggtaa tcctatatta aatgttgacg aggataatga aggttatcat   2640

gccttggcag ttgccacttt agctgattat gaggggctcg acatcaaaac aattttaaat   2700

agtaagctta gtcaattaac atctattcgt caggtaccga ctgcagccta tcatagagcc   2760

ggtattttcc aagctatcca aaatgcagcg gcagaagcag agcagttatt gcctaaacca   2820

ggtacgcact ctgagaagtc aagctcaagt gaatctgcta actctaaaga tagaggattg   2880

caatcaaacc caaaaacgaa tagaggacga cactctgcaa tattgcctag gacagggtca   2940

aaaggcagct ttgtctatgg aatcttaggt tacactagcg ttgctttact gtcactaata   3000

actgctataa aaaagaaaaa atattaa                                       3027
```

<210> SEQ ID NO 6
<211> LENGTH: 1008
<212> TYPE: PRT
<213> ORGANISM: Streptococcus pyogenes

<400> SEQUENCE: 6

```
Met Lys Lys His Leu Lys Thr Val Ala Leu Thr Leu Thr Thr Val Ser
1               5                   10                  15

Val Val Thr His Asn Gln Glu Val Phe Ser Leu Val Lys Glu Pro Ile
            20                  25                  30

Leu Lys Gln Thr Gln Ala Ser Ser Ser Ile Ser Gly Ala Asp Tyr Ala
        35                  40                  45

Glu Ser Ser Gly Lys Ser Lys Leu Lys Ile Asn Glu Thr Ser Gly Pro
    50                  55                  60

Val Asp Asp Thr Val Thr Asp Leu Phe Ser Asp Lys Arg Thr Thr Pro
65                  70                  75                  80

Glu Lys Ile Lys Asp Asn Leu Ala Lys Gly Pro Arg Glu Gln Glu Leu
                85                  90                  95

Lys Ala Val Thr Glu Asn Thr Glu Ser Glu Lys Gln Ile Thr Ser Gly
            100                 105                 110

Ser Gln Leu Glu Gln Ser Lys Glu Ser Leu Ser Leu Asn Lys Thr Val
        115                 120                 125

Pro Ser Thr Ser Asn Trp Glu Ile Cys Asp Phe Ile Thr Lys Gly Asn
    130                 135                 140

Thr Leu Val Gly Leu Ser Lys Ser Gly Val Glu Lys Leu Ser Gln Thr
145                 150                 155                 160

Asp His Leu Val Leu Pro Ser Gln Ala Ala Asp Gly Thr Gln Leu Ile
                165                 170                 175

Gln Val Ala Ser Phe Ala Phe Thr Pro Asp Lys Lys Thr Ala Ile Ala
            180                 185                 190

Glu Tyr Thr Ser Arg Ala Gly Glu Asn Gly Glu Ile Ser Gln Leu Asp
        195                 200                 205

Val Asp Gly Lys Glu Ile Ile Asn Glu Gly Glu Val Phe Asn Ser Tyr
    210                 215                 220
```

-continued

```
Leu Leu Lys Lys Val Thr Ile Pro Thr Gly Tyr Lys His Ile Gly Gln
225                 230                 235                 240

Asp Ala Phe Val Asp Asn Lys Asn Ile Ala Glu Val Asn Leu Pro Glu
                245                 250                 255

Ser Leu Glu Thr Ile Ser Asp Tyr Ala Phe Ala His Leu Ala Leu Lys
            260                 265                 270

Gln Ile Asp Leu Pro Asp Asn Leu Lys Ala Ile Gly Glu Leu Ala Phe
        275                 280                 285

Phe Asp Asn Gln Ile Thr Gly Lys Leu Ser Leu Pro Arg Gln Leu Met
    290                 295                 300

Arg Leu Ala Glu Arg Ala Phe Lys Ser Asn His Ile Lys Thr Ile Glu
305                 310                 315                 320

Phe Arg Gly Asn Ser Leu Lys Val Ile Gly Glu Ala Ser Phe Gln Asp
                325                 330                 335

Asn Asp Leu Ser Gln Leu Met Leu Pro Asp Gly Leu Glu Lys Ile Glu
            340                 345                 350

Ser Glu Ala Phe Thr Gly Asn Pro Gly Asp Asp His Tyr Asn Asn Arg
        355                 360                 365

Val Val Leu Trp Thr Lys Ser Gly Lys Asn Pro Ser Gly Leu Ala Thr
    370                 375                 380

Glu Asn Thr Tyr Val Asn Pro Asp Lys Ser Leu Trp Gln Glu Ser Pro
385                 390                 395                 400

Glu Ile Asp Tyr Thr Lys Trp Leu Glu Glu Asp Phe Thr Tyr Gln Lys
                405                 410                 415

Asn Ser Val Thr Gly Phe Ser Asn Lys Gly Leu Gln Lys Val Lys Arg
            420                 425                 430

Asn Lys Asn Leu Glu Ile Pro Lys Gln His Asn Gly Val Thr Ile Thr
        435                 440                 445

Glu Ile Gly Asp Asn Ala Phe Arg Asn Val Asp Phe Gln Asn Lys Thr
    450                 455                 460

Leu Arg Lys Tyr Asp Leu Glu Glu Val Lys Leu Pro Ser Thr Ile Arg
465                 470                 475                 480

Lys Ile Gly Ala Phe Ala Phe Gln Ser Asn Asn Leu Lys Ser Phe Glu
                485                 490                 495

Ala Ser Asp Asp Leu Glu Glu Ile Lys Glu Gly Ala Phe Met Asn Asn
            500                 505                 510

Arg Ile Glu Thr Leu Glu Leu Lys Asp Lys Leu Val Thr Ile Gly Asp
        515                 520                 525

Ala Ala Phe His Ile Asn His Ile Tyr Ala Ile Val Leu Pro Glu Ser
    530                 535                 540

Val Gln Glu Ile Gly Arg Ser Ala Phe Arg Gln Asn Gly Ala Asn Asn
545                 550                 555                 560

Leu Ile Phe Met Gly Ser Lys Val Lys Thr Leu Gly Glu Met Ala Phe
                565                 570                 575

Leu Ser Asn Arg Leu Glu His Leu Asp Leu Ser Glu Gln Lys Gln Leu
            580                 585                 590

Thr Glu Ile Pro Val Gln Ala Phe Ser Asp Asn Ala Leu Lys Glu Val
        595                 600                 605

Leu Leu Pro Ala Ser Leu Lys Thr Ile Arg Glu Glu Ala Phe Lys Lys
    610                 615                 620

Asn His Leu Lys Gln Leu Glu Val Ala Ser Ala Leu Ser His Ile Ala
625                 630                 635                 640

Phe Asn Ala Leu Asp Asp Asn Asp Gly Asp Glu Gln Phe Asp Asn Lys
```

```
                645                 650                 655

Val Val Val Lys Thr His His Asn Ser Tyr Ala Leu Ala Asp Gly Glu
            660                 665                 670

His Phe Ile Val Asp Pro Asp Lys Leu Ser Ser Thr Ile Val Asp Leu
        675                 680                 685

Glu Lys Ile Leu Lys Leu Ile Glu Gly Leu Asp Tyr Ser Thr Leu Arg
    690                 695                 700

Gln Thr Thr Gln Thr Gln Phe Arg Asp Met Thr Thr Ala Gly Lys Ala
705                 710                 715                 720

Leu Leu Ser Lys Ser Asn Leu Arg Gln Gly Glu Lys Gln Lys Phe Leu
                725                 730                 735

Gln Glu Ala Gln Phe Phe Leu Gly Arg Val Asp Leu Asp Lys Ala Ile
            740                 745                 750

Ala Lys Ala Glu Lys Ala Leu Val Thr Lys Lys Ala Thr Lys Asn Gly
        755                 760                 765

Gln Leu Leu Glu Arg Ser Ile Asn Lys Ala Val Leu Ala Tyr Asn Asn
    770                 775                 780

Ser Ala Ile Lys Lys Ala Asn Val Lys Arg Leu Glu Lys Glu Leu Asp
785                 790                 795                 800

Leu Leu Thr Gly Leu Val Glu Gly Lys Gly Pro Leu Ala Gln Ala Thr
                805                 810                 815

Met Val Gln Gly Val Tyr Leu Leu Lys Thr Pro Leu Pro Leu Pro Glu
            820                 825                 830

Tyr Tyr Ile Gly Leu Asn Val Tyr Phe Asp Lys Ser Gly Lys Leu Ile
        835                 840                 845

Tyr Ala Leu Asp Met Ser Asp Thr Ile Gly Glu Gly Gln Lys Asp Ala
    850                 855                 860

Tyr Gly Asn Pro Ile Leu Asn Val Asp Glu Asp Asn Glu Gly Tyr His
865                 870                 875                 880

Ala Leu Ala Val Ala Thr Leu Ala Asp Tyr Glu Gly Leu Asp Ile Lys
                885                 890                 895

Thr Ile Leu Asn Ser Lys Leu Ser Gln Leu Thr Ser Ile Arg Gln Val
            900                 905                 910

Pro Thr Ala Ala Tyr His Arg Ala Gly Ile Phe Gln Ala Ile Gln Asn
        915                 920                 925

Ala Ala Ala Glu Ala Glu Gln Leu Leu Pro Lys Pro Gly Thr His Ser
    930                 935                 940

Glu Lys Ser Ser Ser Ser Glu Ser Ala Asn Ser Lys Asp Arg Gly Leu
945                 950                 955                 960

Gln Ser Asn Pro Lys Thr Asn Arg Gly Arg His Ser Ala Ile Leu Pro
                965                 970                 975

Arg Thr Gly Ser Lys Gly Ser Phe Val Tyr Gly Ile Leu Gly Tyr Thr
            980                 985                 990

Ser Val Ala Leu Leu Ser Leu Ile  Thr Ala Ile Lys Lys  Lys Lys Tyr
        995                 1000                1005


<210> SEQ ID NO 7
<211> LENGTH: 1505
<212> TYPE: DNA
<213> ORGANISM: Streptococcus pyogenes

<400> SEQUENCE: 7

atgaaaaaga aaattctttt aatgatgagt ttaatcagtg tctttttgc ttggcaactt     60

actcaggcaa aacaagtctt agcagagggt aaagtgaagg tggtgacaac tttctatcct    120
```

```
gtttatgaat ttacaaaagg ggttattggt aatgatggcg atgttttcat gcttatgaaa    180

gcaggaacgg aacctcatga ttttgagcct tctacaaaag acattaaaaa aatccaagat    240

gcagatgcat ttgtttatat ggatgacaat atggaaactt gggtttctga tgtgaaaaaa    300

tcattgacat ctaaaaaagt gaccatcgtc aagggaactg gtaacatgct cttggtagca    360

ggagctggac atgaccatcc ccatgaggat gctgacaaaa agcatgagca taataaacat    420

agcgaagaag gacacaacca tgcttttgac ccacacgtgt ggttgtcacc ataccgtagc    480

attacagtcg ttgaaaatat tcgcgacagt ctttcaaaag cttacccaga aaaagcagag    540

aacttcaaag ccaatgccgc tacttatatt gaaaaattaa aagagcttga caaagactat    600

acggcagcac tttcagatgc taagcaaaag agctttgtga cacaacacgc agcttttggt    660

tatatggcac ttgactatgg cttgaaccaa atttctatta atggtgtcac accagatgca    720

gaaccatcag caaaacgtat tgctactttg tcaaaatacg ttaaaaaata tggcatcaaa    780

tacatttatt ttgaggaaaa tgcgtcaagt aaagtcgcaa aaaccctagc taaagaagca    840

ggagttaaag cggctgtgct tagtccgctt gaaggtttga ctgaaaaaga gatgaaagct    900

ggccaagatt actttacggt catgcgtaaa aaccttgaaa ccttacgctt aaccactgat    960

gtggctggta aagaaattct tccagaaaaa gacacgacta agacagttta caatggttat   1020

ttcaaagaca aagaagtcaa agatcgtcaa ttatctgact ggtcaggtag ctggcaatct   1080

gtttacccct atctacaaga tggtacttta gaccaagttt gggactacaa ggctaaaaaa   1140

tctaaaggta aaatgacagc agccgagtac aaagattact acactactgg ttataaaact   1200

gacgtggaac aaatcaaaat caatggtaag aaaaagacca tgacctttgt tcgtaatggt   1260

gaaaagaaaa ccttcactta cacatacgcc ggcaaagaaa tcttgaccta tccaaaagga   1320

aatcgcgggg ttcgtttcat gtttgaagct aaagaagcag atgctggcga attcaaatac   1380

gttcaattca gtgaccatgc cattgctcct gaaaaagcaa agcatttcca cctgtactgg   1440

ggtggtgaca gccaagaaaa attacataaa gagttagaac attggccaac ttactacggt   1500

tcaga                                                               1505
```

```
<210> SEQ ID NO 8
<211> LENGTH: 515
<212> TYPE: PRT
<213> ORGANISM: Streptococcus pyogenes

<400> SEQUENCE: 8

Met Lys Lys Lys Ile Leu Leu Met Met Ser Leu Ile Ser Val Phe Phe
1               5                   10                  15

Ala Trp Gln Leu Thr Gln Ala Lys Gln Val Leu Ala Glu Gly Lys Val
            20                  25                  30

Lys Val Val Thr Thr Phe Tyr Pro Val Tyr Glu Phe Thr Lys Gly Val
        35                  40                  45

Ile Gly Asn Asp Gly Asp Val Phe Met Leu Met Lys Ala Gly Thr Glu
    50                  55                  60

Pro His Asp Phe Glu Pro Ser Thr Lys Asp Ile Lys Lys Ile Gln Asp
65                  70                  75                  80

Ala Asp Ala Phe Val Tyr Met Asp Asp Asn Met Glu Thr Trp Val Ser
                85                  90                  95

Asp Val Lys Lys Ser Leu Thr Ser Lys Lys Val Thr Ile Val Lys Gly
            100                 105                 110

Thr Gly Asn Met Leu Leu Val Ala Gly Ala Gly His Asp His Pro His
        115                 120                 125
```

```
Glu Asp Ala Asp Lys Lys His Glu His Asn Lys His Ser Glu Glu Gly
    130                 135                 140

His Asn His Ala Phe Asp Pro His Val Trp Leu Ser Pro Tyr Arg Ser
145                 150                 155                 160

Ile Thr Val Val Glu Asn Ile Arg Asp Ser Leu Ser Lys Ala Tyr Pro
                165                 170                 175

Glu Lys Ala Glu Asn Phe Lys Ala Asn Ala Ala Thr Tyr Ile Glu Lys
            180                 185                 190

Leu Lys Glu Leu Asp Lys Asp Tyr Thr Ala Ala Leu Ser Asp Ala Lys
        195                 200                 205

Gln Lys Ser Phe Val Thr Gln His Ala Ala Phe Gly Tyr Met Ala Leu
    210                 215                 220

Asp Tyr Gly Leu Asn Gln Ile Ser Ile Asn Gly Val Thr Pro Asp Ala
225                 230                 235                 240

Glu Pro Ser Ala Lys Arg Ile Ala Thr Leu Ser Lys Tyr Val Lys Lys
                245                 250                 255

Tyr Gly Ile Lys Tyr Ile Tyr Phe Glu Glu Asn Ala Ser Ser Lys Val
            260                 265                 270

Ala Lys Thr Leu Ala Lys Glu Ala Gly Val Lys Ala Ala Val Leu Ser
        275                 280                 285

Pro Leu Glu Gly Leu Thr Glu Lys Glu Met Lys Ala Gly Gln Asp Tyr
    290                 295                 300

Phe Thr Val Met Arg Lys Asn Leu Glu Thr Leu Arg Leu Thr Thr Asp
305                 310                 315                 320

Val Ala Gly Lys Glu Ile Leu Pro Glu Lys Asp Thr Thr Lys Thr Val
                325                 330                 335

Tyr Asn Gly Tyr Phe Lys Asp Lys Glu Val Lys Asp Arg Gln Leu Ser
            340                 345                 350

Asp Trp Ser Gly Ser Trp Gln Ser Val Tyr Pro Tyr Leu Gln Asp Gly
        355                 360                 365

Thr Leu Asp Gln Val Trp Asp Tyr Lys Ala Lys Lys Ser Lys Gly Lys
    370                 375                 380

Met Thr Ala Ala Glu Tyr Lys Asp Tyr Tyr Thr Thr Gly Tyr Lys Thr
385                 390                 395                 400

Asp Val Glu Gln Ile Lys Ile Asn Gly Lys Lys Lys Thr Met Thr Phe
                405                 410                 415

Val Arg Asn Gly Glu Lys Lys Thr Phe Thr Tyr Thr Tyr Ala Gly Lys
            420                 425                 430

Glu Ile Leu Thr Tyr Pro Lys Gly Asn Arg Gly Val Arg Phe Met Phe
        435                 440                 445

Glu Ala Lys Glu Ala Asp Ala Gly Glu Phe Lys Tyr Val Gln Phe Ser
    450                 455                 460

Asp His Ala Ile Ala Pro Glu Lys Ala Lys His Phe His Leu Tyr Trp
465                 470                 475                 480

Gly Gly Asp Ser Gln Glu Lys Leu His Lys Glu Leu Glu His Trp Pro
                485                 490                 495

Thr Tyr Tyr Gly Ser Asp Leu Ser Gly Arg Glu Ile Ala Gln Glu Ile
            500                 505                 510

Asn Ala His
        515
```

<210> SEQ ID NO 9
<211> LENGTH: 1629
<212> TYPE: DNA
<213> ORGANISM: Streptococcus pyogenes

<400> SEQUENCE: 9

```
gtgtcaaaat acctaaaata cttctctatt atcacgttat ttttgactgg gcttatttta      60
gttgcatgtc aacaacaaaa gcctcaaaca aaagaacgtc agcgcaaaca acgtccaaaa     120
gacgaacttg tcgtttctat gggggcaaag ctccctcatg aattcgatcc aaaggaccgt     180
tatggagtcc acaatgaagg gaatatcact catagcactc tattgaaacg ttctcctgaa     240
ctagatataa aaggagagct tgctaaaaca taccatctct ctgaagatgg gctgacttgg     300
tcgtttgact tgcatgatga ttttaaattc tcaaatggtg agcctgttac tgctgatgat     360
gttaagttta cttatgatat gttgaaagca gatggaaagg cttgggatct aaccttcatt     420
aagaacgttg aagtagttgg gaaaaatcag gtcaatatcc atttgactga ggcgcattcg     480
acatttacag cacagttgac tgaaatccca atcgtcccta aaaaacatta caatgataag     540
tataagagca atcctatcgg ttcaggacct tacatggtaa aagaatataa ggctggagaa     600
caagctattt ttgttcgtaa cccttattgg catgggaaaa aaccatactt taaaaaatgg     660
acttgggtct tacttgatga aaacacagca ctagcagctt tagaatctgg tgatgttgat     720
atgatctacg caacgccaga acttgctgat aaaaaagtca aaggcacccg cctccttgat     780
attccatcaa atgatgtgcg cggcttatca ttaccttatg tgaaaaaggg cgtcatcact     840
gattctcctg atggttatcc tgtaggaaat gatgtcacta gtgatccagc aatccgaaaa     900
gccttgacta ttggtttaaa taggcaaaaa gttctcgata cggttttaaa tggttatggt     960
aaaccagctt attcaattat tgataaaaca ccattttgga atccaaaaac agccattaaa    1020
gataataaag tagctaaagc taagcaatta ttgacaaaag cgggatggaa agaacaagca    1080
gacggtagcc gtaaaaaagg tgaccttgat gcagcgtttg atctgtacta ccctactaat    1140
gatcaattgc gagcgaactt agccgttgaa gtagcagagc aagccaaggc cctagggatt    1200
actattaaac tcaaagctag taactgggat gaaatggcaa cgaagtcaca tgactcagcc    1260
ttactttatg ccggaggacg tcatcacgcg cagcaatttt atgaatcgca tcatccaagc    1320
ctagcaggga aaggttggac caatattacg ttttataaca atcctaccgt gactaagtac    1380
cttgacaaag caatgacatc ttctgacctt gataaagcta acgaatattg gaagttagcg    1440
cagtgggatg gcaaaacagg tgcttctact cttggagatt tgccaaatgt atggttggtg    1500
agccttaacc atacttatat tggtgataaa cgtatcaatg taggtaaaca aggcgtccac    1560
agtcatggtc atgattggtc attattgact aacattgccg agtggacttg ggatgaatca    1620
actaagtaa                                                            1629
```

<210> SEQ ID NO 10
<211> LENGTH: 542
<212> TYPE: PRT
<213> ORGANISM: Streptococcus pyogenes

<400> SEQUENCE: 10

```
Val Ser Lys Tyr Leu Lys Tyr Phe Ser Ile Ile Thr Leu Phe Leu Thr
1               5                   10                  15

Gly Leu Ile Leu Val Ala Cys Gln Gln Gln Lys Pro Gln Thr Lys Glu
            20                  25                  30

Arg Gln Arg Lys Gln Arg Pro Lys Asp Glu Leu Val Val Ser Met Gly
        35                  40                  45

Ala Lys Leu Pro His Glu Phe Asp Pro Lys Asp Arg Tyr Gly Val His
    50                  55                  60

Asn Glu Gly Asn Ile Thr His Ser Thr Leu Leu Lys Arg Ser Pro Glu
```

-continued

```
65                  70                  75                  80

Leu Asp Ile Lys Gly Glu Leu Ala Lys Thr Tyr His Leu Ser Glu Asp
                85                  90                  95

Gly Leu Thr Trp Ser Phe Asp Leu His Asp Asp Phe Lys Phe Ser Asn
            100                 105                 110

Gly Glu Pro Val Thr Ala Asp Asp Val Lys Phe Thr Tyr Asp Met Leu
        115                 120                 125

Lys Ala Asp Gly Lys Ala Trp Asp Leu Thr Phe Ile Lys Asn Val Glu
    130                 135                 140

Val Val Gly Lys Asn Gln Val Asn Ile His Leu Thr Glu Ala His Ser
145                 150                 155                 160

Thr Phe Thr Ala Gln Leu Thr Glu Ile Pro Ile Val Pro Lys Lys His
                165                 170                 175

Tyr Asn Asp Lys Tyr Lys Ser Asn Pro Ile Gly Ser Gly Pro Tyr Met
            180                 185                 190

Val Lys Glu Tyr Lys Ala Gly Glu Gln Ala Ile Phe Val Arg Asn Pro
        195                 200                 205

Tyr Trp His Gly Lys Lys Pro Tyr Phe Lys Lys Trp Thr Trp Val Leu
    210                 215                 220

Leu Asp Glu Asn Thr Ala Leu Ala Ala Leu Glu Ser Gly Asp Val Asp
225                 230                 235                 240

Met Ile Tyr Ala Thr Pro Glu Leu Ala Asp Lys Lys Val Lys Gly Thr
                245                 250                 255

Arg Leu Leu Asp Ile Pro Ser Asn Asp Val Arg Gly Leu Ser Leu Pro
            260                 265                 270

Tyr Val Lys Lys Gly Val Ile Thr Asp Ser Pro Asp Gly Tyr Pro Val
        275                 280                 285

Gly Asn Asp Val Thr Ser Asp Pro Ala Ile Arg Lys Ala Leu Thr Ile
    290                 295                 300

Gly Leu Asn Arg Gln Lys Val Leu Asp Thr Val Leu Asn Gly Tyr Gly
305                 310                 315                 320

Lys Pro Ala Tyr Ser Ile Ile Asp Lys Thr Pro Phe Trp Asn Pro Lys
                325                 330                 335

Thr Ala Ile Lys Asp Asn Lys Val Ala Lys Ala Lys Gln Leu Leu Thr
            340                 345                 350

Lys Ala Gly Trp Lys Glu Gln Ala Asp Gly Ser Arg Lys Lys Gly Asp
        355                 360                 365

Leu Asp Ala Ala Phe Asp Leu Tyr Tyr Pro Thr Asn Asp Gln Leu Arg
    370                 375                 380

Ala Asn Leu Ala Val Glu Val Ala Glu Gln Ala Lys Ala Leu Gly Ile
385                 390                 395                 400

Thr Ile Lys Leu Lys Ala Ser Asn Trp Asp Glu Met Ala Thr Lys Ser
                405                 410                 415

His Asp Ser Ala Leu Leu Tyr Ala Gly Gly Arg His His Ala Gln Gln
            420                 425                 430

Phe Tyr Glu Ser His His Pro Ser Leu Ala Gly Lys Gly Trp Thr Asn
        435                 440                 445

Ile Thr Phe Tyr Asn Asn Pro Thr Val Thr Lys Tyr Leu Asp Lys Ala
    450                 455                 460

Met Thr Ser Ser Asp Leu Asp Lys Ala Asn Glu Tyr Trp Lys Leu Ala
465                 470                 475                 480

Gln Trp Asp Gly Lys Thr Gly Ala Ser Thr Leu Gly Asp Leu Pro Asn
                485                 490                 495
```

-continued

```
Val Trp Leu Val Ser Leu Asn His Thr Tyr Ile Gly Asp Lys Arg Ile
            500                 505                 510

Asn Val Gly Lys Gln Gly Val His Ser His Gly His Asp Trp Ser Leu
        515                 520                 525

Leu Thr Asn Ile Ala Glu Trp Thr Trp Asp Glu Ser Thr Lys
    530                 535                 540
```

MULTICOMPONENT IMMUNOGENIC COMPOSITION FOR THE PREVENTION OF BETA-HEMOLYTIC STREPTOCOCCAL (BHS) DISEASE

CROSS-REFERENCE TO RELATED APPLICATIONS

This application claims priority from U.S. Provisional Application No. 61/111,485, filed Nov. 5, 2008, which is incorporated herein by reference in its entirety.

FIELD OF THE INVENTION

This invention relates generally to β-hemolytic streptococcal (BHS) polypeptides and polynucleotides, particularly *Streptococcus pyogenes* polypeptides and polynucleotides, and their use in multicomponent immunogenic compositions to prevent BHS disease. More specifically, the invention relates to polypeptides of *Streptococcus pyogenes* which are surface localized. The invention further relates to immunogenic compositions, and methods for immunizing against and reducing β-hemolytic streptococcal infection comprising combinations of two or more of polypeptides.

BACKGROUND OF THE INVENTION

Traditional phenotypic criteria for classification of streptococci include both hemolytic reactions and Lancefield serological groupings. However, with taxonomic advances, it is now known that unrelated species of β-hemolytic (defined as the complete lysis of sheep erythrocytes in agar plates) streptococci (BHS) may produce identical Lancefield antigens and that strains genetically related at the species level may have heterogeneous Lancefield antigens. In spite of these exceptions to the traditional rules of streptococcal taxonomy, hemolytic reactions and Lancefield serological tests can still be used to divide streptococci into broad categories as a first step in identification of clinical isolates. Ruoff, K. L., R. A. Whiley, and D. Beighton. 1999. *Streptococcus*. In P. R. Murray, E. J. Baron, M. A. Pfaller, F. C. Tenover, and R. H. Yolken (eds.), Manual of Clinical Microbiology. American Society of Microbiology Press, Washington D.C.

β-hemolytic isolates with Lancefield group A, C, or G antigen can be subdivided into two groups: large-colony (>0.5 mm in diameter) and small-colony (<0.5 mm in diameter) formers. Large-colony-forming group A (*Streptococcus pyogenes*), C, and G strains are "pyogenic" streptococci replete with a variety of effective virulence mechanisms. *Streptococcus agalactiae* (group B) is still identified reliably by its production of Lancefield group B antigen or other phenotypic traits.

Similarities between BHS species include not only virulence factors, but also disease manifestations. Included in the latter are pneumonia, arthritis, abscesses, rhinopharyngitis, metritis, puerperal sepsis, neonatal septicemia, wound infections, meningitis, peritonitis, cellulitis, pyoderma, necrotizing fasciitis, toxic shock syndrome, septicemia, infective endocarditis, pericarditis, glomerulonephritis, and osteomyelitis.

*Streptococcus pyogenes* are Gram-positive diplococci that colonize the pharynx and skin of humans, sites that then serve as the primary reservoir for this organism. An obligate parasite, this bacterium is transmitted by either direct contact of respiratory secretions or by hand-to-mouth. The majority of *Streptococcus pyogenes* infections are relatively mild illnesses, such as pharyngitis or impetigo. Currently, there are anywhere from twenty million to thirty-five million cases of pharyngitis alone in the U.S., costing about $2 billion for physician visits and other related expenses. Additionally, nonsuppurative sequelae such as rheumatic fever, scarlet fever, and glomerulonephritis result from *Streptococcus pyogenes* infections. Globally, acute rheumatic fever (ARF) is the most common cause of pediatric heart disease (1997. Case definitions for Infectious Conditions Under Public Health Surveillance. CDC.).

From the initial portals of entry, pharynx, and skin, *Streptococcus pyogenes* can disseminate to other parts of the body where bacteria are not usually found, such as the blood, deep muscle and fat tissue, or the lungs, and can cause invasive infections. Two of the most severe but least common forms of invasive *Streptococcus pyogenes* disease are necrotizing fasciitis and streptococcal toxic shock syndrome (STSS). Necrotizing fasciitis (described in the media as "flesh-eating bacteria") is a destructive infection of muscle and fat tissue. STSS is a rapidly progressing infection causing shock and injury to internal organs such as the kidneys, liver, and lungs. Much of this damage is due to a toxemia rather than localized damage due to bacterial growth.

In 1995, invasive *Streptococcus pyogenes* infections and STSS became mandated reportable diseases. In contrast to the millions of individuals that acquire pharyngitis and impetigo, the U.S. Centers for Disease Control and Prevention (CDC) mandated case reporting indicates that in 1997 there were from 15,000 to 20,000 cases of invasive *Streptococcus pyogenes* disease in the United States, resulting in over 2,000 deaths (1997. Case definitions for Infectious Conditions Under Public Health Surveillance. CDC.). Other reports estimate invasive disease to be as high as 10-20 cases per 100,000 individuals per year (Stevens, D. L. 1995. Streptococcal toxic-shock syndrome: spectrum of disease, pathogenesis, and new concepts in treatment. Emerg Infect Dis. 1:69-78). More specifically, of the 15,000 to 20,000 cases of invasive disease, 1,100 to 1,500 are cases of necrotizing fasciitis and 1,000 to 1,400 are cases of STSS, with a 20% and 60% mortality rate, respectively. Also included in serious invasive disease are cases of myositis, which carries a fatality rate of 80% to 100%. An additional 10% to 15% of individuals die with other forms of invasive group A streptococcal disease. These numbers have increased since case reporting was initiated in 1995 and reflect a general trend that has occurred over the past decade or two. Additionally, it is commonly agreed that the stringency of the case definitions results in lower and, thus, misleading numbers, in that many cases are successfully resolved due to early diagnosis and treatment before the definition has been met.

While *Streptococcus pyogenes* remains sensitive to penicillin and its derivatives, treatment does not necessarily eradicate the organism. Approximately 5% to 20% of the human population are carriers depending on the season (Stevens, D. L. 1995. Streptococcal toxic-shock syndrome: spectrum of disease, pathogenesis, and new concepts in treatment. Emerg Infect Dis. 1:69-78), despite antibiotic therapy. The reasons for this are not totally clear and may involve a variety of mechanisms. In cases of serious invasive infections, treatment often requires aggressive surgical intervention. For those cases involving STSS or related disease, clindamycin (a protein synthesis inhibitor) is the preferred antibiotic as it penetrates tissues well and prevents exotoxin production. There are reports of some resistance to tetracycline, sulfa, and most recently, erythromycin. Clearly, there remains a need for compositions to prevent and treat β-hemolytic infection.

Numerous virulence factors have been identified for *Streptococcus pyogenes*, some secreted and some surface localized. Although it is encapsulated, the capsule is composed of hyaluronic acid and is not suitable as a candidate antigen for inclusion in immunogenic compositions, since it is commonly expressed by mammalian cells and is nonimmunogenic (Dale, J. B., R. G. Washburn, M. B. Marques, and M. R. Wessels. 1996. Hyaluronate capsule and surface M protein in resistance to opsonization of group A streptococci. Infect Immun. 64:1495-501). The T antigen and Group Carbohydrate are other candidates, but may also elicit cross-reactive antibodies to heart tissue. Lipoteichoic acid is present on the surface of *Streptococcus pyogenes*, but raises safety concerns similar to LPS.

The most abundant surface proteins fall into a family of proteins referred to as M or "M-like" proteins because of their structural similarity. While members of this class have similar biological roles in inhibiting phagocytosis, they each have unique substrate binding properties. The best characterized protein of this family is the helical M protein. Antibodies directed to homologous M strains have been shown to be opsonic and protective (Dale, J. B., R. W. Baird, H. S. Courtney, D. L. Hasty, and M. S. Bronze. 1994. Passive protection of mice against group A streptococcal pharyngeal infection by lipoteichoic acid. J Infect Dis. 169:319-23, Dale, J. B., M. Simmons, E. C. Chiang, and E. Y. Chiang. 1996. Recombinant, Ellen, R. P., and R. J. Gibbons. 1972. M protein-associated adherence of *Streptococcus pyogenes* to epithelial surfaces: prerequisite for virulence. Infect Immun. 5:826-830.). Complicating the use of M protein as a candidate antigen is the fact that there have been approximately 100 different serotypes of M protein identified with several more untyped. Typically, the Class I M serotypes, exemplified by serotypes M1, M3, M6, M12, and M18, are associated with pharyngitis, scarlet fever, and rheumatic fever and do not express immunoglobulin binding proteins. Class II M serotypes, such as M2 and M49, are associated with the more common localized skin infections and the sequelae glomerulonephritis, and do express immunoglobulin binding proteins (Podbielski, A., A. Flosdorff, and J. Weber-Heynemann. 1995. The group A streptococcal virR49 gene controls expression of four structural vir regulon genes. Infect Immun. 63:9-20). It is important to note that there is little, if any, heterologous cross-reactivity of antibodies to M serotypes. Equally important is the role these antibodies play in rheumatic fever. Specific regions of M protein elicit antibodies that cross react with host heart tissue, causing or at least correlating with cellular damage (Cunningham, M. W., and A. Quinn. 1997. Immunological crossreactivity between the class I epitope of streptococcal M protein and myosin. Adv Exp Med Biol. 418:887-921, Quinn, A., K. Ward, V. A. Fischetti, M. Hemric, and M. W. Cunningham. 1998. Immunological relationship between the class I epitope of streptococcal M protein and myosin. Infect Immun. 66:4418-24.).

M and M-like proteins belong to a large family of surface localized proteins that are defined by the sortase-targeted LPXTG motif (Mazmanian, S. K., G. Liu, H. Ton-That, and O. Schneewind. 1999. *Staphylococcus aureus* sortase, an enzyme that anchors surface proteins to the cell wall. Science. 285:760-3, Ton-That, H., G. Liu, S. K. Mazmanian, K. F. Faull, and O. Schneewind. 1999. Purification and characterization of sortase, the transpeptidase that cleaves surface proteins of *Staphylococcus aureus* at the LPXTG motif. Proc Natl Acad Sci USA. 96:12424-12429). This motif, located near the carboxy-terminus of the protein, is first cleaved by sortase between the threonine and glycine residues of the LPXTG motif. Once cleaved, the protein is covalently attached via the carboxyl of threonine to a free amide group of the amino acid cross-bridge in the peptidoglycan, thus permanently attaching the protein to the surface of the bacterial cell. Included in this family of sortase-targeted proteins are the C5a peptidase (Chen, C. C., and P. P. Cleary. 1989. Cloning and expression of the streptococcal C5a peptidase gene in *Escherichia coli*: linkage to the type 12 M protein gene. Infect. Immun. 57:1740-1745, Chmouryguina, I., A. Suvorov, P. Ferrieri, and P. P. Cleary. 1996. Conservation of the C5a peptidase genes in group A and B streptococci. Infect. Immun. 64:2387-2390), adhesins for fibronectin (Courtney, H. S., Y. Li, J. B. Dale, and D. L. Hasty. 1994. Cloning, sequencing, and expression of a fibronectin/fibrinogen-binding protein from group A streptococci. Infect Immun. 62:3937-46, Fogg, G. C., and M. G. Caparon. 1997. Constitutive expression of fibronectin binding in *Streptococcus pyogenes* as a result of anaerobic activation of rofA. J Bacteriol. 179:6172-80, Hanski, E., and M. Caparon. 1992. Protein F, a fibronectin-binding protein, is an adhesion of the group A streptococcus *Streptococcus pyogenes*. Proc Natl Acad Sci., USA. 89:6172-76, Hanski, E., P. A. Horwitz, and M. G. Caparon. 1992. Expression of protein F, the fibronectin-binding protein of *Streptococcus pyogenes* JRS4, in heterologous streptococcal and enterococcal strains promotes their adherence to respiratory epithelial cells. Infect Immun. 60:5119-5125), vitronectin, and type IV collagen, and other M-like proteins that bind plasminogen, IgA, IgG, and albumin (Kihlberg, B. M., M. Collin, A. Olsen, and L. Bjorck. 1999. Protein H, an antiphagocytic surface protein in *Streptococcus pyogenes*. Infect Immun. 67:1708-14).

Numerous secreted proteins have been described, several of which are considered to be toxins. Most *Streptococcus pyogenes* isolates from cases of serious invasive disease and streptococcal toxic shock syndrome (STSS) produce streptococcal pyogenic exotoxins (SPE) A and C (Cockerill, F. R., 3rd, R. L. Thompson, J. M. Musser, P. M. Schlievert, J. Talbot, K. E. Holley, W. S. Harmsen, D. M. Ilstrup, P. C. Kohner, M. H. Kim, B. Frankfort, J. M. Manahan, J. M. Steckelberg, F. Roberson, and W. R. Wilson. 1998. Molecular, serological, and clinical features of 16 consecutive cases of invasive streptococcal disease. Southeastern Minnesota Streptococcal Working Group. Clin Infect Dis. 26:1448-58). Other pyogenic exotoxins have also been identified in the genomic *Streptococcus pyogenes* sequence completed at the University of Oklahoma, submitted to GenBank and assigned accession number AE004092, and have been characterized (Proft, T., S. Louise Moffatt, C. J. Berkahn, and J. D. Fraser. 1999. Identification and Characterization of Novel Superantigens from *Streptococcus pyogenes*. J Exp Med. 189:89-102). Other toxins such as Toxic Shock Like Syndrome toxin, Streptococcal Superantigen (Reda, K. B., V. Kapur, D. Goela, J. G. Lamphear, J. M. Musser, and R. R. Rich. 1996. Phylogenetic distribution of streptococcal superantigen SSA allelic variants provides evidence for horizontal transfer of ssa within *Streptococcus pyogenes*. Infect Immun. 64:1161-5), and Mitogenic Factor (Yutsudo, T., K. Okumura, M. Iwasaki, A. Hara, S. Kamitani, W. Minamide, H. Igarashi, and Y. Hinuma. 1994. The gene encoding a new mitogenic factor in a *Streptococcus pyogenes* strain is distributed only in group A streptococci. Infection and Immunity. 62:4000-4004) play lesser-defined roles in disease. Streptolysin O could also be considered a possible candidate antigen, because it causes the release of IL-β release. In addition, a variety of secreted enzymes have also been identified that include the Cysteine protease (Lukomski, S., C. A. Montgomery, J. Rurangirwa, R. S. Geske, J. P. Banish, G. J. Adams, and J. M. Musser. 1999. Extracellular cysteine protease produced by *Streptococcus pyogenes* participates in the pathogenesis of invasive skin infection and dissemination in mice. Infect Immun. 67:1779-

88, Matsuka, Y. V., S. Pillai, S. Gubba, J. M. Musser, and S. B. Olmsted. 1999. Fibrinogen cleavage by the *Streptococcus pyogenes* extracellular cysteine protease and generation of antibodies that inhibit enzyme proteolytic activity. Infect Immun. 67:4326-33), Streptokinase (Huang, T. T., H. Malke, and J. J. Ferretti. 1989. The streptokinase gene of group A streptococci: cloning, expression in *Escherichia coli*, and sequence analysis. Mol Microbiol. 3:197-205, Nordstrand, A., W. M. McShan, J. J. Ferretti, S. E. Holm, and M. Norgren. 2000. Allele substitution of the streptokinase gene reduces the nephritogenic capacity of group A streptococcal strain NZ131. Infect Immun. 68:1019-25), and Hyaluronidase (Hynes, W. L., A. R. Dixon, S. L. Walton, and L. J. Aridgides. 2000. The extracellular hyaluronidase gene (hylA) of *Streptococcus pyogenes*. FEMS Microbiol Lett. 184:109-12, Hynes, W. L., L. Hancock, and J. J. Ferretti. 1995. Analysis of a second bacteriophage hyaluronidase gene from *Streptococcus pyogenes*: evidence for a third hyaluronidase involved in extracellular enzymatic activity. Infect Immun. 63:3015-20).

Given the number of known virulence factors produced by *Streptococcus pyogenes*, it is clear that an important characteristic for a successful β-hemolytic streptococcal immunogenic composition would be its ability to stimulate a response that would prevent or limit colonization early in the infection process. This protective response would either block adherence and/or enhance the clearance of cells through opsonophagocytosis. Antibodies to M protein have been shown to be opsonic and provide a mechanism to overcome the anti-phagocytic properties of the protein (Jones, K. F., and V. A. Fischetti. 1988. The importance of the location of antibody binding on the M6 protein for opsonization and phagocytosis of group A M6 streptococci. J Exp Med. 167:1114-23) in much the same way that anti-serotype B capsular antibodies have demonstrated protection from disease caused by *Haemophilus influenzae* B (Madore, D. V. 1998. Characterization of immune response as an indicator of *Haemophilus influenzae* type b vaccine efficacy. Pediatr Infect Dis J. 17:S207-10). In addition, antibodies specific to Protein F have been shown to block adherence and internalization by tissue culture cells (Molinari, G., S. R. Talay, P. Valentin-Weigand, M. Rohde, and G. S. Chhatwal. 1997. The fibronectin-binding protein of *Streptococcus pyogenes*, SfbI, is involved in the internalization of group A streptococci by epithelial cells. Infect Immun. 65:1357-63).

There remains a need to develop immunogenic compositions and methods to prevent or ameliorate infections caused by β-hemolytic streptococci, including groups A, B, C and G. There also remains a need to provide immunogenic compositions which provide immunity to a broad range of BHS bacteria.

SUMMARY OF THE INVENTION

To meet these and other needs, and in view of its purposes, the present invention provides immunogenic compositions for the protecting of susceptible mammals against colonization or infection by β-hemolytic streptococci including Group A, B, C, and/or D streptocci, including those from *Streptococcus pyogenes*. These immunogenic compositions conrprise a mixture of two or more polypeptides as described more fully below. The invention also provides methods of preventing or ameliorating such coloziation, in a susceptible mammal by administering an effective amount of the immunogenic composition to generate antibodes to the specific polyeptides contained within the immunogenic compositon. The invention further provides *Streptococcus pyogenes* polypeptides and polynucleotides, recombinant materials, and methods for their production. Another aspect of the invention relates to methods for using such *Streptococcus pyogenes* polypeptides and polynucleotides. The polypeptides and polynucleotides can also be used in the manufacture of a medicament for preventing or ameliorating an infection caused by β-hemolytic streptococci.

The polypeptides utilized in the immunogenic compositions of the invention include isolated polypeptides comprising at least one of an amino acid sequence of any of FIG. 2, 4, 6, 8, or 10. The invention also includes amino acid sequences that have at least 90% identity to any of the foregoing amino acid sequences, and mature polypeptides of these. The invention further includes immunogenic fragments and biological equivalents of these polypeptides. Also provided are antibodies that immunospecifically bind to the polypeptides of the invention.

The polynucleotides of the invention include isolated polynucleotides that comprise nucleotide sequences that encode a polypeptide of the invention. These polynucleotides include isolated polynucleotides comprising at least one of a nucleotide sequence of any of FIG. 1, 3, 5, 7, or 9, and also include other nucleotide sequences that, as a result of the degeneracy of the genetic code, also encode a polypeptide of the invention. The invention also includes isolated polynucleotides comprising a nucleotide sequence that has at least 90% identity to a nucleotide sequence that encodes a polypeptide of the invention, and isolated polynucleotides comprising a nucleotide sequences that has at least 90% identity to any of the foregoing nucleotide sequences. In addition, the isolated polynucleotides of the invention include nucleotide sequences that hybridize under stringent hybridization conditions to a nucleotide sequence that encodes a polypeptide of the invention, nucleotide sequences that hybridize under stringent hybridization conditions to a nucleotide sequence of any of the foregoing sequences, and nucleotide sequences that are fully complementary to these polynucleotides. Furthermore, the invention includes expression vectors and host cells comprising these polynucleotides.

The invention also provides immunogenic compositions which comprise an immunogenic amount of at least two or more components (selected from SCP (FIG. 2 (SEQ ID NO:2) and the peptides coded for by ORF 554 (peptidylpropyl isomerase (FIG. 4 (SEQ ID NO:4)), ORF 1218 (hypothetical protein (FIG. 6 (SEQ ID NO:6)), ORF 1358 (putative adhesion protein (FIG. 8 (SEQ ID NO:8)), and ORF 2459 (surface lipoprotein (FIG. 10 (SEQ ID NO:10)) each of which comprises a polypeptide of the invention in an amount effective to prevent or ameliorate a β-hemolytic streptococcal colonization or infection in a susceptible mammal. Each component may comprise the polypeptide itself, or may comprise the polypeptide and any other substance (e.g., one or more chemical agents, proteins, etc.) that can aid in the prevention and/or amelioration of β-hemolytic streptococcal colonization or infection. These immunogenic compositions can further comprise at least a portion of the polypeptide, optionally conjugated or linked to a peptide, polypeptide, or protein, or to a polysaccharide.

The invention also includes methods of protecting a susceptible mammal against β-hemolytic streptococcal colonization or infection. In one embodiment, the method comprises administering to a mammal an effective amount of a two or more immunogenic composition comprising an immunogenic amount of a polypeptide of the invention, which amount is effective to prevent or ameliorate β-hemolytic streptococcal colonization or infection in the susceptible mammal. Such combinations of components, it has been found, are effective to provide such protection to a broad range of groups, and generally provide a greater immune response than the individual components administered separately. The immunogenic compositions of the invention can be administered by any conventional route, for example, by subcutaneous or intramuscular injection, oral ingestion, or intranasally.

The invention further provides immunogenic compositions. In one embodiment, the immunogenic composition comprises at least one polypeptide of the invention. In another embodiment, the immunogenic composition comprises at least one polynucleotide of the invention.

It is to be understood that the foregoing general description and the following detailed description are exemplary, but are not restrictive, of the invention.

BRIEF DESCRIPTION OF THE DRAWINGS

FIG. 1 presents the nucleic acid sequence encoding for C5a peptidase ("SCP"; SEQ ID NO:1).

FIG. 2 presents the amino acid sequence of SCP (SEQ ID NO:2).

FIG. 3 presents the nucleic acid sequence of ORF 554 encoding for peptidylpropyl isomerase (SEQ ID NO:3).

FIG. 4 presents the amino acid sequence of peptidylpropyl isomerase (SEQ ID NO:4).

FIG. 5 presents the nucleic acid sequence of ORF 1218 encoding for a hypothetical protein (SEQ ID NO:5).

FIG. 6 presents the amino acid sequence of a hypothetical protein (SEQ ID NO:6).

FIG. 7 presents the nucleic acid sequence of ORF 1358 encoding for a putative adhesion protein (SEQ ID NO:7).

FIG. 8 presents the amino acid sequence of a putative adhesion protein (SEQ ID NO:8).

FIG. 9 presents the nucleic acid sequence of ORF 2459 encoding for a surface lipoprotein (SEQ ID NO:9).

FIG. 10 presents the amino acid sequence of a surface lipoprotein (SEQ ID NO:10).

FIG. 11 graphically presents percentage killing compared to media of the three component ("Trivax"=SCP, peptidylpropyl isomerase (ORF 554), and putative adhesion protein (ORF 1358)) and one component ("554"=peptidylpropyl isomerase (ORF 554)) immunogenic compositions examined in Example 2.

DETAILED DESCRIPTION OF THE INVENTION

Figure 12:
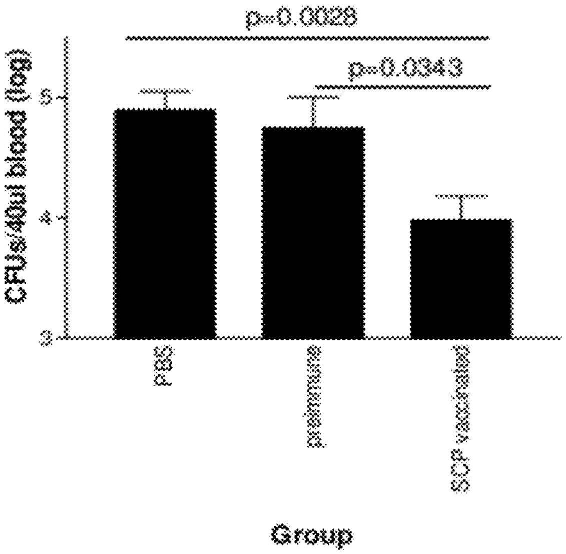
FIGS. 12-16 graphically demonstrate the passive immunity transfer results of Example 3. CFUs=colony forming units.

The present invention provides immunogenic compositions to prevent or ameliorate infections caused by β-hemolytic streptococci, including groups A, B, C and G. Two or more of the polypeptides enumerated herein are combined together to make an immunogenic composition.

Specifically, in one embodiment, an immunogenic composition of this invention comprises a mixture of two or more polypeptides, each polypeptide encoded by a nucleic acid sequence having at least 90% identity to a nucleic acid sequence selected from the group consisting of:

(a) C5a peptidase ("SCP") (FIG. 1 (SEQ ID NO:1));
(b) open reading frame ("ORF") 554 (FIG. 3 (SEQ ID NO:3));
(c) ORF 1218 (FIG. 5 (SEQ ID NO:5));
(d) ORF 1358 (FIG. 7 (SEQ ID NO:7)); and
(e) ORF 2459 (FIG. 9 (SEQ ID NO:9)).

In another embodiment, an immunogenic composition of this invention comprises a mixture of two or more polypeptides, each polypeptide having at least 90% identity to an amino acid sequence selected from the group consisting of:

(a) SCP (FIG. 2 (SEQ ID NO:2));
(b) peptidylpropyl isomerase (FIG. 4 (SEQ ID NO:4));
(c) hypothetical protein (FIG. 6 (SEQ ID NO:6));
(d) putative adhesion protein (FIG. 8 (SEQ ID NO:8)); and
(e) surface lipoprotein (FIG. 10 (SEQ ID NO:10)).

In yet another embodiment, an immunogenic composition of this invention comprises a mixture of:

(a) an SCP polypeptide encoded by a nucleic acid sequence having at least 90% identity to the nucleic acid sequence of FIG. 1 (SEQ ID NO:1);
(b) a peptidylpropyl isomerase polypeptide encoded by a nucleic acid sequence having at least 90% identity to the nucleic acid sequence of FIG. 3 (SEQ ID NO:3); and
(c) at least one other polypeptide encoded by a nucleic acid sequence having at least 90% identity to an nucleic acid sequence selected from the group consisting of (i) FIG. 5 (SEQ ID NO:5); (ii) FIG. 7 (SEQ ID NO:7); and (iii) FIG. 9 (SEQ ID NO:9).

In still another embodiment, an immunogenic composition of this invention comprises a mixture of:

(a) an SCP polypeptide having at least 90% identity to the amino acid sequence of FIG. 2 (SEQ ID NO:2);
(b) a peptidylpropyl isomerase polypeptide having at least 90% identity to the amino acid sequence of FIG. 4 (SEQ ID NO:4); and
(c) at least one other polypeptide having at least 90% identity to an amino acid sequence of the group consisting of (i) FIG. 6 (SEQ ID NO:6); (ii) FIG. 8 (SEQ ID NO:8); and (iii) FIG. 10 (SEQ ID NO:10).

The terms "polynucleotide", "nucleic acid" and "nucleic acid fragment" are used interchangeably herein. These terms encompass nucleotides connected by phosphodiester linkages. A "polynucleotide" may be a ribonucleic acid (RNA) or deoxyribonucleic acid (DNA) polymer that is single- or double-stranded, that optionally contains synthetic, non-natural or altered nucleotide bases. A polynucleotide in the form of a polymer of DNA may comprise one or more segments of cDNA, genomic DNA, synthetic DNA, or mixtures thereof. Nucleotide bases are indicated herein by a single letter code: adenine (A), guanine (G), thymine (T), cytosine (C), inosine (I) and uracil (U).

The streptococcal polynucleotides described herein may be obtained using standard cloning and screening techniques. These polynucleotides may be obtained, for example, from genomic DNA, from a cDNA library derived from mRNA, from a genomic DNA library, or can be synthesized using well known and commercially available techniques, such as e.g. by PCR from a cDNA library or via RT-PCR (reverse transcription-polymerase chain reaction).

There are several methods available and well known to those skilled in the art to obtain full-length cDNAs or to extend short cDNAs, such as e.g. those based on the method of rapid amplification of cDNA ends (RACE). See Frohman et al., Proc. Natl. Acad. Sci. USA 85, 8998-9002, 1988. Recent modifications of the technique, exemplified by the MARATHON™ technology (Clontech Laboratories Inc.) for example, have significantly simplified the search for longer cDNAs. In the MARATHON™ technology, cDNAs have been prepared from mRNA extracted from a chosen tissue and an "adaptor" sequence ligated onto each end. Nucleic acid amplification (PCR) is then carried out to amplify the "missing" 5' end of the cDNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or by carrying out a separate full-length PCR using the new sequence information for the design of the 5' primer.

The term "recombinant" means, for example, that a polynucleotide is made by an artificial combination of two or more otherwise separated polynucleotide segments, e.g., by chemical synthesis or by the manipulation of isolated polynucleotides using genetic engineering techniques. A "recombinant DNA construct" comprises any of the isolated polynucleotides of the present invention operably linked to at least one regulatory element.

Orthologues and allelic variants of the streptococcal polynucleotides can readily be identified using methods well known in the art. Allelic variants and orthologs of the polynucleotides can comprise a nucleotide sequence that is typically at least about 90-95% or more identical to any one or more of the nucleotide sequences shown in odd numbered FIGS. 1-9 (odd numbered SEQ ID NO:'S 1-9), or fragments thereof. The allelic variants and orthologs of these polynucleotides can encode a polypeptide that comprises an amino acid sequence that is at least 90% identical to the amino acid sequence set forth in any one or more of even numbered FIGS. 2-10 (even numbered SEQ ID NO:'S 2-10). Such polynucleotides can readily be identified as being able to hybridize under stringent conditions, to any one or more of the polynucleotides having a nucleotide sequence set forth in FIGS. 1-9 (odd numbered SEQ ID NO:'S 1-9), or fragments thereof.

It is well understood by one skilled in the art that many levels of sequence identity are useful in identifying related polynucleotide and polypeptide sequences. Sequence alignments and percent identity calculations can be performed using the MEGALIGN™ program of the LASERGENE™ bioinformatics computing suite (DNASTAR Inc., Madison, Wis.). Multiple alignment of the sequences can be performed using the Clustal method of alignment (Higgins and Sharp, Gene, 73(1):237-44, 1988) with the default parameters of e.g. GAP PENALTY=10 and GAP LENGTH PENALTY=10. Default parameters for pairwise alignments using the Clustal method can be e.g. KTUPLE 1, GAP PENALTY=3, WINDOW=5 and DIAGONALS SAVED=5.

A polypeptide sequence of the invention may be identical to the recited sequence, that is, 100% identical, or it may include up to a certain integer number of amino acid alterations as compared to the reference sequence such that the % identity is less than 100%. Such alterations include at least one amino acid deletion, substitution, including conservative and non-conservative substitution, or insertion. The alterations may occur at the amino- or carboxy-terminal positions of the reference polypeptide sequence or anywhere between those terminal positions, interspersed either individually among the amino acids in the reference amino acid sequence or in one or more contiguous groups within the reference amino acid sequence.

Thus, the invention also provides isolated polypeptides having sequence identity to the amino acid sequences contained in therecited sequences. Depending on the particular sequence, the degree of sequence identity is preferably greater than 90% (e.g., 90%, 95%, 97%, 99% or more). These homologous proteins include mutants and allelic variants.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al. 1984), BLASTP, BLASTN, and FASTA (Altschul, S. F., et al., 1990. The BLASTX program is publicly available from NCBI and other sources (BLAST Manual, Altschul, S., et al., NCBI NLM NIH Bethesda, Md. 20894; Altschul, S., et al., 1990). The well known Smith Waterman algorithm may also be used to determine identity.

For example, the number of amino acid alterations for a given % identity can be determined by multiplying the total number of amino acids in one of even numbered FIGS. 2-10 (SEQ ID NO:'S 2, 4, 6, 8 and 10) by the numerical percent of the respective percent identity (divided by 100) and then subtracting that product from said total number of amino acids in the one of even numbered FIGS. 2-10 (SEQ ID NO:'S 2, 4, 6, 8 and 10), or:

$$n_a \leq x_a - (x_a \cdot y),$$

wherein $n_a$ is the number of amino acid alterations, $x_a$ is the total number of amino acids in the one of even numbered FIGS. 2-10 (SEQ ID NO:'S 2, 4, 6, 8 and 10), and y is, for instance, 0.90 for 90%, 0.95 for 95%, 0.97 for 97% etc., and wherein any non-integer product of $x_a$ and y is rounded down to the nearest integer prior to subtracting it from $x_a$.

The present invention also contemplates isolated polypeptides that are substantially conserved across strains of β-hemolytic streptococci. Further, isolated polypeptides that are substantially conserved across strains of β-hemolytic streptococci and that are effective in preventing or ameliorating a β-hemolytic streptococcal colonization or infection in a susceptible subject are also contemplated by the present invention. As used herein, the term "conserved" refers to, for example, the number of amino acids that do not undergo insertions, substitution and/or deletions as a percentage of the total number of amino acids in a protein. For example, if a protein is 90% conserved and has, for example, 263 amino acids, then there are 237 amino acid positions in the protein at which amino acids do not undergo substitution. Likewise, if a protein is 95% conserved and has, for example, about 280 amino acids, then there are 14 amino acid positions at which amino acids may undergo substitution and 266 (i.e., 280 minus 14) amino acid positions at which the amino acids do not undergo substitution. According to an embodiment of the present invention, the isolated polypeptide is preferably at least about 90% conserved across the strains of β-hemolytic streptococci, more preferably at least about 95% conserved across the strains, even more preferably at least about 97% conserved across the strains, and most preferably at least about 99% conserved across the strains, without limitation.

Modifications and changes can be made in the structure of the polypeptides and still obtain polypeptides having β-hemolytic streptococci and/or *Streptococcus pyogenes* activity and/or antigenicity. For example, certain amino acids can be substituted for other amino acids in a sequence without appreciable loss of activity and/or antigenicity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

The invention includes any isolated polypeptide which is a biological equivalent that provides the desired reactivity as described herein. The term "desired reactivity" refers to reactivity that would be recognized by a person skilled in the art as being a useful result for the purposes of the invention. Examples of desired reactivity are described herein, including without limitation, desired levels of protection, desired antibody titers, desired opsonophagocytic activity and/or desired cross-reactivity, such as would be recognized by a person skilled in the art as being useful for the purposes of the present invention. The desired opsonophagocytic activity is indicated by a percent killing of bacteria as measured by decrease in colony forming units (CFU) in OPA versus a negative control. Without being limited thereto, the desired opsonophagocytic activity is preferably at least about 15%, more preferably at least about 20%, even more preferably at least about 40%, even more preferably at least about 50% and most preferably at least about 60%.

The invention includes polypeptides that are variants of the polypeptides comprising an amino acid sequence of even numbered FIGS. 2-10 (SEQ ID NO:'S 2, 4, 6, 8 and 10). "Variant" as the term is used herein, includes a polypeptide that differs from a reference polypeptide, but retains essential properties. Generally, differences are limited so that the sequences of the reference polypeptide and the variant are closely similar overall and, in many regions, identical (i.e., biologically equivalent). A variant and reference polypeptide may differ in amino acid sequence by one or more substitutions, additions, or deletions in any combination. A substituted or inserted amino acid residue may or may not be one encoded by the genetic code. A variant of a polypeptide may be a naturally occurring such as an allelic variant, or it may be a variant that is not known to occur naturally. Non-naturally occurring variants of polypeptides may be made by direct synthesis or by mutagenesis techniques.

In making such changes, the hydropathic index of amino acids can be considered. The importance of the hydropathic amino acid index in conferring interactive biologic function on a polypeptide is generally understood in the art (Kyte & Doolittle, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are listed in parentheses after each amino acid as follows: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within +/−2 is preferred, those which are within +/−1 are particularly preferred, and those within +/−0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e., with a biological property of the polypeptide.

As detailed in U.S. Pat. No. 4,554,101, incorporated herein by reference, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted for another having a similar hydrophilicity value and still obtain a biologically equivalent and in particular, an immunologically equivalent, polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally, therefore, based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. As shown in Table I below, suitable amino acid substitutions include the following:

TABLE 1

| Original Residue | Exemplary Residue Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |

TABLE 1-continued

| Original Residue | Exemplary Residue Substitution |
|---|---|
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Thus, the invention includes functional or biological equivalents of the polypeptides of the sequences in even numbered FIGS. 2-10 (SEQ ID NO:'S 2, 4, 6, 8 and 10) that contain one or more amino acid substitutions.

Biological or functional equivalents of a polypeptide can also be prepared using site-specific mutagenesis. Site-specific mutagenesis is a technique useful in the preparation of second generation polypeptides, or biologically, functionally equivalent polypeptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a phage vector which can exist in both a single-stranded and double-stranded form. Typically, site-directed mutagenesis in accordance herewith is performed by first obtaining a single-stranded vector which includes within its sequence a DNA sequence which encodes all or a portion of the *Streptococcus pyogenes* polypeptide sequence selected. An oligonucleotide primer bearing the desired mutated sequence is prepared, for example, by well known techniques (e.g., synthetically). This primer is then annealed to the single-stranded vector, and extended by the use of enzymes, such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutation. Commercially available kits provide the necessary reagents.

The polypeptides and polypeptide antigens of the invention are understood to include any polypeptide comprising substantial sequence similarity, structural similarity, and/or functional similarity to a polypeptide comprising an amino acid sequence of any of even numbered FIGS. 2-10 (SEQ ID NO:'S 2, 4, 6, 8 and 10). In addition, a polypeptide or polypeptide antigen of the invention is not limited to a particular source. Thus, the invention provides for the general detection and isolation of the polypeptides from a variety of sources.

The polypeptides of the invention may be in the form of the "mature" protein or may be a part of a larger protein such as a fusion protein. It is often advantageous to include an additional amino acid sequence which contains, for example, secretory or leader sequences, pro-sequences, sequences which aid in purification such as multiple histidine residues, or an additional sequence for stability during recombinant production.

The term "immunogenic composition" as used herein refers to any type of biological agent in an administratable form capable of stimulating an immune response in a subject inoculated with the immunogenic composition. An immune response may include induction of antibodies and/or induction of a T-cell response. The term "protection," when used in reference to an immunogenic composition, refers herein to the amelioration (either partial or complete) of any of the symptoms associated with the disease or condition in question. Thus, protection of subjects from infection by a *Streptococcus* species such as *S. dysgalactiae* (including the subspecies *Dysgalactiae* and *Equisimilis*) by the present immunogenic compositions generally results in a diminishing of bacterial growth and/or one or more of the clinical symptoms associated with streptococcal infection, including arthritis, endocarditis, meningitis, polyserositis, bronchopneumonia, meningitis, permanent hearing loss and septic shock.

The methods disclosed herein may include inducing an immune response against one or more pathogens that include a species of *Streptococcus* (e.g., *Streptococcus dysgalactiae, S. dysgalactiae* sub. *Equisimilis, S. dysgalactiae* sub. *Dysgalactiae, S. pyogenes, S. agalactiae, S. anginosus, S. constellatus, S. equisimilis* and *S. intermedius*.) For example, the methods may include inducing polyclonal antibody production against one or more streptococcal pathogens such as e.g. *S. dysgalactiae* sub. *Equisimilis.*

As discussed above, immunogenic compositions comprise two or more polypeptides of the invention. To do so, one or more polypeptides are adjusted to an appropriate concentration and can be formulated with any suitable adjuvant, diluent, pharmaceutically acceptable carrier, or any combination thereof. As used herein the phrase "pharmaceutically acceptable carrier" is intended to include any and all solvents, dispersion media, coatings, antibacterial and antifungal agents, isotonic and absorption delaying agents, excipients and the like, compatible with pharmaceutical administration. The use of such media and agents for pharmaceutically active substances is well known in the art. Physiologically acceptable vehicles may be used as carriers and/or diluents. A pharmaceutically acceptable vehicle is understood to designate a compound or a combination of compounds entering into a pharmaceutical or immunogenic composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen. These include, but are not limited to, water, Ringer's solution, an appropriate isotonic medium, glycerol, ethanol and other conventional solvents, phosphate buffered saline, and the like.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, CREMOPHOR EL™ (Polyethoxylated castor oil) (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyetheylene glycol and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and the like. In many cases, isotonic agents are included in the composition, for example, sugars, polyalcohols such as manitol, sorbitol and/or sodium chloride. Prolonged absorption of the injectable compositions can be brought about by including in the composition an agent which delays absorption, for example, aluminum monostearate and gelatin.

Sterile injectable solutions can be prepared by incorporating the polypeptides in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-α, 1-β, 2, 4, 5, 6, 7, 8 and 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as CD40 and CD40L; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Suitable adjuvants used to enhance an immune response further include, without limitation, MPL™ (3-O-deacylated monophosphoryl lipid A, Corixa, Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918. One such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Still other adjuvants include muramyl peptides, such as N-acetyl-muramyl-L-threonyl-D-isoglutamine (thr-MDP), N-acetyl-normuramyl-L-alanine-2-(1'-2'dipalmitoyl-sn-glycero-3-hydroxyphosphoryloxy)-ethylamine (MTP-PE); oil-in-water emulsions, such as MF59 (U.S. Pat. No. 6,299,884) (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, Mass.)), and SAF (containing 10% Squalene, 0.4% Tween 80, 5% pluronic-blocked polymer L121, and thr-MDP, either microfluidized into a submicron emulsion or vortexed to generate a larger particle size emulsion); aluminum salts (alum), such as aluminum hydroxide, aluminum phosphate, aluminum sulfate; Amphigen; Avridine; L121/squalene; D-lactide-polylactide/glycoside; pluronic polyols; killed Bordetella; saponins, such as Stimulon™ QS-21 (Antigenics, Framingham, Mass.), described in U.S. Pat. No. 5,057,540, ISCOMATRIX (CSL Limited, Parkville, Australia), described in U.S. Pat. No. 5,254,339, and immunostimulating complexes (ISCOMS); Mycobacterium tuberculosis; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

The polypeptide can also include at least a portion of the polypeptide, optionally conjugated or linked to a peptide, polypeptide, or protein, or to a polysaccharide. It is also anticipated that the immunogenic compositions can contain other components, such as polysaccharides, alone or conjugated to proteins which can elicit an immune response.

Various tests are used to assess the in vitro immunogenicity of the polypeptides comprising the immunogenic compositions of the invention. For example, an in vitro opsonic assay is conducted by incubating together a mixture of *Streptococcus* sp. cells, heat inactivated serum containing specific antibodies to the polypeptide in question, and an exogenous complement source. Opsonophagocytosis proceeds during incubation of freshly isolated polymorphonuclear cells (PMN's) and the antibody/complement/*Streptococcus* sp. cell mixture. Bacterial cells that are coated with antibody and complement are killed upon opsonophagocytosis. Colony forming units (cfu) of surviving bacteria that escape from opsonophagocytosis are determined by plating the assay mixture. Titers are reported as the reciprocal of the highest dilution that gives ≥50% bacterial killing, as determined by comparison to assay controls. Specimens that demonstrate less than 50% killing at the lowest serum dilution tested (1:8), are reported as having an opsonophagocytosis antibody (OPA) titer of 4. The method described above is a modification of Gray's method (Gray, Conjugate Vaccines Supplement, p. 694-697,1990).

A test serum control, which contains test serum plus bacterial cells and heat inactivated complement, is included for each individual serum. This control is used to assess whether the presence of antibiotics or other serum components are capable of killing the bacterial strain directly (i.e. in the absence of complement or PMN's). A human serum with known opsonic titer is used as a positive human serum control. The opsonic antibody titer for each unknown serum is calculated as the reciprocal of the initial dilution of serum giving 50% cfu reduction compared to the control without serum.

A whole cell ELISA assay can also be used to assess in vitro immunogenicity and surface exposure of the polypeptide antigen, wherein the bacterial strain of interest is coated onto a plate, such as a 96 well plate, and test sera from an immunized animal is reacted with the bacterial cells. If any antibody specific for the test polypeptide antigen is reactive with a surface exposed epitope of the polypeptide antigen, it can be detected by standard methods known to one skilled in the art. A similar approach is to monitor the antigen on the cell surface using Flow Cytometry and antigen specific antibodies.

Any polypeptide demonstrating the desired in vitro activity may then be tested in an in vivo animal challenge model. In some embodiments, immunogenic compositions are used in the immunization of an animal (e.g., a mouse) by methods and routes of immunization known to those of skill in the art (e.g., intranasal, parenteral, intramuscular, oral, rectal, vaginal, transdermal, intraperitoneal, intravenous, subcutaneous, etc.). Following immunization of the animal with a Streptococcal immunogenic composition, the animal is challenged with one or more Streptococcal species and assayed for resistance to *Streptococcus* spp. infection.

Combination immunogenic compositions are provided by including two or more of the polypeptides of the invention, as well as by combining one or more of the polypeptides of the invention with one or more known *Streptococcus pyogenes* polypeptides, including, but not limited to, the M proteins, adhesins, and the like.

Once formulated, the immunogenic compositions of the invention can be administered directly to the subject, delivered ex vivo to cells derived from the subject, or in vitro for expression of recombinant proteins. For delivery directly to the subject, administration may be by any conventional form, such as intranasally, parenterally, orally, intraperitoneally, intravenously, subcutaneously, or topically applied to any mucosal surface such as intranasal, oral, eye, lung, vaginal, or rectal surface, such as by an aerosol spray.

It is advantageous to formulate oral or parenteral compositions in unit dosage form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

For parenteral administration, immunogenic compositions of the invention can be administered as injectable dosages in a physiologically acceptable diluent with a pharmaceutically acceptable carrier that can be a sterile liquid such as water oils, saline, glycerol, or ethanol. Additionally, auxiliary substances, such as wetting or emulsifying agents, surfactants, pH buffering substances and the like can be present in compositions. Other components can include those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)). The immunogenic compositions of this invention can be administered in the form of a depot injection or implant preparation, which can be formulated in such a manner as to permit a sustained or pulsatile release of the active ingredient.

The subjects are generally human. An immunologically effective amount of the immunogenic composition in an appropriate number of doses is administered to the subject to elicit an immune response. Immunologically effective amount, as used herein, means the administration of that amount to a mammalian host (preferably human), either in a single dose or as part of a series of doses, sufficient to at least cause the immune system of the individual treated to generate an immune response that reduces the clinical impact of the bacterial infection. The term "immune response" or "immunological response" includes the development of a humoral (antibody-mediated) and/or a cellular (mediated by antigen-specific T cells or their secretion products) response. Protection may be conferred by a single dose of the immunogenic composition, or may require the administration of several doses, in addition to booster doses at later times to maintain protection. This may range from a minimal decrease in bacterial burden to prevention of the infection. Ideally, the treated individual will not exhibit the more serious clinical manifestations of the β-hemolytic streptococcal infection. The dosage amount can vary depending upon specific conditions of the individual, such as age and weight. This amount can be determined in routine trials by means known to those skilled in the art.

In prophylactic applications, immunogenic compositions are administered to a subject susceptible to, or otherwise at risk of, beta hemolytic streptococcal infection in an amount sufficient to eliminate or reduce the risk, lessen the severity, or delay the outset of the disease, including biochemical, histologic and/or behavioral symptoms of disease associated with the infection, its complications and intermediate pathological phenotypes presenting during development of the disease. In therapeutic applications, compositions are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

It has been observed that there is no single peptide sequence that provides protection for all strains of BHS, including groups A, B, C, and G. As shown in Table II (presented in Example 1 below), below, each antigen provides an immune response against a subset of these groups.

Generally, any combination of two or more surface-expressed antigens from BHS will be expected to provide the enhanced immune response described above. Such could include the antigens discussed above BHS capsular antigens, M protein, ABC transporter, or any other surface exposed antigen. However, it has been found that the following antigens exhibit particularly beneficial properties for the production of immunogenic compositions:

SCP (C5a Peptidase)
peptidylpropyl isomerase (encoded by ORF 554)
putative adhesion protein (encoded by ORF 1358)
surface lipoprotein (encoded by ORF 2459)
hypothetical protein (encoded by ORF 1218)

Combinations of two or more of these antigens into a single multicompnent immunogenic composition provide enhanced protection against one or more groups of BHS and produce an enhanced immune response to them.

EXAMPLES

The following examples are illustrative and the present invention is not intended to be limited thereto.

Example 1

Antibody Binding

The binding of antibodies to bacteria, a process known as opsonization, can lead to uptake and killing of the bacteria by phagocytic cells. Screening of such antibodies is used in to determine the effectiveness of antibodies raised against particular serotypes in killing bacteria expressing or not expressing that serotype on the surface.

For each serotype screened, antibodies were raised in mice against the antibodies encoded for by the recited ORF. The antibodies were then screened against various BHS strains. Screening of the antibodies was performed by fluorescence activated cell sorting (FACS). Briefly, heat killed streptococci were incubated with a recited antibody on ice for 45 minutes, followed by two washes. The streptococci were then incubated with a goat anti-mouse-Alexa-488 antibody (Molecular Probes, Eugene, Oreg.) for 30 minutes on ice, followed by two washes. Cells thus treated were run on a FACS machine (e.g. see DeMaster et al., Infect. Immun., 70(1): 350-359, 2002.) The results are summarized in Table 2.

In the course of screening those anti-beta hemolytic-streptococcal antisera and monoclonal antibodies against various beta hemolytic streptococcal (BHS) strains, it was noted that some antisera and antibodies are cross-reactive against many BHS strains, including members of *Streptococcus pyogenes* (Group A streptococci), *Streptococcus agalactiae* (Group B streptococci) and Group C and Group G streptococci (which include the streptococcal species *Streptococcus anginosus, Streptococcus constellatus, Streptococcus intermedius, Streptococcus dysgalactiae* sub. *Equisimilis* and *Streptococcus dysgalactiae* sub. Dysgalactiae). This cross-reactivity also means that the polypeptides recited or encoded by the relevant ORF may be used in an immunogenic composition to induce an immune response effective to protect against infection by Group A or Group B *Streptococcus*, as well as by Group C or Group G *Streptococcus*.

In Table 2, the symbol "+" means that the antibodies react to the antigen at least three-fold over background; the symbol "±" means that the antibodies react to the antigen between two-fold and three-fold over background; and the sysmbol "−" means that the detection of antibody signal is at or below background.

| strain # | Genus/Species | pre | 554 | 1224 | 1358 | 1818 | 2459 | SCP | 1218 | mIgG1 | C5a-1484-16 | C5a-1522-13 |
|---|---|---|---|---|---|---|---|---|---|---|---|---|
| GAR 1165 | *Streptococcus pyogenes* | − | + | + | + | + | + | + | + | − | + | + |
| GAR 1199 | *Streptococcus pyogenes* | − | + | + | + | + | + | + | + | − | + | + |
| GAR 1251 | *Streptococcus pyogenes* | − | + | + | + | + | + | + | + | − | +/− | − |
| GAR 1278 | *Streptococcus pyogenes* | − | + | + | + | + | + | + | +/− | − | +/− | +/− |
| GAR 1362 | *Streptococcus pyogenes* | − | + | + | + | + | + | + | + | − | + | + |
| GAR 1439 | *Streptococcus pyogenes* | − | + | + | + | + | + | + | + | − | + | + |
| GAR 1530 | *Streptococcus pyogenes* | − | + | + | + | + | + | + | + | − | − | +/− |
| GAR 1566 | *Streptococcus pyogenes* | − | + | +/− | + | + | + | + | +/− | − | +/− | +/− |
| GAR 1672 | *Streptococcus pyogenes* | − | + | +/− | + | + | + | + | + | − | + | + |
| GAR 1839 | *Streptococcus pyogenes* | − | + | + | + | + | + | + | +/− | − | + | + |
| GAR 1923 | *Streptococcus pyogenes* | − | + | + | + | + | + | + | +/− | − | +/− | +/− |
| GAR 2107 | *Streptococcus pyogenes* | − | + | +/− | + | + | + | + | + | − | + | + |
| GAR 2330 | *Streptococcus pyogenes* | − | + | + | + | + | + | + | + | − | +/− | +/− |
| GAR 2646 | *Streptococcus pyogenes* | − | + | +/− | + | + | + | + | + | − | + | + |
| GAR 2650 | *Streptococcus pyogenes* | − | + | + | + | + | + | + | + | − | − | +/− |
| GAR 2869 | *Streptococcus pyogenes* | − | + | + | + | + | + | + | + | − | + | + |
| GAR 3104 | *Streptococcus pyogenes* | − | + | + | + | + | + | + | + | − | + | + |
| GAR 3549 | *Streptococcus pyogenes* | − | + | + | + | + | + | + | + | − | + | − |
| GAR 3784 | *Streptococcus pyogenes* | − | + | + | + | + | + | + | + | − | + | + |
| GAR 4029 | *Streptococcus pyogenes* | − | + | + | + | + | +/− | + | + | − | + | − |
| GAR 4030 | *Streptococcus pyogenes* | − | + | + | + | + | + | + | + | − | + | +/− |
| GAR 4230 | *Streptococcus pyogenes* | − | + | + | + | + | + | + | + | − | + | + |
| GAR 4773 | *Streptococcus pyogenes* | − | + | + | + | + | + | + | + | − | + | + |
| GAR 4983 | *Streptococcus pyogenes* | − | + | +/− | + | + | + | + | +/− | − | + | + |
| GAR 4987 | *Streptococcus pyogenes* | − | + | +/− | + | + | + | + | + | − | + | + |
| GAR 5861 | *Streptococcus pyogenes* | − | + | +/− | + | + | +/− | + | +/− | − | + | + |
| GAR 5991 | *Streptococcus pyogenes* | − | + | + | + | + | + | + | + | − | + | + |
| GAR 6084 | *Streptococcus pyogenes* | − | + | +/− | + | + | + | + | + | − | + | + |
| GAR 7055 | *Streptococcus pyogenes* | − | + | + | + | + | + | + | + | − | + | + |
| GS20 | *Streptococcus pyogenes* | − | + | +/− | + | + | + | + | +/− | NT | NT | NT |

-continued

| strain # | Genus/Species | pre | 554 | 1224 | 1358 | 1818 | 2459 | SCP | 1218 | mIgG1 | C5a-1484-16 | C5a-1522-13 |
|---|---|---|---|---|---|---|---|---|---|---|---|---|
| GS21 | *Streptococcus pyogenes* | − | + | +/− | + | + | + | + | + | NT | NT | NT |
| GS22 | *Streptococcus pyogenes* | − | + | +/− | + | + | + | + | + | NT | NT | NT |
| GS23 | *Streptococcus pyogenes* | − | + | +/− | + | + | + | + | + | NT | NT | NT |
| GS24 | *Streptococcus pyogenes* | − | + | +/− | + | + | + | + | + | NT | NT | NT |
| GS25 | *Streptococcus pyogenes* | − | + | +/− | + | + | + | + | + | NT | NT | NT |
| GS26 | *Streptococcus pyogenes* | − | + | + | + | + | + | + | + | NT | NT | NT |
| GS29 | *Streptococcus pyogenes* | − | + | + | + | + | + | + | + | NT | NT | NT |
| GS30 | *Streptococcus pyogenes* | − | + | +/− | + | + | + | + | + | NT | NT | NT |
| GS31 | *Streptococcus pyogenes* | − | +/− | − | +/− | +/− | +/− | + | − | NT | NT | NT |
| GS32 | *Streptococcus pyogenes* | − | + | +/− | + | + | + | + | + | NT | NT | NT |
| GS33 | *Streptococcus pyogenes* | − | + | + | + | + | + | + | + | NT | NT | NT |
| GS34 | *Streptococcus pyogenes* | − | + | +/− | + | + | + | + | + | NT | NT | NT |
| GS35 | *Streptococcus pyogenes* | − | + | + | + | + | + | + | + | NT | NT | NT |
| GS36 | *Streptococcus pyogenes* | − | +/− | − | +/− | +/− | +/− | + | − | NT | NT | NT |
| GS37 | *Streptococcus pyogenes* | − | + | +/− | + | + | + | + | + | NT | NT | NT |
| GS38 | *Streptococcus pyogenes* | − | + | + | + | + | + | + | + | NT | NT | NT |
| GS39 | *Streptococcus pyogenes* | − | + | +/− | + | + | + | + | +/− | NT | NT | NT |
| GS40 | *Streptococcus pyogenes* | − | + | + | + | + | + | + | + | NT | NT | NT |
| GS41 | *Streptococcus pyogenes* | − | + | − | + | + | + | + | +/− | NT | NT | NT |
| GS42 | *Streptococcus pyogenes* | − | + | +/− | +/− | + | +/− | + | + | NT | NT | NT |
| GS43 | *Streptococcus pyogenes* | − | + | + | + | + | + | + | + | NT | NT | NT |
| GS44 | *Streptococcus pyogenes* | − | + | + | + | + | + | + | + | NT | NT | NT |
| GS45 | *Streptococcus pyogenes* | − | + | + | + | + | + | + | + | NT | NT | NT |
| GS46 | *Streptococcus pyogenes* | − | + | +/− | + | + | + | + | + | NT | NT | NT |
| GS47 | *Streptococcus pyogenes* | − | + | +/− | +/− | + | + | + | + | NT | NT | NT |
| GS48 | *Streptococcus pyogenes* | − | + | − | +/− | +/− | +/− | + | +/− | NT | NT | NT |
| GS49 | *Streptococcus pyogenes* | − | + | + | + | + | + | + | + | NT | NT | NT |
| GS50 | *Streptococcus pyogenes* | − | + | + | + | + | + | + | + | NT | NT | NT |
| GS51 | *Streptococcus pyogenes* | − | + | + | + | + | + | + | + | NT | NT | NT |
| GS52 | *Streptococcus pyogenes* | − | + | +/− | + | + | + | + | + | NT | NT | NT |
| GS53 | *Streptococcus pyogenes* | − | + | + | + | + | + | + | + | NT | NT | NT |
| GS54 | *Streptococcus pyogenes* | − | +/− | +/− | +/− | + | +/− | + | + | NT | NT | NT |
| GS55 | *Streptococcus pyogenes* | − | + | +/− | + | + | + | + | +/− | NT | NT | NT |
| GS56 | *Streptococcus pyogenes* | − | + | +/− | + | + | + | + | + | NT | NT | NT |
| GS57 | *Streptococcus pyogenes* | − | + | +/− | + | + | + | + | + | NT | NT | NT |
| GS58 | *Streptococcus pyogenes* | − | + | + | + | + | + | + | + | NT | NT | NT |
| GS59 | *Streptococcus pyogenes* | − | + | + | + | + | + | + | + | NT | NT | NT |
| GS60 | *Streptococcus pyogenes* | − | + | +/− | + | + | + | + | + | NT | NT | NT |
| GS61 | *Streptococcus pyogenes* | − | + | +/− | + | + | +/− | + | + | NT | NT | NT |
| GS62 | *Streptococcus pyogenes* | − | + | + | + | + | + | + | + | NT | NT | NT |
| GS63 | *Streptococcus pyogenes* | − | + | +/− | + | + | + | + | + | NT | NT | NT |
| GS64 | *Streptococcus pyogenes* | − | + | +/− | + | + | + | + | + | NT | NT | NT |
| GS65 | *Streptococcus pyogenes* | − | + | + | + | + | + | + | + | NT | NT | NT |
| GS66 | *Streptococcus pyogenes* | − | + | +/− | + | + | +/− | + | + | NT | NT | NT |
| GAR 1 | *Streptococcus agalactiae* | − | + | + | + | + | + | + | +/− | − | − | − |
| GAR 1012 | *Streptococcus agalactiae* | − | +/− | − | − | − | − | + | − | − | − | − |
| GAR 1023 | *Streptococcus agalactiae* | − | − | − | − | − | − | − | − | − | − | − |
| GAR 1049 | *Streptococcus agalactiae* | − | − | − | − | − | − | − | − | − | − | − |
| GAR 10895 | *Streptococcus agalactiae* | − | − | − | − | +/− | − | + | − | − | − | − |
| GAR 1192 | *Streptococcus agalactiae* | − | +/− | +/− | +/− | + | +/− | + | − | − | − | − |
| GAR 127 | *Streptococcus agalactiae* | − | − | − | − | +/− | − | + | − | − | − | − |
| GAR 12790 | *Streptococcus agalactiae* | − | − | − | − | − | − | +/− | − | − | − | − |
| GAR 1305 | *Streptococcus agalactiae* | − | − | − | − | − | − | +/− | − | − | − | − |
| GAR 131 | *Streptococcus agalactiae* | − | − | − | − | − | − | +/− | − | − | − | − |
| GAR 1355 | *Streptococcus agalactiae* | − | − | − | − | − | − | +/− | − | − | − | − |
| GAR 1446 | *Streptococcus agalactiae* | − | − | − | − | − | − | + | +/− | − | − | − |
| GAR 1494 | *Streptococcus agalactiae* | − | − | − | − | +/− | − | + | +/− | − | − | − |
| GAR 154 | *Streptococcus agalactiae* | − | + | + | + | + | + | +/− | +/− | − | − | − |
| GAR 176 | *Streptococcus agalactiae* | − | − | − | − | − | − | + | − | − | − | − |
| GAR 18 | *Streptococcus agalactiae* | − | + | + | + | + | + | +/− | − | − | − | − |
| GAR 1844 | *Streptococcus agalactiae* | − | − | − | − | − | − | + | +/− | − | − | − |
| GAR 1931 | *Streptococcus agalactiae* | − | − | − | − | + | − | + | + | − | − | − |
| GAR 2369 | *Streptococcus agalactiae* | − | − | − | +/− | +/− | +/− | + | − | − | − | − |
| GAR 252 | *Streptococcus agalactiae* | − | − | − | − | − | − | +/− | − | − | − | − |
| GAR 2533 | *Streptococcus agalactiae* | − | − | − | − | − | − | − | − | − | − | − |
| GAR 2682 | *Streptococcus agalactiae* | − | + | − | − | − | − | + | − | − | − | − |
| GAR 2717 | *Streptococcus agalactiae* | − | − | − | − | − | − | +/− | − | − | − | − |
| GAR 2723 | *Streptococcus agalactiae* | − | − | − | − | − | − | − | +/− | − | − | − |
| GAR 2724 | *Streptococcus agalactiae* | − | − | − | − | − | − | +/− | +/− | − | − | − |
| GAR 2842 | *Streptococcus agalactiae* | − | +/− | − | − | − | − | +/− | − | − | − | − |
| GAR 287 | *Streptococcus agalactiae* | − | − | − | − | +/− | − | + | − | − | − | − |
| GAR 3003 | *Streptococcus agalactiae* | − | − | − | − | − | − | − | − | − | − | − |
| GAR 3751 | *Streptococcus agalactiae* | − | − | − | − | − | − | + | +/− | − | +/− | − |
| GAR 381 | *Streptococcus agalactiae* | − | − | − | − | +/− | − | +/− | − | − | − | − |
| GAR 3830 | *Streptococcus agalactiae* | − | − | − | − | − | − | + | + | − | − | − |
| GAR 4131 | *Streptococcus agalactiae* | − | +/− | − | − | − | − | + | + | − | − | − |
| GAR 4293 | *Streptococcus agalactiae* | − | − | − | +/− | + | +/− | + | +/− | − | − | − |
| GAR 4398 | *Streptococcus agalactiae* | − | − | − | − | − | − | − | + | − | − | − |

-continued

| strain # | Genus/Species | pre | 554 | 1224 | 1358 | 1818 | 2459 | SCP | 1218 | mIgG1 | C5a-1484-16 | C5a-1522-13 |
|---|---|---|---|---|---|---|---|---|---|---|---|---|
| GAR 462 | *Streptococcus agalactiae* | − | − | − | − | − | − | − | − | − | − | − |
| GAR 4837 | *Streptococcus agalactiae* | − | +/− | − | − | − | − | + | +/− | − | − | − |
| GAR 54 | *Streptococcus agalactiae* | − | − | − | − | − | − | + | − | − | +/− | − |
| GAR 562 | *Streptococcus agalactiae* | − | + | +/− | + | + | +/− | + | +/− | − | − | − |
| GAR 6016 | *Streptococcus agalactiae* | − | + | +/− | + | + | + | + | − | − | − | − |
| GAR 614 | *Streptococcus agalactiae* | − | + | + | +/− | + | + | + | +/− | − | − | − |
| GAR 63 | *Streptococcus agalactiae* | − | + | +/− | + | + | + | + | +/− | − | − | − |
| GAR 6332 | *Streptococcus agalactiae* | − | +/− | +/− | + | + | + | + | +/− | − | + | +/− |
| GAR 6387 | *Streptococcus agalactiae* | − | + | +/− | +/− | +/− | +/− | + | + | − | +/− | − |
| GAR 6505 | *Streptococcus agalactiae* | − | +/− | +/− | +/− | +/− | + | + | +/− | − | + | + |
| GAR 67 | *Streptococcus agalactiae* | − | − | − | − | + | − | + | − | − | − | − |
| GAR 864 | *Streptococcus agalactiae* | − | +/− | − | +/− | +/− | +/− | + | − | − | − | − |
| GAR 967 | *Streptococcus agalactiae* | − | − | − | − | − | − | +/− | − | − | − | − |
| GS19 | GGS | − | +/− | +/− | +/− | + | +/− | + | + | NT | NT | NT |
| GS27 | GGS | − | +/− | + | +/− | + | +/− | + | +/− | NT | NT | NT |
| ATCC 33397 | *Streptococcus anginosus* | − | +/− | +/− | +/− | +/− | +/− | +/− | − | − | − | − |
| ATCC 33397 | *Streptococcus anginosus* | − | − | − | − | − | − | − | − | − | − | − |
| GAR 10823 | *Streptococcus anginosus* | − | +/− | + | +/− | +/− | +/− | + | − | − | − | − |
| GAR 1272 | *Streptococcus anginosus* | − | − | − | − | − | − | +/− | − | − | − | − |
| GAR 1370 | *Streptococcus anginosus* | − | − | − | − | − | − | − | − | − | − | − |
| GAR 1425 | *Streptococcus anginosus* | − | +/− | +/− | +/− | +/− | − | +/− | − | − | − | − |
| GAR 1592 | *Streptococcus anginosus* | − | − | − | − | − | − | − | − | − | − | − |
| GAR 1595 | *Streptococcus anginosus* | − | − | +/− | − | − | − | +/− | − | − | − | − |
| GAR 2044 | *Streptococcus anginosus* | − | − | +/− | − | − | − | − | − | − | − | − |
| GAR 2523 | *Streptococcus anginosus* | − | − | +/− | − | +/− | − | +/− | − | − | − | − |
| GAR 2565 | *Streptococcus anginosus* | − | − | +/− | − | +/− | +/− | +/− | +/− | − | − | − |
| GAR 2697 | *Streptococcus anginosus* | − | +/− | + | +/− | +/− | +/− | +/− | − | − | − | − |
| GAR 2822 | *Streptococcus anginosus* | − | +/− | − | − | − | +/− | − | +/− | − | − | − |
| GAR 3091 | *Streptococcus anginosus* | − | − | +/− | − | +/− | − | +/− | − | − | − | − |
| GAR 3560 | *Streptococcus anginosus* | − | + | + | + | +/− | + | +/− | − | − | − | − |
| GAR 3576 | *Streptococcus anginosus* | − | − | − | +/− | − | − | − | − | − | − | − |
| GAR 3858 | *Streptococcus anginosus* | − | +/− | +/− | +/− | +/− | +/− | +/− | − | − | − | − |
| GAR 3938 | *Streptococcus anginosus* | − | − | − | − | − | − | − | +/− | − | − | − |
| GAR 4133 | *Streptococcus anginosus* | − | − | − | +/− | +/− | − | + | +/− | − | − | − |
| GAR 4158 | *Streptococcus anginosus* | − | + | − | + | +/− | + | +/− | − | − | − | − |
| GAR 4234 | *Streptococcus anginosus* | − | − | − | + | +/− | +/− | +/− | − | − | − | − |
| GAR 4426 | *Streptococcus anginosus* | − | +/− | − | + | +/− | + | + | + | − | − | − |
| GAR 4680 | *Streptococcus anginosus* | − | +/− | − | + | +/− | +/− | +/− | +/− | − | − | − |
| GAR 4834 | *Streptococcus anginosus* | − | − | +/− | +/− | − | − | − | − | − | − | − |
| GAR 4896 | *Streptococcus anginosus* | − | + | +/− | + | +/− | + | + | − | − | − | − |
| GAR 5093 | *Streptococcus anginosus* | − | − | − | + | − | + | +/− | +/− | − | − | − |
| GAR 5094 | *Streptococcus anginosus* | − | +/− | +/− | + | +/− | +/− | +/− | +/− | − | − | − |
| GAR 5675 | *Streptococcus anginosus* | − | − | +/− | − | +/− | − | +/− | − | − | − | − |
| GAR 5776 | *Streptococcus anginosus* | − | + | + | + | + | + | + | +/− | − | − | − |
| GAR 5831 | *Streptococcus anginosus* | − | − | + | +/− | + | +/− | + | +/− | − | − | − |
| GAR 6187 | *Streptococcus anginosus* | − | +/− | +/− | +/− | +/− | − | − | +/− | − | − | − |
| GAR 6590 | *Streptococcus anginosus* | − | +/− | +/− | +/− | +/− | +/− | +/− | − | − | − | − |
| GAR 7000 | *Streptococcus anginosus* | − | +/− | + | +/− | + | +/− | + | − | − | − | − |
| GAR 7023 | *Streptococcus anginosus* | − | +/− | +/− | − | +/− | − | +/− | +/− | − | − | − |
| GAR 7190 | *Streptococcus anginosus* | − | − | − | − | − | − | +/− | − | − | − | − |
| GAR 7214 | *Streptococcus anginosus* | − | + | + | +/− | +/− | +/− | + | +/− | − | − | − |
| GAR 7468 | *Streptococcus anginosus* | − | − | − | − | + | − | +/− | − | − | − | − |
| GAR 7818 | *Streptococcus anginosus* | − | + | + | + | + | + | + | +/− | − | NT | − |
| GAR 8620 | *Streptococcus anginosus* | − | + | + | + | + | +/− | + | − | − | NT | − |
| GAR 8693 | *Streptococcus anginosus* | − | +/− | − | − | − | − | − | +/− | − | − | − |
| GAR 8722 | *Streptococcus anginosus* | − | − | − | +/− | − | − | − | − | − | − | − |
| GAR 8736 | *Streptococcus anginosus* | − | − | +/− | − | +/− | − | − | − | − | − | − |
| GAR 8954 | *Streptococcus anginosus* | − | +/− | +/− | +/− | +/− | − | +/− | − | − | − | − |
| ATCC 27823 | *Streptococcus constellatus* | − | +/− | − | − | − | − | +/− | − | − | − | − |
| GAR 1235 | *Streptococcus constellatus* | − | − | − | − | − | − | − | − | − | − | − |
| GAR 1384 | *Streptococcus constellatus* | − | + | − | +/− | +/− | +/− | +/− | + | − | − | − |
| GAR 1811 | *Streptococcus constellatus* | − | + | + | + | + | + | + | − | − | − | − |
| GAR 2421 | *Streptococcus constellatus* | − | +/− | +/− | +/− | +/− | +/− | +/− | − | − | − | − |
| GAR 3145 | *Streptococcus constellatus* | − | − | +/− | − | − | − | − | +/− | − | − | − |
| GAR 3355 | *Streptococcus constellatus* | − | − | − | − | − | − | − | − | − | − | − |
| GAR 4048 | *Streptococcus constellatus* | − | +/− | − | +/− | − | − | − | − | − | − | − |
| GAR 4083 | *Streptococcus constellatus* | − | +/− | − | + | +/− | + | +/− | − | − | − | − |
| GAR 4861 | *Streptococcus constellatus* | − | + | +/− | + | + | + | +/− | − | − | − | − |
| GAR 4870 | *Streptococcus constellatus* | − | +/− | − | + | + | +/− | + | +/− | − | − | − |
| GAR 5757 | *Streptococcus constellatus* | − | − | − | +/− | − | − | − | − | − | − | +/− |
| GAR 6129 | *Streptococcus constellatus* | − | + | +/− | +/− | +/− | +/− | +/− | − | − | − | − |
| GAR 6147 | *Streptococcus constellatus* | − | − | − | − | − | − | +/− | − | − | − | − |
| GAR 6258 | *Streptococcus constellatus* | − | +/− | +/− | + | + | + | + | − | − | − | − |
| GAR 7224 | *Streptococcus constellatus* | − | + | +/− | + | + | +/− | + | +/− | − | − | − |
| GAR 7369 | *Streptococcus constellatus* | − | + | + | + | + | +/− | + | − | − | − | − |
| ATCC 12394 | *Streptococcus dysgalactiae* | − | + | + | +/− | + | +/− | + | − | − | + | + |
| ATCC 12394 | *Streptococcus dysgalactiae* | − | + | + | + | + | +/− | + | − | − | +/− | +/− |
| ATCC 43078 | *Streptococcus dysgalactiae* | − | − | − | − | − | − | − | − | − | − | − |

-continued

| strain # | Genus/Species | pre | 554 | 1224 | 1358 | 1818 | 2459 | SCP | 1218 | mIgG1 | C5a-1484-16 | C5a-1522-13 |
|---|---|---|---|---|---|---|---|---|---|---|---|---|
| ATCC 43078 | *Streptococcus dysgalactiae* | – | – | – | – | – | – | – | – | – | – | – |
| GAR 3868 | *Streptococcus dysgalactiae* | – | +/– | +/– | +/– | +/– | + | + | +/– | – | – | – |
| GAR 4272 | *Streptococcus dysgalactiae* | – | + | + | + | +/– | + | + | – | – | – | – |
| ATCC 35666 | *Streptococcus dysgalactiae* sub. *equisimilis* | – | + | + | + | + | + | + | +/– | – | – | – |
| BAA-338 | *Streptococcus dysgalactiae* sub. *equisimilis* | – | – | +/– | +/– | +/– | + | + | +/– | – | – | – |
| GAR 3015 | *Streptococcus equisimilis* | – | + | +/– | + | +/– | +/– | + | + | – | + | + |
| ATCC 27335 | *Streptococcus intermedius* | – | + | +/– | + | +/– | +/– | – | +/– | – | – | – |
| ATCC 27335 | *Streptococcus intermedius* | – | + | +/– | + | +/– | – | +/– | +/– | – | – | – |
| GAR 2407 | *Streptococcus intermedius* | – | +/– | +/– | – | +/– | – | – | – | – | – | – |
| GS28 | unk | – | + | + | + | + | + | + | + | NT | NT | NT |
| GS67 | GGS/GCS | – | + | + | + | + | +/– | + | + | NT | NT | NT |
| GS68 | GGS/GCS | – | +/– | – | +/– | – | +/– | + | +/– | NT | NT | NT |
| GS69 | GGS/GCS | – | +/– | +/– | – | – | – | + | + | NT | NT | NT |
| GS70 | GGS/GCS | – | +/– | +/– | +/– | – | +/– | + | +/– | NT | NT | NT |
| GS71 | GGS/GCS | – | + | +/– | + | + | + | + | + | NT | NT | NT |
| GS72 | GGS/GCS | – | + | + | + | + | + | + | + | NT | NT | NT |
| GS73 | GGS/GCS | – | +/– | – | – | – | – | +/– | +/– | NT | NT | NT |
| GS74 | GGS/GCS | – | – | – | – | – | – | – | – | NT | NT | NT |
| GS75 | GGS/GCS | – | +/– | +/– | +/– | +/– | + | + | + | NT | NT | NT |
| GS77 | GGS/GCS | – | + | ND | + | +/– | +/– | + | + | NT | NT | NT |
| GS78 | GGS/GCS | – | +/– | +/– | + | +/– | +/– | + | +/– | NT | NT | NT |
| GS79 | GGS/GCS | – | +/– | – | +/– | +/– | – | + | – | NT | NT | NT |
| GS80 | GGS/GCS | – | – | – | – | – | +/– | + | + | NT | NT | NT |
| GS81 | GGS/GCS | – | + | + | +/– | + | + | + | +/– | NT | NT | NT |
| GS82 | GGS/GCS | – | +/– | +/– | +/– | + | +/– | + | +/– | NT | NT | NT |
| GS83 | GGS/GCS | – | + | + | + | + | + | + | + | NT | NT | NT |
| GS84 | GGS/GCS | – | – | – | – | – | – | – | – | NT | NT | NT |
| GS85 | GGS/GCS | – | +/– | +/– | – | +/– | +/– | – | +/– | NT | NT | NT |
| GS86 | GGS/GCS | – | +/– | – | +/– | +/– | +/– | + | +/– | NT | NT | NT |
| GS88 | GGS/GCS | – | + | +/– | + | + | + | +/– | + | NT | NT | NT |
| GS89 | GGS/GCS | – | +/– | +/– | – | – | – | + | + | NT | NT | NT |
| GS90 | GGS/GCS | – | – | +/– | +/– | + | + | + | + | NT | NT | NT |
| GS91 | GGS/GCS | – | +/– | +/– | +/– | + | +/– | + | + | NT | NT | NT |
| GS92 | GGS/GCS | – | + | +/– | +/– | +/– | +/– | +/– | +/– | NT | NT | NT |
| GS93 | GGS/GCS | – | + | + | + | + | + | + | + | NT | NT | NT |
| GS94 | GGS/GCS | – | + | + | + | +/– | + | + | + | NT | NT | NT |

Example 2

Use of a Three Component Immunogenic Composition to Produce Immune Sera

A trivalent immunogenic composition consisting of SCP, the polypeptide encoded by ORF 554, and the polypeptide encoded by ORF 1358 adjuvanted with aluminum phosphate was prepared, and the immunogenic composition was used to produce hyperimmune rabbit serum by three subcutaneous inoculations separated by 2-4 weeks, followed by exsanguination; a monovalent immunogenic composition consisting of similarly adjuvanted polypeptide encoded by ORF 554 was used as a control. The sera were screened for opsonophagocytic activity (OPA) against *S. pyogenes* SF370 at various dilutions. Briefly, the bacteria were incubated with 10 ul of sera for one hour in the presence of complement (baby rabbit complement), and then diluted 1:10 and plated on blood agar plates. The results are presented in FIG. 11.

As shown, it can be seen that the Trivax elicits increased opsonophagocytic activity than the 554 immunogenic composition, which is indicative of a much better killing of the bacteria.

Example 3

Passive Immunity Transfer

Antibodies were raised against each of the following antigens as described above: SCP and polypeptides encoded by ORFs 554, 1358, 2459, and 1218. These antibodies were then injected into infant rats without fully functional immune systems. The treated rats are then subsequently challenged with *S. pyogenes*, and recovered bacteria were counted four hours post-challenege. The negative control was PBS, and the positive human control was 385 sera.

Figure 13:
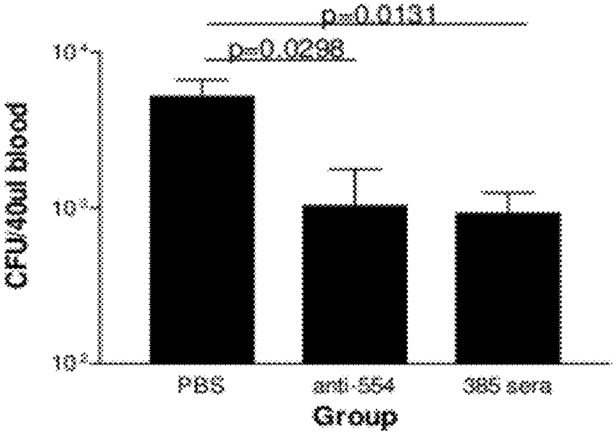
Figure 14:
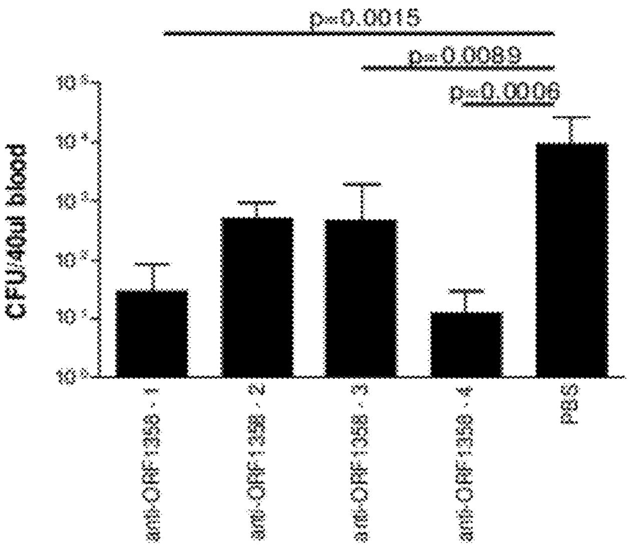
Figure 15:
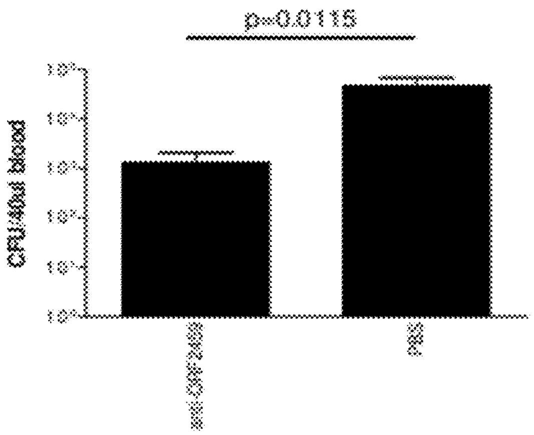
Figure 16:
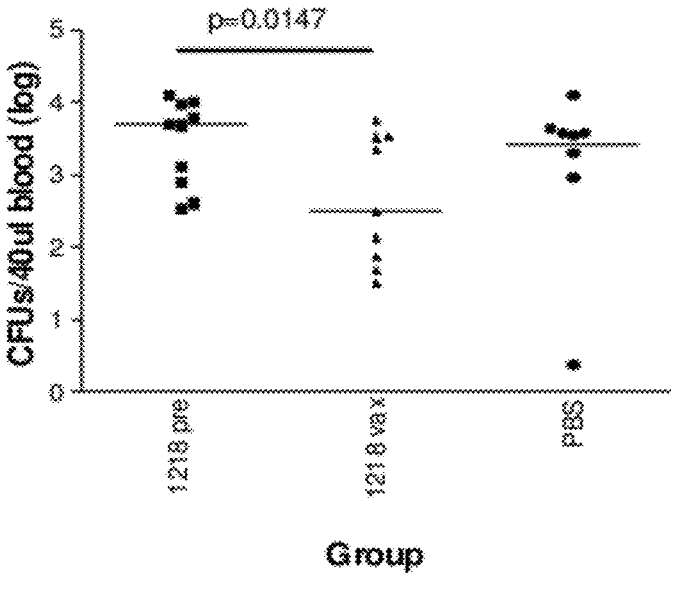

The results are shown in FIGS. 12-16. Briefly, the results demonstrated that antibodies elicited by each of the antigens significantly reduced bacteremia in the infant rats.

Although illustrated and described above with reference to specific embodiments, the invention is nevertheless not intended to be limited to the details shown. Rather, various modifications may be made in the details within the scope and range of equivalents of the claims and without departing from the spirit of the invention.

What is claimed is:

1. An immunogenic composition comprising a mixture of two polypeptides, a first polypeptide encoded by a nucleic acid set forth as SEQ ID NO:1 and a second polypeptide encoded by a nucleic acid set forth as SEQ ID NO:3.

2. The immunogenic composition of claim 1, which further comprises a physiologically-acceptable vehicle.

3. The immunogenic composition of claim 1, which further comprises an effective amount of an adjuvant.

4. The immunogenic composition of claim 1 wherein each polypeptide is capable of generating an antibody that specifically recognizes said polypeptide, and wherein the amount of said immunogenic composition is effective to ameliorate colonization or infection by β-hemolytic streptococci in a susceptible animal.

5. The immunogenic composition of claim 1, which further comprises a physiologically-acceptable vehicle.

6. The immunogenic composition of claim 1, which further comprises an effective amount of an adjuvant.

7. The immunogenic composition of claim 4, wherein the β-hemolytic streptococci is Group A streptococci.

8. The immunogenic composition of claim 7, wherein the Group A streptococci is *Streptococcus pyogenes.*

9. An immunogenic composition comprising a mixture of two polypeptides, a first polypeptide having the amino acid sequence set forth as SEQ ID NO:2 and a second polypeptide having the amino acid sequence set forth as SEQ ID NO:4.

10. The immunogenic composition of claim 9, which further comprises a physiologically-acceptable vehicle.

11. The immunogenic composition of claim 9, which further comprises an effective amount of an adjuvant.

12. The immunogenic composition of claim 9, wherein each polypeptide is capable of generating an antibody that specifically recognizes said polypeptide, and wherein the amount of said immunogenic composition is effective to ameliorate colonization or infection by β-hemolytic streptococci in a susceptible animal.

13. The immunogenic composition of claim 12, which further comprises a physiologically-acceptable vehicle.

14. The immunogenic composition of claim 12, which further comprises an effective amount of an adjuvant.

15. The immunogenic composition of claim 12, wherein the β-hemolytic streptococci is Group A streptococci.

16. The immunogenic composition of claim 15, wherein the Group A streptococci is *Streptococcus pyogenes.*

17. A method of treating a susceptible animal against colonization or infection by β-hemolytic streptococci comprising administering to the mammal an effective amount of the immunogenic composition of claim 1, wherein each polypeptide is capable of generating an antibody specific to said polypeptide, and wherein the amount of said immunogenic composition is effective to ameliorate colonization or infection by β-hemolytic streptococci in the susceptible animal.

18. The method of claim 17, wherein the immunogenic composition is administered by subcutaneous injection, by intramuscular injection, by oral ingestion, intranasally, or combinations thereof.

19. The method of claim 17 wherein the β-hemolytic streptococci is Group A streptococci.

20. The method of claim 19 wherein the Group A streptococci is *Streptococcus pyogenes.*

21. A method of treating a susceptible animal against colonization or infection by β-hemolytic streptococci comprising administering to the mammal an effective amount of the immunogenic composition of claim 9, wherein each polypeptide is capable of generating an antibody specific to said polypeptide, and wherein the amount of said immunogenic composition is effective to ameliorate colonization or infection by β-hemolytic streptococci in the susceptible mammal animal.

22. The method of claim 21, wherein the immunogenic composition is administered by subcutaneous injection, by intramuscular injection, by oral ingestion, intranasally, or combinations thereof.

23. The method of claim 21 wherein the streptococci is Group A streptococci.

24. The method of claim 23 wherein the Group A streptococci is *Streptococcus pyogenes.*

25. The immunogenic composition of clam 1 further comprising at least one other polypeptide encoded by nucleic acid set forth as SEQ. ID. NO: 5, 7 or 9.

26. The immunogenic composition of claim 25, which further comprises a physiologically-acceptable vehicle.

27. The immunogenic composition of claim 25, which further comprises an effective amount of an adjuvant.

28. The immunogenic composition of claim 25 wherein each polypeptide is capable of generating an antibody that specifically recognizes said polypeptide, and wherein the amount of said immunogenic composition is effective to ameliorate colonization or infection by β-hemolytic streptococci in a susceptible animal.

29. The immunogenic composition of claim 28, which further comprises a physiologically-acceptable vehicle.

30. The immunogenic composition of claim 28, which further comprises an effective amount of an adjuvant.

31. The immunogenic composition of claim 28, wherein the β-hemolytic streptococci is Group A streptococci.

32. The immunogenic composition of claim 31, wherein the Group A streptococci is *Streptococcus pyogenes.*

33. The immunogenic composition of clam 9 further comprising at least one other polypeptide set forth as SEQ. ID. NO: 6, 8 or 10.

34. The immunogenic composition of claim 33, which further comprises a physiologically-acceptable vehicle.

35. The immunogenic composition of claim 34, which further comprises an effective amount of an adjuvant.

36. The immunogenic composition of claim 33 wherein each polypeptide is capable of generating an antibody that specifically recognizes said polypeptide, and wherein the amount of said immunogenic composition is effective to ameliorate colonization or infection by β-hemolytic streptococci in a susceptible animal.

37. The immunogenic composition of claim 36, which further comprises a physiologically-acceptable vehicle.

38. The immunogenic composition of claim 36, which further comprises an effective amount of an adjuvant.

39. The immunogenic composition of claim 36, wherein the β-hemolytic streptococci is Group A streptococci.

40. The immunogenic composition of claim 39, wherein the Group A streptococci is *Streptococcus pyogenes.*

41. A method of treating a susceptible animal against colonization or infection by β-hemolytic streptococci comprising administering to the mammal an effective amount of the immunogenic composition of claim 25, wherein each polypeptide is capable of generating an antibody specific to said polypeptide, and wherein the amount of said immunogenic composition is effective to ameliorate colonization or infection by β-hemolytic streptococci in the susceptible animal.

42. The method of claim 41, wherein the immunogenic composition is administered by subcutaneous injection, by intramuscular injection, by oral ingestion, intranasally, or combinations thereof.

43. The method of claim 41 wherein the β-hemolytic streptococci is Group A streptococci.

44. The method of claim 43 wherein the Group A streptococci is *Streptococcus pyogenes.*

45. A method of treating a susceptible animal against colonization or infection by β-hemolytic streptococci comprising administering to the mammal an effective amount of the immunogenic composition of claim 33, wherein each polypeptide is capable of generating an antibody specific to said polypeptide, and wherein the amount of said immunogenic composition is effective to ameliorate colonization or infection by β-hemolytic streptococci in the susceptible animal.

46. The method of claim 45, wherein the immunogenic composition is administered by subcutaneous injection, by intramuscular injection, by oral ingestion, intranasally, or combinations thereof.

47. The method of claim 45 wherein the β-hemolytic streptococci is Group A streptococci.

48. The method of claim 47 wherein the Group A streptococci is *Streptococcus pyogenes.*

49. An immunogenic composition comprising a mixture of:

(a) an SCP polypeptide having the amino acid sequence of SEQ ID NO:2;

(b) a peptidylpropyl isomerase polypeptide having the amino acid sequence of SEQ ID NO:4; and (c) a putative adhesion polypeptide having the amino acid sequence of SEQ ID NO:8.

* * * * *

UNITED STATES PATENT AND TRADEMARK OFFICE

CERTIFICATE OF CORRECTION

PATENT NO. : 8,563,001 B2
APPLICATION NO. : 12/612399
DATED : October 22, 2013
INVENTOR(S) : Dodge et al.

It is certified that error appears in the above-identified patent and that said Letters Patent is hereby corrected as shown below:

Please add the following name to the title page, Item (75) of the patent as the last inventor (after Stephen Bruce Olmstead),

Add:

"Paul Patrick Cleary, Shoreview, MN;"

In the Claims

In Column 56, Line 23:

Replace:

"susceptible mammal animal."

With:

"susceptible animal."

In Column 56, Claim 23 (Line 29) please replace the entire claim,

Replace:

"The method of claim 21 wherein the streptococci is Group A streptococci"

With:

"The method of claim 21 wherein the β-hemolytic streptococci is Group A streptococci"

Signed and Sealed this
Twenty-second Day of April, 2014

Michelle K. Lee

Michelle K. Lee
*Deputy Director of the United States Patent and Trademark Office*

In Column 56, Line 33:

Replace:

"clam 1"

With:

"claim 1"

In Column 56, Line 55:

Replace:

"clam 9"

With:

"claim 9"